(12) United States Patent
Lin et al.

(10) Patent No.: US 8,524,660 B2
(45) Date of Patent: Sep. 3, 2013

(54) POLYALKYLENE POLYMER COMPOUNDS AND USES THEREOF

(75) Inventors: KoChung Lin, Lexington, MA (US); R. Blake Pepinsky, Arlington, MA (US); Ling Ling Chen, Wellesley, MA (US); Donna M. Hess, Waltham, MA (US); Edward Y. Lin, Somerville, MA (US); Russell C. Petter, Stow, MA (US); Darren P. Baker, Hingham, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 172 days.

(21) Appl. No.: 13/230,080

(22) Filed: Sep. 12, 2011

(65) Prior Publication Data

US 2012/0014916 A1 Jan. 19, 2012

Related U.S. Application Data

(60) Division of application No. 10/892,830, filed on Jul. 16, 2004, now Pat. No. 8,017,733, which is a continuation of application No. PCT/JP03/01559, filed on Jan. 17, 2003.

(60) Provisional application No. 60/349,917, filed on Jan. 18, 2002.

(51) Int. Cl.
*A61K 47/48* (2006.01)
*C08G 65/329* (2006.01)
*A61K 38/00* (2006.01)
*C07K 17/08* (2006.01)
*A61K 31/00* (2006.01)
*A61K 38/21* (2006.01)
*C07K 14/565* (2006.01)
*C12N 15/22* (2006.01)

(52) U.S. Cl.
USPC ............. 514/4.3; 514/17.9; 514/3.7; 514/2.3; 514/1.1; 514/1; 435/69.51; 436/86; 510/320; 525/525; 525/526; 530/351

(58) Field of Classification Search
None
See application file for complete search history.

(56) References Cited

U.S. PATENT DOCUMENTS

| | | | |
|---|---|---|---|
| 4,002,531 A | 1/1977 | Royer |
| 4,179,337 A | 12/1979 | Davis et al. |
| 4,670,417 A | 6/1987 | Iwasaki et al. |
| 4,751,077 A | 6/1988 | Bell et al. |
| 4,766,106 A | 8/1988 | Katre et al. |
| 4,894,226 A | 1/1990 | Adwin et al. |
| 4,917,888 A | 4/1990 | Katre et al. |
| 5,109,120 A | 4/1992 | Ueno et al. |
| 5,116,964 A | 5/1992 | Capon et al. |
| 5,252,714 A | 10/1993 | Harris et al. |
| 5,281,698 A | 1/1994 | Nitecki |
| 5,286,637 A | 2/1994 | Veronese et al. |
| 5,359,030 A | 10/1994 | Ekwuribe et al. |
| 5,382,657 A | 1/1995 | Karasiewicz et al. |
| 5,468,478 A | 11/1995 | Saifer et al. |
| 5,476,653 A | 12/1995 | Pitt et al. |
| 5,529,915 A | 6/1996 | Phillips et al. |
| 5,650,234 A | 7/1997 | Dolence et al. |
| 5,672,662 A | 9/1997 | Harris et al. |
| 5,681,811 A | 10/1997 | Martinez et al. |
| 5,702,717 A | 12/1997 | Cha et al. |
| 5,711,944 A | 1/1998 | Gilbert et al. |
| 5,738,846 A | 4/1998 | Greenwald et al. |
| 5,747,639 A | 5/1998 | Seely |
| 5,792,834 A | 8/1998 | Hakimi et al. |
| 5,824,784 A | 10/1998 | Kinstler et al. |
| 5,856,451 A | 1/1999 | Olsen et al. |
| 5,874,075 A | 2/1999 | Collins et al. |
| 5,900,461 A | 5/1999 | Harris |
| 5,932,462 A | 8/1999 | Harris et al. |
| 5,965,119 A | 10/1999 | Greenwald et al. |
| 5,985,265 A | 11/1999 | Kinstler et al. |
| 5,990,237 A | 11/1999 | Bentley et al. |
| 6,048,529 A | 4/2000 | Atassi et al. |
| 6,048,720 A | 4/2000 | Dalborg et al. |
| 6,180,095 B1 | 1/2001 | Greenwald et al. |
| 6,448,369 B1 | 9/2002 | Bentley et al. |
| 6,531,122 B1 | 3/2003 | Pedersen et al. |
| 6,602,952 B1 | 8/2003 | Bentley et al. |
| 6,638,500 B1 | 10/2003 | El-Tayar et al. |

(Continued)

FOREIGN PATENT DOCUMENTS

| | | |
|---|---|---|
| EP | 0 154 316 | 9/1989 |
| EP | 0 229 108 | 12/1990 |

(Continued)

OTHER PUBLICATIONS

Baker,DP;Lin,EY; Lin,K;Pellegrini,M;Petter,RC;Chen,LL;Arduini,RM;Brickelmaier,M;Wen,D;Hess,DM;Chen,L;Grant,D;Whitty,A;Gill,A;Lindner,DJ;Pepinsky,RB "N-Terminally PEGylated Human Interferon-.beta.-1a with Improved Pharmacokinetic Properties and in vivo Efficacy in a Melanoma Angiogenesis" Bioconj. Chem, 2006,17(1), 179-188.*
GenBank Accession No. E00029 (Sep. 29, 1997).
Karpusas et al., The Crystal Structure of Human Interferon β at 2.2-A Resolution, Proc. Natl. Acad. Sci. USA 94:11813-11818 (1997).
Runkel et al., Structural and Functional Differences Between Glycosylated and Non-glycosylated Forms of Human Interferon-β (IFN-β), Pharm. Res. 15: 641-649 (1998).
Database CAPLUS on CAS, AN 1997:758014, Sherman et al. Conjugation of high molecular weight poly(ethylene glycol) to cytokines, ACS Symposium Series, 1997.
Database CAPLUS on CAS, AN 2002:594875 for PCT WO 2002/60929 a2, BIOGEN, Aug. 8, 2002.

(Continued)

Primary Examiner — Chris R Tate
Assistant Examiner — Aaron J Kosar
(74) Attorney, Agent, or Firm — Steptoe & Johnson LLP

(57) ABSTRACT

The invention relates to novel polyalkylene glycol compounds and methods of using them. In particular, compounds comprising a novel polyethylene glycol conjugate are used alone, or in combination with antiviral agents to treat a viral infection, such as chronic hepatitis C.

3 Claims, 11 Drawing Sheets

(56) References Cited

U.S. PATENT DOCUMENTS

| | | | |
|---|---|---|---|
| 6,774,180 B2 | 8/2004 | Kozlowski et al. |
| 6,864,327 B2 | 3/2005 | Bentley et al. |
| 6,916,962 B2 | 7/2005 | Rosen et al. |
| 6,956,135 B2 | 10/2005 | Rosen et al. |
| 6,962,978 B2 | 11/2005 | Pepinsky et al. |
| 7,009,033 B2 | 3/2006 | Varshney et al. |
| 7,041,855 B2 | 5/2006 | Rosen et al. |
| 7,053,150 B2 | 5/2006 | Kozlowski et al. |
| 2001/0011115 A1 | 8/2001 | Harris et al. |
| 2001/0046481 A1 | 11/2001 | Bentley et al. |
| 2002/0044921 A1 | 4/2002 | Lee et al. |
| 2002/0091288 A1 | 7/2002 | Wilbur et al. |
| 2003/0021765 A1 | 1/2003 | Pepinsky et al. |
| 2003/0124086 A1 | 7/2003 | Bentley et al. |
| 2003/0153694 A1 | 8/2003 | Rosen et al. |
| 2003/0170206 A1 | 9/2003 | Rasmussen et al. |
| 2003/0175241 A1 | 9/2003 | Pedersen et al. |
| 2004/0043002 A1 | 3/2004 | El-Tayar et al. |
| 2004/0102381 A1 | 5/2004 | Ekwuribe et al. |
| 2004/0116649 A1 | 6/2004 | Kozlowski |
| 2004/0126361 A1 | 7/2004 | Saifer et al. |
| 2005/0176896 A1 | 8/2005 | Bentley et al. |
| 2007/0098688 A1 | 5/2007 | Pepinsky et al. |
| 2011/0165122 A1* | 7/2011 | Shahangian et al. ......... 424/85.6 |

FOREIGN PATENT DOCUMENTS

| | | |
|---|---|---|
| EP | 0 236 987 | 12/1994 |
| EP | 0 510 356 | 1/1999 |
| EP | 1 264 837 | 12/2002 |
| EP | 1 564 219 | 8/2005 |
| WO | WO 87/00056 | 1/1987 |
| WO | WO 95/13090 | 5/1995 |
| WO | WO 96/00080 | 1/1996 |
| WO | WO 96/11953 | 4/1996 |
| WO | WO 97/04796 | 2/1997 |
| WO | WO 97/18832 | 5/1997 |
| WO | WO 98/32466 | 7/1998 |
| WO | WO 98/48840 | 11/1998 |
| WO | WO 99/32134 | 7/1999 |
| WO | WO 99/32139 | 7/1999 |
| WO | WO 99/32140 | 7/1999 |
| WO | WO 99/55377 | 11/1999 |
| WO | WO 00/09073 | 2/2000 |
| WO | WO 00/23114 | 4/2000 |
| WO | WO 01/15736 | 3/2001 |
| WO | WO 01/46291 | 6/2001 |
| WO | WO 02/059179 | 8/2002 |
| WO | WO 02/074806 | 9/2002 |
| WO | WO 03/049699 | 6/2003 |
| WO | WO 2004/022630 | 3/2004 |

OTHER PUBLICATIONS

Database CAPLUS on CAS, AN 2002:235344, ZACCHIGNA, et al., 'Synthesis, Chemical and Enzymatic Stability of New Poly(ethytene glycol)-Acyclovir Prodrugs,' Famaco, vol. 57, No. 3, 2002.

Ouchi et al., Design of Antitumor Agent Terminated Poly(Ethylene Glycol) Conjugate as Macromolecular Prodrug, Polymer Preprints, 38(1):582-3 (1997).

Greenwald et al., Highly Water Soluble Taxol Dertivatives: 7-Polyethylene Glycol Carbamates and Carbonates, J. Org. Chem. 60:331-336 (1995).

Buckmann et al., Functionalization of Poly(ethytene glycol) and Monomethoxy-Poly(ethylene glycol), Makromol. Chem. 182:1379 (1981).

Zaplipsky et al., Attachment of Drugs to Polyethylene Glycols, Eur. Polym. J. 19:1177 (1983).

Andresz et al., Chemische Synthese verzweigter Polysaccharide, 5, Makromol. Chem. 179:301 (1978).

Olson et al., Preparation and Characterization of Poly(ethylene glycol)ylated Human Growth Hormone Antagonist, Chemistry & Biological Applications, pp. 170-181, Harris Zaplipsky Eds., ACS Washington, DC, 1997.

Abuchowski et al., Cancer Therapy with Chemically Modified Enzymes. I. Antitumor Properties of Polyethene Glycol-Asparaginase Conjugates, Cancer Biochem., Biophys. 7:175 (1984).

Joppich et al., Peptides Flanked by Two Polymer Chains 1, Synthesis of Glycyl-L-tryptophylglycine Substituted by Poly(ethylene oxide) at both the Carboxy and the Amino End Groups, Makromol. Chem. 180:1381 (1979).

Pitha et al., Detergents Linked to Polysaccharides; Preparation and Effects on Membranes and Cells, Eur. J. Biochem. 94:11 (1979).

Elling et al., Immunoaffinity Partitioning: Synthesis and Use of Polyethylene Glycol-Oxirane for Coupling to Bovine Serum Albumin and Monocional Antibodies, Biotech. Appl. Biochem. 13:354 (1991).

Beauchamp et al., A New Procedure for the Synthesis of Polyethylene Glycol-Protein Adducts; Effects on Function, Receptor Recognition, and Clearance of Superoxide Dismutase, Lactoferrin, and a2-Macroglobulin, Anal. Biochem. 131:25 (1998).

Tondelli et al., Poly(Ethylene Glycol) Imidazolyl Formates as Oligomeric Drug-Binding Matrices, J. Controlled Release 1:251 (1985).

Veronese et al., Surface Modification of Proteins, Activation of Monomethoxy-Polyethylene Glycols by Phenylchloroformates and Modification of Ribonuclease and Superoxide Dismutase, Appt. Biochem Biotech 11:141 (1985).

Sartore et al., Enzyme Modification by MPEG with an Amino Acid or Peptide as Spacer Arms, Appl. Biochem. Biotech, 27:45 10 (1991).

Harris et al., Synthesis and Characterization of Poly(ethylene Glycol) Derivatives, J. Poly. Scit. Chem. Ed. 22:341 (1984).

Goodson et al., Site-directed Pegylation of Recombinant Interlaukin-2 At its Glycosylation Site, Bio/Technology 8:343 (1990).

Romani et al. Synthesis of Unsymmetical Cystine Peptides: Directed Disulfide Pairing with the Sulfenohydrazide Method, Chemistry of Peptides and Proteins 2:29 (1984).

TP Kogan. The Synthesis of Substituted Methoxy-Poly(ethyleneglycol) Derivatives Suitable for Selective Protein Modification, Synthetic Comm. 22:2417 (1992).

Woghiren et al., Protected Thiol-Polyethylene Glycol: A New Activated Polymer for Reversible Protein Modification, Biocong. Chem. 4:314 (1993).

Sawhney et al., Bioerodible Hydrogels Based on Photopolymerized Poly(ethylene glycol)-co-poly($\alpha$-hydroxy acid) Diacrytate Macromers, Macromolcules, 26:581 (1993).

International Search Report for PCT/US03/01559 mailed Aug. 13, 2003.

Lane , C. F."Sodium Cyanoborohydride—A Highly Selective Reducing Agent for Organic Functional Groups," Synthesis, 1975, F, pp. 135-146.

Filpula , D. and Zhao, H. "Releasable PEGylation of Proteins with Customized Linkers," Advanced Drug Delivery Reviews, 60 (2008) 29-49.

Basu, A. et al., "Structure-Function Engineering of Interferon-beta-lb for Improving Stability, Solubility, Potency, Immunogenicity, and Pharmacokinetic Properties by Site-Selective Mono-PEGylation" Bioconjugate Chem. 2006, 17, pp. 618-630.

Van den Berg-Vos, R.M., et al. "Treatment of multifocal motor neuropathy with interferon-$\beta$1A" Neurology 2000, 54, pp. 1518-1521.

Reddy, KR. "Controlled-release, pegylation, liposomal formulations: new mechanisms in the delivery of injectable drugs" Ann. Pharmacother., Jul. 2000; 34, pp. 915-923.

Ranu, B.C. et al. "One-Pot Reductive Amination of Conjugated Aldehydes and Ketones with Silica Gel and Zinc Borohydride" J Org. Chem., 1998, 63 (2), pp. 370-373.

Laid Open Japanese Patent Publication No. 10-502401, the Gazette (Mar. 3, 1998).

mPEG propionaldehyde, Shearwater Catalog: Polyethylene Glycol and Derivatives for Biomedical Applications, 2001 pp. 1-18.

Gaertner, H.F. and Offord, R.E. Bioconj. Chem. 1996. 7(1), pp. 38-44.

Inada, Y., et al., Methods Enzymol. 1994, 242, pp. 65-90.

Pepinsky, R.B. et al., The Journal of Pharmacology and Experimental Therapeutics, 2001, 297(3), 1059-1066.

* cited by examiner

A

B

POLYALKYLENE POLYMER COMPOUNDS AND USES THEREOF

CLAIM OF PRIORITY

This application is a divisional application of U.S. patent application Ser. No. 10/892,830, filed on Jul. 16, 2004, now U.S. Pat. No. 8,017,733, which is a continuation of International Patent Application Ser. No. PCT/US03/01559, filed on Jan. 17, 2003, which claims the benefit of U.S. Provisional Application Ser. No. 60/349,917, filed on Jan. 18, 2002, each of which is hereby incorporated by reference in its entirety for all purposes.

FIELD OF THE INVENTION

The invention relates to novel polyalkylene glycol compounds, conjugates of the polymers and proteins, and uses thereof.

BACKGROUND OF THE INVENTION

Covalent attachment of hydrophilic polymers, such as polyalkylene glycol polymers, also known as polyalkylene oxides, to biologically-active molecules and surfaces is of interest in biotechnology and medicine.

In particular, much research has focused on the use of poly(ethylene glycol) (PEG), also known as or poly(ethylene oxide) (PEO), conjugates to enhance solubility and stability and to prolong the blood circulation half-life of molecules.

In its most common form, PEG is a linear polymer terminated at each end with hydroxyl groups:

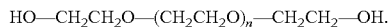

The above polymer, alpha-, omega-dihydroxylpoly(ethylene glycol), can also be represented as HO-PEG-OH, where it is understood that the -PEG-symbol represents the following structural unit:

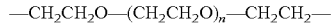

where n typically ranges from about 4 to about 10,000. PEG is commonly used as methoxy-PEG-OH, or mPEG, in which one terminus is the relatively inert methoxy group, while the other terminus is a hydroxyl group that is subject to ready chemical modification. Additionally, random or block copolymers of different alkylene oxides (e.g., ethylene oxide and propylene oxide) that are closely related to PEG in their chemistry can be substituted for PEG in many of its applications.

To couple PEG to a molecule of interest, it is often necessary to activate the PEG by preparing a derivative of the PEG having a reactive functional group at least at one terminus. The functional group is chosen based on the type of available reactive group on the molecule that will be coupled to the PEG.

PEG is a polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, it has been shown that the water-insoluble drug paclitaxel, when coupled to PEG, becomes water-soluble. Greenwald, et al., *J. Org. Chem.*, 60:331-336 (1995).

The prodrug approach, in which drugs are released by degradation of more complex molecules (prodrugs) under physiological conditions, is a powerful component of drug delivery. Prodrugs can, for example, be formed by bonding PEG to drugs via linkages which are degradable under physiological conditions. The lifetime of PEG prodrugs in vivo depends upon the type of functional group(s) forming linkages between PEG and the drug. In general, ester linkages, formed by reaction of PEG carboxylic acids or activated PEG carboxylic acids with alcohol groups on the drug hydrolyze under physiological conditions to release the drug, while amide and carbamate linkages, formed from amine groups on the drug, are stable and do not hydrolyze to release the free drug. It has been shown that hydrolytic delivery of drugs from PEG esters can be favorably controlled to a certain extent by controlling the number of linking methylene groups in a spacer between the terminal PEG oxygen and the carbonyl group of the attached carboxylic acid or carboxylic acid derivative. For example, Harris et al., in U.S. Pat. No. 5,672,662, describe PEG butanoic acid and PEG propanoic acid, and activated derivatives thereof, as alternatives to carboxymethyl PEG for compounds where less hydrolytic reactivity in the corresponding ester derivatives is desirable. See, generally, PCT publication WO 01/46291.

One factor limiting the usefulness of proteinaceous substances for medical treatment applications is that, when given parenterally, they are eliminated from the body within a short time. This elimination can occur as a result of degradation by proteases or by clearance using normal pathways for protein elimination such as by filtration in the kidneys. Oral administration of these substances is even more problematic because, in addition to proteolysis in the stomach, the high acidity of the stomach destroys these substances before they reach their intended target tissue. The problems associated with these routes of administration of proteins are well known in the pharmaceutical industry, and various strategies are being employed in attempts to solve them. A great deal of work dealing with protein stabilization has been published. Various ways of conjugating proteins with polymeric materials are known, including use of dextrans, polyvinyl pyrrolidones, glycopeptides, polyethylene glycol, and polyamino acids. The resulting conjugated polypeptides are reported to retain their biological activities and solubility in water for parenteral applications.

Of particular interest is increasing the biological activity of interferons while reducing the toxicity involved with use of these proteins for treating human patients. Interferons are a family of naturally-occurring small proteins and glycoproteins produced and secreted by most nucleated cells in response to viral infection as well as to other antigenic stimuli. Interferons render cells resistant to viral infection and exhibit a wide variety of actions on cells. They exert their cellular activities by binding to specific membrane receptors on the cell surface. Once bound to the cell membrane, interferons initiate a complex sequence of intracellular events. In vitro studies have demonstrated that these include the induction of certain enzymes; suppression of cell proliferation, immunomodulation activities such as enhancement of the phagocytic activity of macrophages; augmentation of the specific cytotoxicity of lymphocytes for target cells; and inhibition of virus replication in virus-infected cells.

Interferons have been tested in the treatment of a variety of clinical disease states. The use of human interferon beta has been established in the treatment of multiple sclerosis. Two forms of recombinant interferon beta, have recently been licensed in Europe and the U.S. for treatment of this disease: interferon-beta-1a (AVONEX®, Biogen, Inc., Cambridge, Mass. and REBIF® Serono, Geneva, Switzerland) and interferon-beta-1b (BETASERON®, Berlex, Richmond, Calif.). Interferon beta-1a is produced in mammalian cells using the natural human gene sequence and is glycosylated, whereas interferon beta-1b is produced in *E. coli* bacteria using a modified human gene sequence that contains a genetically engineered cysteine-to-serine substitution at amino acid position 17 and is non-glycosylated.

Non-immune interferons, which include both alpha and beta interferons, are known to suppress human immunodeficiency virus (HIV) in both acutely and chronically-infected cells. See Poli and Fauci, 1992, AIDS Research and Human Retroviruses 8(2):191-197. Due to their antiviral activity, interferons, in particular alpha interferons, have received considerable attention as therapeutic agents in the treatment of hepatitis C virus (HCV)-related disease. See Hoofnagle et al., in: Viral Hepatitis 1981 International Symposium, 1982, Philadelphia, Franklin Institute Press; Hoofnagle et al., 1986, New Eng. J. Med. 315:1575-1578; Thomson, 1987, Lancet 1:539-541 Kiyosawa et al., 1983, in: Zuckerman, ed., Viral Hepatitis and Liver Disease, Allen K. Liss, New York pp. 895-897; Hoofnagle et al., 1985, Sem. Liv. Dis., 1985, 9:259-263.

Interferon-polymer conjugates are described in, for example, U.S. Pat. No. 4,766,106, U.S. Pat. No. 4,917,888, European Patent Application No. 0 236 987, European Patent Application No. 0 510 356 and International Application Publication No. WO 95/13090.

Chronic hepatitis C is an insidious and slowly progressive disease having a significant impact on the quality of life. Despite improvement in the quality of the blood-donor pool and the recent implementation of testing of donated blood for HCV, the estimated incidence of acute infection among persons receiving transfusions is 5 to 10%. See Alter et al., in: Zuckerman, ed., Viral Hepatitis and Liver Disease, Allen K. Liss, New York. 1988, pp. 537-542. Thus, of the approximately 3 million persons who receive transfusions in the United States each year, acute hepatitis C will develop in about 150,000. While many patients who contract hepatitis C will have subclinical or mild disease, approximately 50% will progress to a chronic disease state characterized by fluctuating serum transaminase abnormalities and inflammatory lesions on liver biopsy. It is estimated that cirrhosis will develop in up to about 20% of this group. See Koretz et al., 1985, Gastroenterology 88:1251-1254.

Interferons are known to affect a variety of cellular functions, including DNA replication, and RNA and protein synthesis, in both normal and abnormal cells. Thus, cytotoxic effects of interferon are not restricted to tumor or virus-infected cells but are also manifested in normal, healthy cells. As a result, undesirable side effects may arise during interferon therapy, particularly when high doses are required. Administration of interferon can lead to myelosuppression, thereby resulting in reduced red blood cell count, and reduced white blood cell and platelet levels. Interferons commonly give rise to flu-like symptoms (e.g., fever, fatigue, headaches and chills), gastrointestinal disorders (e.g., anorexia, nausea and diarrhea), dizziness and coughing. Often, the sustained response of HCV patients to non-PEGylated interferon treatment is low and the treatment can induce severe side effects, including, but not limited to, retinopathy, thyroiditis, acute pancreatitis, and depression.

The undesirable side effects that accompany interferon therapy frequently limit the therapeutic usefulness of interferon treatment regimes. Thus, a need exists to maintain or improve the therapeutic benefits of such therapy while reducing or eliminating the undesirable side effects.

SUMMARY OF THE INVENTION

The invention relates to novel polyalkylene glycol compounds, conjugates of these compounds, and uses thereof.

In one aspect, the invention relates to an activated polyalkylene glycol polymer having the structure according to Formula I:

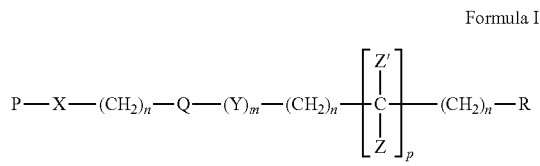

Formula I wherein P is a polyalkylene glycol polymer;

X and Y are independently O, S, CO, $CO_2$, COS, SO, $SO_2$, CONR', $SO_2$NR', or NR';

Q is a $C_3$ to $C_3$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonamido, sulfonyl, heterocyclyl, aralkyl, aromatic moiety, heteroaromatic moiety, imino, sulfamoyl, sulfonate, silyl, ether, and alkylthio;

each R', Z and Z' is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, sulfamoyl, sulfonate, silyl, ether, and alkylthio;

R is a moiety suitable for forming a bond between the compound of Formula I and a biologically-active compound or precursor thereof;

m is 0 or 1;

each n is independently 0 or an integer from 1 to 5; and p is 1, 2, or 3.

In another aspect, the invention relates to an activated polyalkylene glycol compound (PGC) having the structure according to Formula Ia:

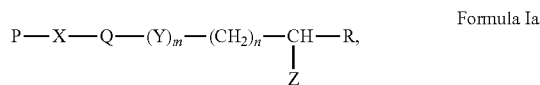

Formula Ia where P is a polyalkylene glycol polymer, m is zero or one, n is zero or an integer from one to five, and X and Y are independently O, S, CO, $CO_2$, COS, SO, $SO_2$, CONR', $SO_2$NR', or NR'.

Q is a $C_3$ to $C_8$ saturated or unsaturated cyclic alkyl or cyclic heteroalkyl, a substituted or unsubstituted aryl or heteroaryl group, or a substituted or unsubstituted alkaryl wherein the alkyl is a $C_1$ to $C_{20}$ saturated or unsaturated alkyl or heteroalkaryl group. If present, the substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonamido, sulfonyl, heterocyclyl, aralkyl, aromatic moiety, heteroaromatic moiety, imino, sulfamoyl, sulfonate, silyl, ether, or alkylthio. Heterocyclic and carbocyclic groups include fused bicyclic and bridged bicyclic ring structures.

Each R' and Z is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

Compounds which include chiral carbons can be in the R configuration, the S configuration, or may be racemic.

R is a moiety suitable for forming a bond between the compound of Formula I and a biologically-active compound or precursor thereof.

In one embodiment, R is a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or a glyoxal moiety.

In certain embodiments, P is a polyethylene glycol having the structure of Formula II:

  Formula II where E is hydrogen or a straight- or branched-chain $C_1$ to $C_{20}$ alkyl group and a is an integer from 4 to 10,000. For example, E can be a methyl group.

In other embodiments, E can be a detectable label, such as, for example, a radioactive isotope, a fluorescent moiety, a phosphorescent moiety, a chemiluminescent moiety, or a quantum dot.

In yet other embodiments, E is a moiety suitable for forming a bond between the compound of Formula I and a biologically-active compound or precursor thereof. For example, E can be a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or a glyoxal moiety.

In still other embodiments, E has the structure according to Formula III or Formula IV:

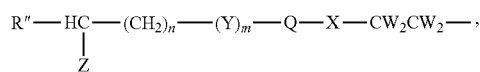

Formula III

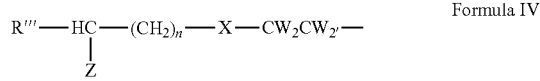

Formula IV where each Q, X, Y, Z, m, and n are, independently, as defined above; and each W is, independently, hydrogen or a $C_1$ to $C_7$ alkyl.

R" is a moiety suitable for forming a bond between the compound of Formula III and a biologically-active compound or precursor thereof, and R''' is a moiety suitable for forming a bond between the compound of Formula IV and a biologically-active compound or precursor thereof. For example, R" and R''' can be a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or a glyoxal moiety. R" and R''' can be the same or different from R.

In particular embodiments, Q is a substituted or unsubstituted alkaryl.

In another aspect, the invention relates to an activated PGC having the structure according to Formula V:

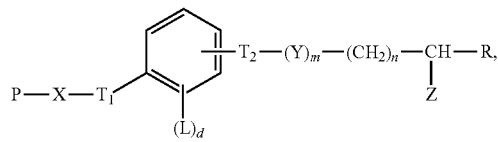

Formula V where P, X, Y, R', Z, R, m, and n are as defined, and $T_1$ and $T_2$ are, independently, absent, or a straight- or branched-chain, saturated or unsaturated $C_1$ to $C_{20}$ alkyl or heteroalkyl group, a $C_3$ to $C_8$ saturated or unsaturated cyclic alkyl or cyclic heteroalkyl, a substituted or unsubstituted aryl or heteroaryl group, or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

L may be absent (e.g., d is zero) or there may be from one to four (e.g., n is an integer from one to four) L substituents on the aromatic ring in addition to the $T_1$ and $T_2$ substituents, and each L is, independently, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents are selected from halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

R is a moiety suitable for forming a bond between the compound of Formula V and a biologically-active compound or precursor thereof. For example, R is chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In one embodiment of the activated polyalkylene glycol polymer of Formula V, P is a polyethylene glycol having the structure of Formula II:

$$E\text{-}(O\text{—}CH_2CH_2)_a\text{—},\qquad\text{Formula II}$$

where E is hydrogen or a straight- or branched-chain $C_1$ to $C_{20}$ alkyl group and a is an integer from 4 to 10,000. For example, E can be methyl. In other embodiments, E is a detectable label, such as, for example, a radioactive isotope, fluorescent moiety, phosphorescent moiety, chemiluminescent moiety, or a quantum dot.

In another aspect, P is a polyethylene glycol having the structure of Formula II:

$$E\text{-}(O\text{—}CH_2CH_2)_a\text{—},\qquad\text{Formula II}$$

where E is a moiety suitable for forming a bond between the compound of Formula V and a biologically-active compound or precursor thereof and a is an integer from 4 to 10,000. For example, E is chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

In another aspect, E has the structure according to Formula III or Formula IV:

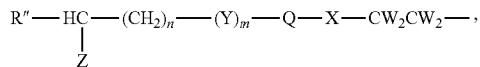

Formula III

Formula IV where Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl; the alkyl is a $C_1$ to $C_{20}$ saturated or unsaturated alkyl or heteroalkaryl group, and the substituents can be of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

X, Y, Z, m, and n are as defined, and each W is, independently, hydrogen or a $C_1$ to $C_7$ alkyl; and R″ is a moiety suitable for forming a bond between the compound of Formula III and a biologically-active compound or precursor thereof, and R‴ is a moiety suitable for forming a bond between the compound of Formula IV and a biologically-active compound or precursor thereof.

In certain embodiments, R″ and R‴ can be the same as or different from R, and are chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties. In one embodiment of the compound of Formula V, X and Y, if present, are oxygen.

In another aspect the invention relates to an activated PGC having the structure according to Formula VI:

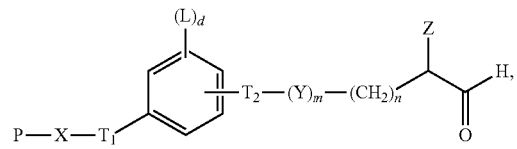

Formula VI where P is a polyalkylene glycol polymer, m is zero or one, n is zero or an integer from one to five, X and Y are independently O, S, CO, $CO_2$, COS, SO, $SO_2$, CONR′, $SO_2NR′$, or NR′, and $T_1$ and $T_2$ are, independently, absent, or a straight- or branched-chain, saturated or unsaturated $C_1$ to $C_{20}$ alkyl or heteroalkyl group.

Each R′ and Z is, independently, hydrogen, a straight- or branched-chain, saturated or unsaturated $C_1$ to $C_{20}$ alkyl or heteroalkyl group.

d is zero or an integer from one to four, and each L is, independently, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents are selected from halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio moieties.

In one embodiment, the activated PGC according to Formula VI has the structure according to Formula VII or Formula VIII:

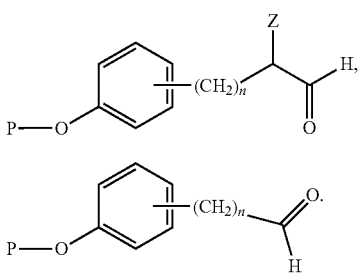

Formula VII

Formula VIII

In one embodiment of the activated polyalkylene glycol compounds of Formulae VII and VIII, P is a polyethylene glycol having the structure of Formula II:

$$\text{E-(O—CH}_2\text{CH}_2)_a\text{—,} \quad \text{Formula II}$$

where E is hydrogen or a straight- or branched-chain $C_1$ to $C_{20}$ alkyl group and a is an integer from 4 to 10,000. For example, E can be methyl. In other embodiments, E is a detectable label, such as, for example, a radioactive isotope, fluorescent moiety, phosphorescent moiety, chemiluminescent moiety, or a quantum dot.

In another aspect, P is a polyethylene glycol having the structure of Formula II:

$$\text{E-(O—CH}_2\text{CH}_2)_a\text{—,} \quad \text{Formula II}$$

where E is a moiety suitable for forming a bond between the compound of Formula VII or VIII and a biologically-active compound or precursor thereof and a is an integer from 4 to 10,000. For example, E is chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

In another aspect, E has the structure according to Formula III or Formula N:

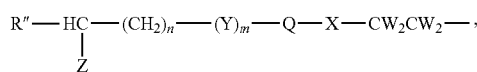

Formula III

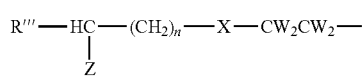

Formula IV where Q is a $C_3$ to $C_8$ saturated or unsaturated cyclic alkyl or cyclic heteroalkyl, a substituted or unsubstituted aryl or heteroaryl group, or a substituted or unsubstituted alkaryl; the alkyl is a $C_1$ to $C_{20}$ saturated or unsaturated alkyl or heteroalkaryl group, and the substituents can be of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio. Heterocyclic and carbocyclic groups include fused bicyclic and bridged bicyclic ring structures X, Y, Z, m, and n are as defined, and each W is, independently, hydrogen or a $C_1$ to $C_7$ alkyl; and R" is a moiety suitable for forming a bond between the compound of Formula III and a biologically-active compound or precursor thereof, and R'" is a moiety suitable for forming a bond between the compound of Formula IV and a biologically-active compound or precursor thereof.

In certain embodiments, R" and R'" can be the same as or different from R, and are chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

In one embodiment, the activated polyalkylene glycol compound of Formula VIII, the ring substituents are located in a meta arrangement. In another embodiment, the ring substituents are located in a para arrangement.

In another embodiment, the activated polyalkylene glycol compound according to Formula VI, has the structure according to Formula IX:

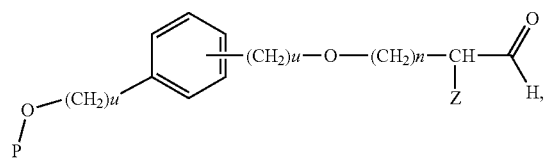

Formula IX where P is a polyalkylene glycol polymer, each n and u are, independently, zero or an integer from one to five; and Z is hydrogen, a straight- or branched-chain, saturated or unsaturated $C_1$ to $C_{20}$ alkyl or heteroalkyl group.

In one embodiment of the compounds of Formula IX, the ring substituents are located in a meta arrangement. In another embodiment of the compounds of Formula IX, the ring substituents are located in a para arrangement.

In another embodiment of the compounds of Formula IX, P is a polyethylene glycol having the structure of Formula II:

$$\text{E-(O—CH}_2\text{CH}_2)_a\text{—,} \quad \text{Formula II}$$

where E is hydrogen, a straight- or branched-chain $C_1$ to $C_{20}$ alkyl group, a detectable label, or a moiety suitable for forming a bond between the compound of Formula IX and a biologically-active compound or precursor thereof and a is an integer from 4 to 10,000.

In another aspect, the invention involves an activated polyalkylene glycol polymer having the structure according to Formula X:

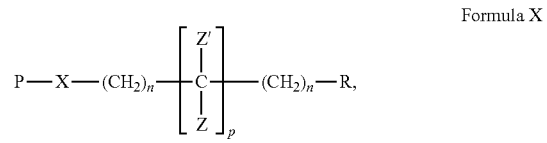

Formula X wherein P is a polyalkylene glycol polymer;
X is O, S, CO, $CO_2$, COS, SO, $SO_2$, CONR', $SO_2$NR', or NR';

R' is hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

Z and Z' are individually hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio, provided that at least one Z or Z' is not hydrogen;

R is a moiety suitable for forming a bond between the compound of Formula X and a biologically-active compound or precursor thereof;

each n is independently 0 or an integer from 1 to 5; and p is 1, 2, or 3.

In another aspect, the invention involves an activated polyalkylene glycol compound (PGC) having the structure according to Formula Xa:

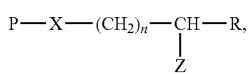   Formula Xa

In these compounds, P is a polyalkylene glycol polymer, such as, for example, PEG or mPEG.

X is O, S, CO, $CO_2$, COS, SO, $SO_2$, CONR', $SO_2NR'$, or NR', and R', if present, is hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

Z is a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

R is a moiety suitable for forming a bond between the compound of Formula X and a biologically-active compound or precursor thereof; and n is 0 or an integer from 1 to 5, such that there are between zero and five methylene groups between X and the Z-containing carbon.

In one embodiment, R is chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In another embodiment, P is a polyethylene glycol having the structure of Formula II:

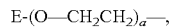   Formula II wherein E is hydrogen, a straight- or branched-chain $C_1$ to $C_{20}$ alkyl group, or a detectable label; and a is an integer from 4 to 10,000. In a further embodiment, E may be methyl.

In yet another embodiment, P is a polyethylene glycol having the structure of Formula II, wherein E is a moiety suitable for forming a bond between the compound of Formula X and a biologically-active compound or precursor thereof and a is an integer from 4 to 10,000.

In an additional embodiment, E is chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal. Alternatively, E may have the structure according to Formula III:

Formula III

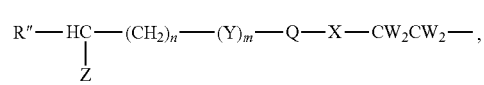

wherein P is a polyalkylene glycol polymer,

X and Y are independently O, S, CO, $CO_2$, COS, SO, $SO_2$, CONR', $SO_2NR'$, or NR';

Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

R' and each Z are independently as described above;
m is 0 or 1;
each W is, independently, hydrogen or a $C_1$ to $C_7$ alkyl;
each n is independently 0 or an integer from 1 to 5; and
R" is a moiety suitable for forming a bond between the compound of Formula III and a biologically-active compound or precursor thereof. Heterocyclic and carbocyclic groups include fused bicyclic and bridged bicyclic ring structures.

In still a further embodiment, E has the structure according to Formula IV:

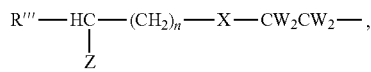

Formula IV wherein each X, Z and n are, independently, as defined;
each W is, independently, hydrogen or a $C_1$ to $C_7$ alkyl; and
R''' is a moiety suitable for forming a bond between the compound of Formula IV and a biologically-active compound or precursor thereof.

In an additional embodiment, R" is chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In a further embodiment, R' is chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In another embodiment, E is a detectable label. Additionally, E may be selected from the group consisting of radioactive isotopes, fluorescent moieties, phosphorescent moieties, chemiluminescent moieties, and quantum dots.

In still another embodiment, the activated PGC according to the invention has the structure according to Formula XI:

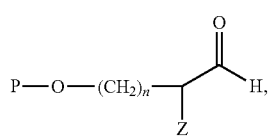

Formula XI wherein P is a polyalkylene glycol polymer; and
n and Z are as defined.

In another embodiment, the activated polyalkylene glycol has the structure according to Formula XII:

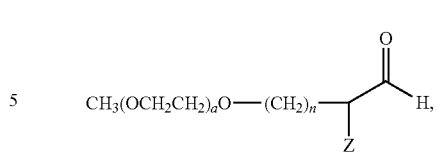

Formula XII wherein n, a, and Z are as defined above. In one embodiment, Z may be methyl. In some embodiments, n is one.

In another aspect, the invention involves an activated polyalkylene glycol compound of having the structure according to Formula XIII:

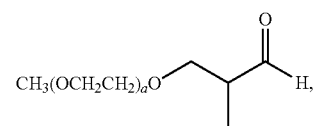

Formula XIII where a is an integer from 4 to 10,000.

The invention is also concerned with a composition of the activated polyalkylene glycol compounds of the invention and a biologically-active compound or precursor thereof. In various embodiments, the biologically-active compound or precursor thereof is chosen from the group consisting of a peptide, peptide analog, protein, enzyme, small molecule, dye, lipid, nucleoside, oligonucleotide, oligonucleotide analog, sugar, oligosaccharide, cell, virus, liposome, microparticle, surface, and a micelle.

In another aspect, the invention provides a composition having the structure according to Formula XIV:

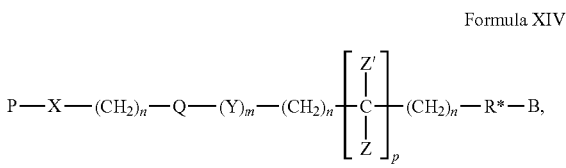

Formula XIV wherein P is a polyalkylene glycol polymer,
X and Y are independently O, S, CO, $CO_2$, COS, SO, $SO_2$, CONR', $SO_2NR'$, or NR';
Q is a $C_3$ to $C_8$ saturated or unsaturated cyclic alkyl or cyclic heteroalkyl, a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;
each R', Z, and Z' is independently hydrogen, a straight- or branched-chain, saturated or unsaturated $C_1$ to $C_{20}$ alkyl or heteroalkyl group, $C_3$ to $C_9$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

R* is a linking moiety;

B is a biologically-active compound or precursor thereof;

m is 0 or 1;

each n is independently 0 or an integer from 1 to 5; and p is 1, 2, or 3.

In another aspect, the invention involves a composition having the structure according to Formula XIVa:

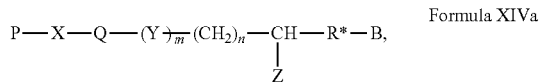

Formula XIVa wherein P is a polyalkylene glycol polymer;

X and Y are independently O, S, CO, $CO_2$, COS, SO, $SO_2$, CONR', $SO_2NR'$, or NR';

Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group (including fused bicyclic and bridged bicyclic ring structures), or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

each R' and Z is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

R* is a linking moiety formed from the reaction of R with a biologically-active compound or precursor thereof;

B is a biologically-active compound or precursor thereof after conjugation with R;

m is 0 or 1; and n is 0 or an integer from 1 to 5.

In one embodiment, R* is a linking moiety formed from the reaction of R with a biologically-active compound or precursor thereof. For example, R is a moiety selected from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In another embodiment, P is a polyethylene glycol having the structure of Formula II:

Formula II wherein E is hydrogen, a straight- or branched-chain $C_1$ to $C_{20}$ alkyl group, or a detectable label; and a is an integer from 4 to 10,000. In this embodiment, E may be methyl.

In a further embodiment, P is a polyethylene glycol having the structure of Formula II:

Formula II wherein E is a moiety suitable for forming a bond between the compound of Formula XIV and a biologically-active compound or precursor thereof and a is an integer from 4 to 10,000. Here, in still a further embodiment, E may form a bond to another biologically-active compound, B. Alternatively, E may form a bond to a biologically-active compound other than B. E may also form an additional bond to the biologically-active compound, B.

In various embodiments, E may be chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal. In another embodiment, E may have the structure according to Formula III:

Formula III wherein each Q, X, Y, Z, m, and n are, independently, as defined, each W is, independently, hydrogen or a $C_1$ to $C_7$ alkyl; and R" is a moiety suitable for forming a bond between the compound of Formula III and a biologically-active compound or precursor thereof.

In a further embodiment, E has the structure according to Formula IV:

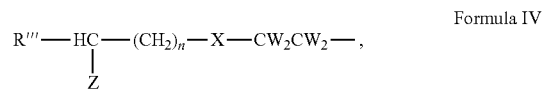

Formula IV wherein each X, Z and n are, independently, as defined, each W is, independently, hydrogen or a $C_1$ to $C_7$ alkyl; and R''' is a moiety suitable for forming a bond between the compound of Formula IV and a biologically-active compound or precursor thereof.

In various embodiments, R" is chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

Likewise, in other embodiments, R''' is chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In still other embodiments, E is a detectable label. For example, E may be selected from the group consisting of radioactive isotopes, fluorescent moieties, phosphorescent moieties, chemiluminescent moieties, and quantum dots.

In various embodiments, Q is a substituted or unsubstituted alkaryl.

In another aspect, the invention involves a composition having the structure according to Formula XV:

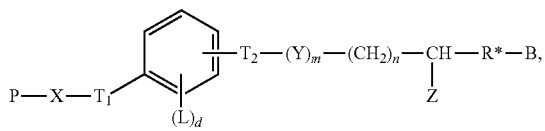

Formula XV wherein P is a polyalkylene glycol polymer, m is zero or one; d is zero or an integer from one to four, and n is zero or an integer from one to five.

X and Y are independently O, S, CO, $CO_2$, COS, SO, $SO_2$, CONR', $SO_2NR'$, or NR'; and $T_1$ and $T_2$ are, independently, absent, or a straight- or branched-chain, saturated or unsaturated $C_1$ to $C_{20}$ alkyl or heteroalkyl group, a $C_3$ to $C_8$ saturated or unsaturated cyclic alkyl or cyclic heteroalkyl, a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

Each R' and Z is, independently, hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

Each L is, independently, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

R* is a linking moiety formed from the reaction of R with a biologically-active compound or precursor thereof, and B is a biologically-active compound, or precursor thereof, after conjugation with R.

For example, R may be a moiety selected from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In another embodiment, P is a polyethylene glycol having the structure of Formula II:

Formula II wherein E is hydrogen, a straight- or branched-chain $C_1$ to $C_{20}$ alkyl group, or a detectable label; and a is an integer from 4 to 10,000. In this embodiment, E may be methyl.

In still another aspect, P is a polyethylene glycol having the structure of Formula II:

Formula II wherein E is a moiety suitable for forming a bond between the compound of Formula XV and a biologically-active compound or precursor thereof and a is an integer from 4 to 10,000. Here, E may be selected from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal. Additionally, E may have the structure according to:

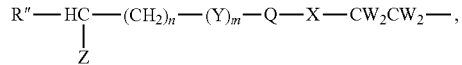

Formula III wherein Q is a $C_3$ to $C_8$ saturated or unsaturated cyclic alkyl or cyclic heteroalkyl, (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

each X, Y, Z, m, and n are, independently, as defined;

each W is, independently, hydrogen or a $C_1$ to $C_7$ alkyl; and

R″ is a moiety suitable for forming a bond between the compound of Formula III and a biologically-active compound or precursor thereof.

In another embodiment, E can have the structure according to Formula IV:

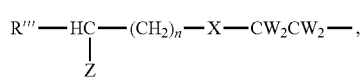

Formula IV wherein X, Z and n are as defined;

each W is, independently, hydrogen or a $C_1$ to $C_7$ alkyl; and

R‴ is a moiety suitable for forming a bond between the compound of Formula IV and a biologically-active compound or precursor thereof.

In still another embodiment, R″ is chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

Likewise, in other embodiments, R‴ may selected from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In other embodiments, E is a detectable label. For example, E may be selected from the group consisting of radioactive isotopes, fluorescent moieties, phosphorescent moieties, chemiluminescent moieties, and quantum dots.

In another aspect, the invention relates to a composition having the structure according to Formula XVI:

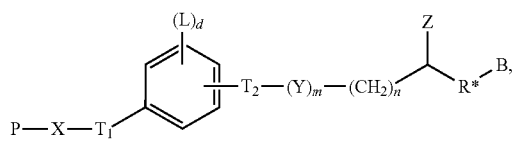

Formula XVI where m is 0 or 1, n is 0 or an integer from I to 5, P is a polyalkylene glycol polymer, X and Y are independently O, S, CO, $CO_2$, COS, SO, $SO_2$, CONR′, $SO_2$NR′, or NR′, $T_1$ and $T_2$ are, independently, absent, or a straight- or branched-chain, saturated or unsaturated $C_1$ to $C_{20}$ alkyl or heteroalkyl group, and each R′ and Z is independently hydrogen, a straight- or branched-chain, saturated or unsaturated $C_1$ to $C_{20}$ alkyl or heteroalkyl group;

d is 0 or an integer from 1 to 4, and each L is, independently, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents are selected from halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio groups.

R* is a linking moiety formed from the reaction of R with a biologically-active compound or precursor thereof, and B is a biologically-active compound, or precursor thereof, after conjugation with R.

For example, R may be a moiety selected from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In one embodiment, R* is a methylene group and B is a biologically-active molecule having an amino group, where the methylene group forms a bond with the amino group on B.

In certain embodiments, the amine is the amino terminus of a peptide, an amine of an amino acid side chain of a peptide, or an amine of a glycosylation substituent of a glycosylated peptide. For example, the peptide can be an interferon, such as interferon-beta, e.g., interferon-beta-1a.

In some embodiments, the compound according to Formula XVI has a structure according to Formula XVII:

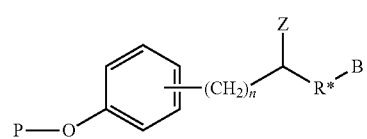

Formula XVII where P is a polyalkylene glycol polymer, Z is hydrogen, a straight- or branched-chain, saturated or unsaturated $C_1$ to $C_{20}$ alkyl or heteroalkyl group, n is 0 or an integer from 1 to 5.

R* is a linking moiety formed from the reaction of R with a biologically-active compound or precursor thereof, and 13 is a biologically-active compound, or precursor thereof, after conjugation with R.

For example, R may be a moiety selected from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In one embodiment, R* of Formula XVII is a methylene group and B is a biologically-active molecule having an amino group, where the methylene group forms a bond with the amino group on B.

In certain embodiments, the amine is the amino terminus of a peptide, an amine of an amino acid side chain of a peptide, or an amine of a glycosylation substituent of a glycosylated peptide. For example, the peptide can be an interferon, such as interferon-beta, e.g., interferon-beta-1a.

In other embodiments, the compound according to Formula XVI has a structure according to Formula XVIII:

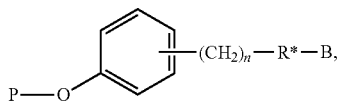

Formula XVIII where P is a polyalkylene glycol polymer, R* is a linking moiety, B is a biologically-active molecule, and n is one or two.

In one embodiment, R* of Formula XVIII is a methylene group and B is a biologically-active molecule having an amino group, where the methylene group forms a bond with the amino group on B.

In certain embodiments, the amine is the amino terminus of a peptide, an amine of an amino acid side chain of a peptide, or an amine of a glycosylation substituent of a glycosylated peptide. For example, the peptide can be an interferon, such as interferon-beta, e.g., interferon-beta-1a.

In certain embodiments of the compound according to Formula XVI, P is a polyethylene glycol having the structure of Formula II:

$$E\text{-}(O\text{---}CH_2CH_2)_a\text{---},$$ Formula II wherein E is hydrogen, a straight- or branched-chain $C_1$ to $C_{20}$ alkyl (e.g., methyl) group, a detectable label, or a moiety suitable for forming a bond between the compound of Formula XVI and a biologically-active compound or precursor thereof and a is an integer from 4 to 10,000. When E is a detectable label, the label can be, for example, a radioactive isotope, fluorescent moiety, phosphorescent moiety, chemiluminescent moiety, or a quantum dot.

In another embodiment, where E is a moiety suitable for forming a bond between the compound of Formula XVI and a biologically-active compound or precursor thereof, E is chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

In another embodiment, E has the structure according to Formula III or Formula IV:

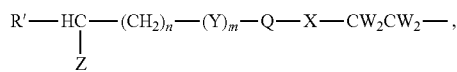

Formula III

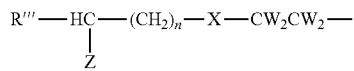

Formula IV where Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl; the alkyl is a $C_1$ to $C_{20}$ saturated or unsaturated alkyl or heteroalkaryl group, and the substituents can be of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

X, Y, Z, m, and n are as defined, and each W is, independently, hydrogen or a $C_1$ to $C_7$ alkyl; and R" is a moiety suitable for forming a bond between the compound of Formula III and a biologically-active compound or precursor thereof, and R''' is a moiety suitable for forming a bond between the compound of Formula IV and a biologically-active compound or precursor thereof.

In certain embodiments, R" and R''' can be the same as or different from R, and are chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

In other embodiments of the compound according to Formula XVI, the compound can have the structure according to Formula XIX:

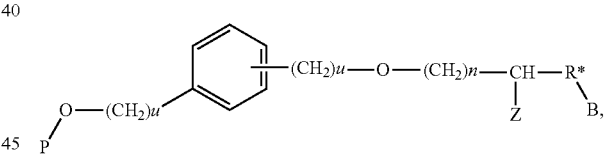

Formula XIX wherein P is a polyalkylene glycol polymer, each n and u are, independently, zero or an integer from one to five, Z is hydrogen, a straight- or branched-chain, saturated or unsaturated $C_1$ to $C_{20}$ alkyl or heteroalkyl group.

R* is a linking moiety formed from the reaction of R with a biologically-active compound or precursor thereof, and B is a biologically-active compound, or precursor thereof, after conjugation with R.

In one embodiment, V of Formula XIX is a methylene group and B is a biologically-active molecule having an amino group, where the methylene group forms a bond with the amino group on B.

In certain embodiments, the amine is the amino terminus of a peptide, an amine of an amino acid side chain of a peptide, or an amine of a glycosylation substituent of a glycosylated peptide. For example, the peptide can be an interferon, such as interferon-beta, e.g., interferon-beta-1a.

In another aspect, the invention relates to a composition according to Formula XX:

Formula XX

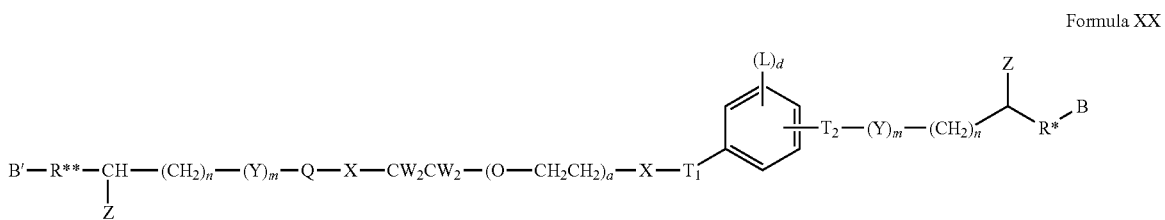

where m is 0 or 1, d is 0 or an integer from 1 to 4, a is an integer from 4 to 10,000, and n is 0 or an integer from 1 to 5.

Each X and Y is independently O, S, CO, $CO_2$, COS, SO, $SO_2$, CONR', $SO_2NR'$, or NR', or NR', $T_1$ and $T_2$ are, independently, absent, or a straight- or branched-chain, saturated or unsaturated $C_1$ to $C_{20}$ alkyl or heteroalkyl group, and each R' and Z is independently hydrogen, a straight- or branched-chain, saturated or unsaturated $C_1$ to $C_{20}$ alkyl or heteroalkyl group.

When present, each L is, independently, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents are selected from halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

Each W is, independently, hydrogen or a $C_1$ to $C_7$ alkyl.

R* and R** are, independently, linking moieties formed from the reaction of R and R'' with a biologically-active compound or precursor thereof, and B and B' are each a biologically-active compound, or precursor thereof, after conjugation with R and R'', respectively.

In some embodiments, B and B' are the same type of biologically-active compound. In other embodiments, B and B' are different biologically-active compounds. In still other embodiments, B and B' are the same biologically active molecule. In additional embodiments, R* and R** are the same. In other embodiments, R* and R** are different.

In another aspect, the invention relates to a composition according to Formula XXI:

Formula XXI

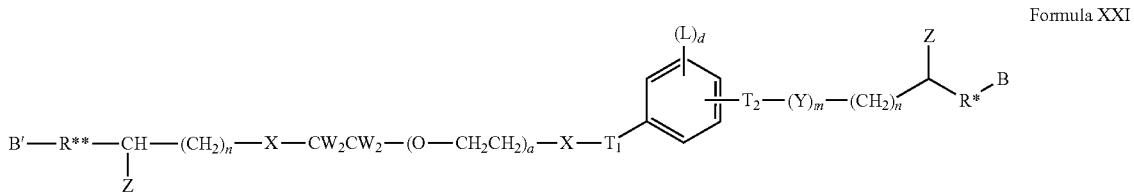

where m is 0 or 1, d is 0 or an integer from 1 to 4, a is an integer from 4 to 10,000, and n is 0 or an integer from 1 to 5.

X and Y are independently O, S, CO, $CO_2$, COS, SO, $SO_2$, CONR', $SO_2NR'$, or NR', $T_1$ and $T_2$ are, independently, absent, or a straight- or branched-chain, saturated or unsaturated $C_1$ to $C_{20}$ alkyl or heteroalkyl group, each R' and Z is, independently, hydrogen, a straight- or branched-chain, saturated or unsaturated $C_1$ to $C_{20}$ alkyl or heteroalkyl group.

When present, each L is, independently, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio, and each W is, independently, hydrogen or a $C_1$ to $C_7$ allyl.

R* and R** are, independently, linking moieties formed from the reaction of R and R'' with a biologically-active compound or precursor thereof, and B and B' are each a biologically-active compound, or precursor thereof, after conjugation with R and R'', respectively.

In some embodiments, B and B' are the same type of biologically-active compound. In other embodiments, B and B' are different biologically-active compounds. In still other embodiments, B and B' are the same biologically active molecule. In additional embodiments, R* and R** are the same. In other embodiments, R* and R** are different.

In another aspect, the invention involves a composition having the structure according to Formula XXII:

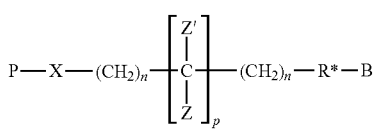

Formula XXII wherein P is a polyalkylene glycol polymer,

X is O, S, CO, CO$_2$, COS, SO, SO$_2$, CONR', SO$_2$NR', or NR';

R' is hydrogen, a straight- or branched-chain, saturated or unsaturated C$_1$ to C$_{20}$ alkyl or heteroalkyl group, C$_3$ to C$_8$ saturated or unsaturated cyclic alkyl or cyclic heteroalkyl, a Substituted or unsubstituted aryl or heteroaryl group or a substituted or unsubstituted alkaryl wherein the alkyl is a C$_1$ to C$_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

each Z and Z' is independently hydrogen, a straight- or branched-chain, saturated or unsaturated C$_1$ to C$_{20}$ alkyl or heteroalkyl group, C$_3$ to C$_8$ saturated or unsaturated cyclic alkyl or cyclic heteroalkyl, a substituted or unsubstituted aryl or heteroaryl group or a substituted or unsubstituted alkaryl wherein the alkyl is a C$_1$ to C$_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio, provided that at least one Z or Z' is not hydrogen;

R* is a linking moiety;

B is a biologically-active molecule;

each n is 0 or an integer from 1 to 5; and p is 1, 2, or 3.

In a further aspect, the invention involves a composition having the structure according to Formula XXIIa:

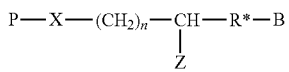

Formula XXIIa wherein P is a polyalkylene glycol polymer;

X is O, S, CO, CO$_2$, COS, SO, SO$_2$, CONR', SO$_2$NR', or NR'; and n is 0 or an integer from 1 to 5.

R' is hydrogen, a straight- or branched-chain, saturated or unsaturated C$_1$ to C$_{20}$ alkyl or heteroalkyl group, C$_3$ to C$_8$ saturated or unsaturated cyclic alkyl or cyclic heteroalkyl, a substituted or unsubstituted aryl or heteroaryl group or a substituted or unsubstituted alkaryl wherein the alkyl is a C$_1$ to C$_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

Z is a straight- or branched-chain, saturated or unsaturated C$_1$ to C$_{20}$ alkyl or heteroalkyl group, C$_3$ to C$_8$ saturated or unsaturated cyclic alkyl or cyclic heteroalkyl, a substituted or unsubstituted aryl or heteroaryl group or a substituted or unsubstituted alkaryl wherein the alkyl is a C$_1$ to C$_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

R* is a linking moiety formed from the reaction of R with a biologically-active compound or precursor thereof, and B is a biologically-active compound, or precursor thereof, after conjugation with R.

In one embodiment, R* is formed from the reaction of a moiety selected from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal with a biologically-active compound or precursor thereof.

In an additional embodiment, P is a polyethylene glycol having the structure of Formula II:

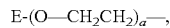

Formula II wherein E is hydrogen, a straight- or branched-chain C$_1$ to C$_{20}$ alkyl group, or a detectable label; and a is an integer from 4 to 10,000. In this embodiment, E may be methyl.

In another embodiment, P is a polyethylene glycol having the structure of Formula II:

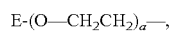

Formula II wherein E is a moiety suitable for forming a bond between the compound of Formula II and a biologically-active compound or precursor thereof and a is an integer from 4 to 10,000. In this embodiment, E may bind to a biologically-active compound or precursor thereof other than B. In other embodiments, E forms an additional bond to the biologically-active compound B.

In various embodiments, E may be selected from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In other embodiments, E has the structure according to Formula III:

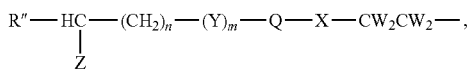

Formula III wherein P is a polyalkylene glycol polymer, each X and Y is independently O, S, CO, $CO_2$, COS, SO, $SO_2$, CONR', $SO_2$NR', or NR';

Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

R' and each Z are independently as described above;

m is 0 or 1;

each n is independently 0 or an integer from 1 to 5;

R" is a moiety suitable for forming a bond between the compound of Formula III and a biologically-active compound or precursor thereof; and each W is, independently, hydrogen or a $C_1$ to $C_7$ alkyl.

In a further embodiment, E has the structure according to Formula IV:

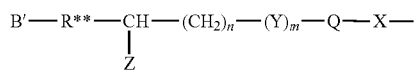

Formula IV wherein each X, Z and n are, independently, as defined;

each W is, independently, hydrogen or a $C_1$ to $C_7$ alkyl; and

R'" is a moiety suitable for forming a bond between the compound of Formula IV and a biologically-active compound or precursor thereof.

In still further embodiments, R" is chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In yet other embodiments, R'" is chosen from the group consisting of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal.

In additional embodiments, E is a detectable label. For example, E may be selected from the group consisting of radioactive isotopes, fluorescent moieties, phosphorescent moieties, chemiluminescent moieties and quantum dots.

In another embodiment, R* is methylene and B is a biologically-active molecule attached via an amine. For example, the amine is the amino terminus of a peptide. In a further embodiment, the peptide is an interferon such as interferon-beta-1a.

In another embodiment, the invention is a composition having the structure according to Formula XXIII:

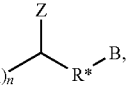

Formula XXIII wherein n, a, R* B, and Z are as defined above. In one additional embodiment, Z is methyl and n is one.

In still a further aspect, the invention involves a composition according to Formula XXIV:

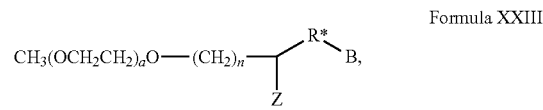

Formula XXIV wherein m is 0 or 1, a is an integer from 4 to 10,000; and each n is independently zero or an integer from 1 to 5. Each X and Y is independently O, S, CO, $CO_2$, COS, SO, $SO_2$, CONR', $SO_2$NR', or NR'; each R' and Z is, independently, hydrogen, a straight- or branched-chain, saturated or unsaturated $C_1$ to $C_{20}$ alkyl or heteroalkyl group; and each W is, independently, hydrogen or a $C_1$ to $C_7$ alkyl.

Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

R* and R** are, independently, linking moieties formed from the reaction of R and R" with a biologically-active compound or precursor thereof, and B and B' are each a biologically-active compound, or precursor thereof, after conjugation with R and R", respectively.

In some embodiments, B and B' are the same type of biologically-active compound. In other embodiments, B and B' are different biologically-active compounds. In still other embodiments, B and B' are the same biologically active molecule. In additional embodiments, R* and R** are the same. In other embodiments, R* and R** are different.

In a further aspect, the invention involves a composition according to Formula XXV:

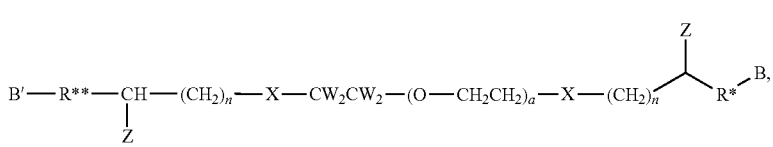

Formula XXV wherein

X is O, S, CO, CO$_2$, COS, SO, SO$_2$, CONR', SO$_2$NR', or NR'; a is an integer from 4 to 10,000; and each n is independently 0 or an integer from 1 to 5.

Each and Z is independently hydrogen, a straight- or branched-chain, saturated or unsaturated C$_1$ to C$_{20}$ alkyl or heteroalkyl group, and each W is, independently, hydrogen or a C$_1$ to C$_7$ alkyl.

R* and R** are, independently, linking moieties formed from the reaction of R and R" with a biologically-active compound or precursor thereof, and B and B' are each a biologically-active compound, or precursor thereof, after conjugation with R and R", respectively.

In some embodiments, B and B' are the same type of biologically-active compound. In other embodiments, B and B' are different biologically-active compounds. In still other embodiments, B and B' are the same biologically active molecule. In additional embodiments, R* and R** are the same. In other embodiments, R* and R** are different.

The invention also involves a pharmaceutical composition containing the compositions of the invention along with a pharmaceutically-acceptable carrier. In various embodiments, the pharmaceutical composition also contains an additional biologically-active agent. For example, the biologically-active agent may be selected from the group consisting of a peptide, peptide analog, protein, enzyme, small molecule, dye, lipid, nucleoside, oligonucleotide, oligonucleotide analog, sugar, oligosaccharide, cell, virus, liposome, microparticle, surface, and a micelle. In another embodiment, the biologically-active agent is an antiviral agent.

In another aspect, the invention relates to a composition comprising the product of the reaction of the compound of Formula I and a biologically-active compound or a precursor thereof (B).

In one embodiment, the composition has the structure according to Formula XIV:

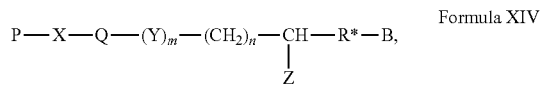

Formula XIV where all variables are as defined above, and R* is a linking moiety formed by the reaction of R with a reactive moiety on the biologically-active compound or precursor thereof; and B is a biologically-active compound or precursor thereof.

In another aspect, the invention relates to a composition comprising the product of the reaction of the compound of Formula V and a biologically-active compound or a precursor thereof. In one embodiment, the composition has the structure according to Formula XV:

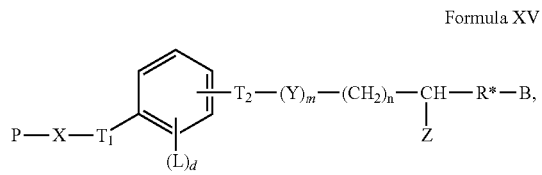

Formula XV where all variables are as defined above, R* is a linking moiety formed by the reaction of R with a reactive moiety on the biologically-active compound or precursor thereof; and B is a biologically-active compound or precursor thereof.

In yet another embodiment, the composition has the structure according to Formula XX or XXI:

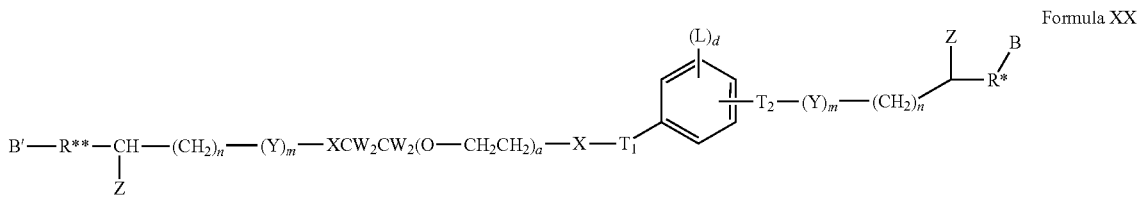

Formula XX

-continued

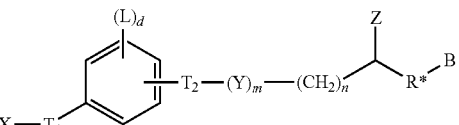
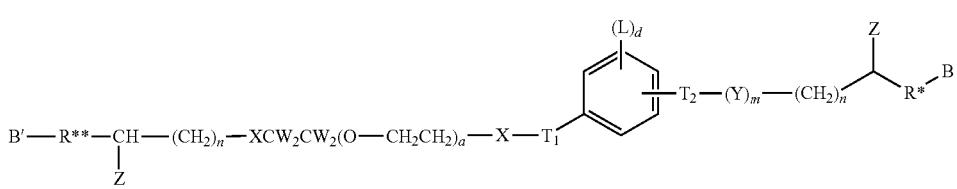

where all variables are as defined above, each W is, independently, hydrogen or a $C_1$ to $C_7$ alkyl, R* is a linking moiety formed by the reaction of R with a reactive moiety on the biologically-active compound, B, or precursor thereof; R** is a linking moiety formed by the reaction of R" or R'" with a reactive moiety on the biologically-active compound, B', or precursor thereof; and B and B' are, independently, a biologically-active compound or precursor thereof. In some embodiments, B and B' are the same type of biologically-active compound. In other embodiments, B and B' are different biologically-active compounds. In still other embodiments, B and B' are the same biologically active molecule. In additional embodiments, R* and R** are the same. In other embodiments, R* and R** are different.

In another aspect, the invention relates to a composition comprising the product of the reaction of the compound Formula VI and a biologically-active compound or a precursor thereof.

In one embodiment; the composition has the structure according to Formula XVI:

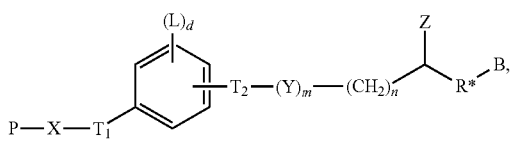

where all variables are as defined above, R* is a linking moiety formed by the reaction of R with a reactive moiety on the biologically-active compound or precursor thereof; and B is a biologically-active compound or precursor thereof.

In another aspect, the invention relates to a composition comprising the product of the reaction of the compound of Formula VII and a biologically-active compound or a precursor thereof.

In one embodiment, the composition has the structure according to Formula XVII:

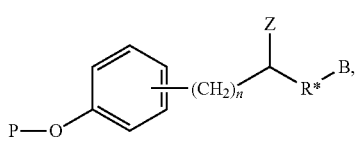

where all variables are as defined above, R* is a linking moiety formed by the reaction of R with a reactive moiety on the biologically-active compound or precursor thereof; and B is a biologically-active compound or precursor thereof.

In another aspect, the invention relates to a composition comprising the product of the reaction of the compound of Formula VIII and a biologically-active compound or a precursor thereof.

In one embodiment, the composition has the structure according to Formula XVIII:

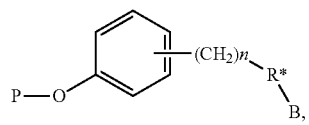

where all variables are as defined above, R* is a linking moiety formed by the reaction of R with a reactive moiety on the biologically-active compound or precursor thereof; and B is a biologically-active compound or precursor thereof.

In another aspect, the invention relates to a composition comprising the product of the reaction of the compound of Formula IX and a biologically-active compound or a precursor thereof.

In one embodiment, the composition has the structure according to Formula XIX:

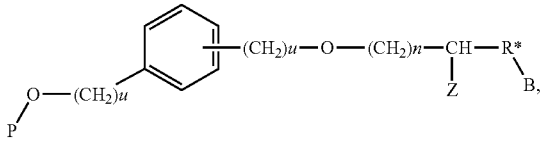

where all variables are as defined above, R* is a linking moiety formed by the reaction of R with a reactive moiety on the biologically-active compound or precursor thereof; and B is a biologically-active compound or precursor thereof.

In another aspect, the invention relates to a composition comprising the product of the reaction of the compound of Formula X and a biologically-active compound or a precursor thereof.

In one embodiment, the composition has the structure according to Formula XXII:

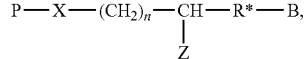

where all variables are as defined above, R* is a linking moiety formed by the reaction of R with a reactive moiety on the biologically-active compound or precursor thereof; and B is a biologically-active compound or precursor thereof.

In another embodiment, the composition has the structure the structure according to Formula XXIV:

Formula XXIV $$B'-R^{**}-\underset{\underset{Z}{|}}{CH}-(CH_2)_n-(Y)_m-Q-X-CW_2CW_2-(O-CH_2CH_2)_a-X-(CH_2)_n-\overset{\overset{Z}{|}}{\underset{R^*}{C}}-B,$$

where all variables are as defined above, each W is, independently, hydrogen or a $C_1$ to $C_7$ alkyl. $R^*$ is a linking moiety formed by the reaction of R with a reactive moiety on the biologically-active compound, B, or precursor thereof, $R^{**}$ is a linking moiety formed by the reaction of R" with a reactive moiety on the biologically-active compound, B', or precursor thereof; and B and B' are, independently, a biologically-active compound or precursor thereof. In some embodiments, B and B' are the same type of biologically-active compound. In other embodiments, B and B' are different biologically-active compounds. In still other embodiments, B and B' are the same biologically active molecule. In additional embodiments, $R^*$ and $R^{**}$ are the same. In other embodiments, $R^*$ and $R^{**}$ are different.

In other embodiments, the composition has the structure according to Formula XXV:

clic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

each R', Z and Z' is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl Formula XXV $$B'-R^{**}-\underset{\underset{Z}{|}}{CH}-(CH_2)_n-X-CW_2CW_2-(O-CH_2CH_2)_n-X-(CH_2)_n-\overset{\overset{Z}{|}}{\underset{R^*}{C}}-B,$$

where all variables are as defined in claims above, each W is, independently, hydrogen or a $C_1$ to $C_7$ alkyl.

$R^*$ and $R^{**}$ are, independently, linking moieties formed from the reaction of R and R" with a biologically-active compound or precursor thereof, and B and B' are each a biologically-active compound, or precursor thereof, after conjugation with R and R", respectively.

In some embodiments, B and B' are the same type of biologically-active compound. In other embodiments, B and B' are different biologically-active compounds. In still other embodiments, B and B' are the same biologically active molecule. In additional embodiments, $R^*$ and $R^{**}$ are the same. In other embodiments, $R^*$ and $R^{**}$ are different.

In another aspect, the invention involves a method of treating a patient with a susceptible viral infection, comprising administering to the patient an effective amount of a composition having the structure according to Formula XIV:

wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

$R^*$ is a linking moiety;

B is a biologically-active compound or precursor thereof;

m is 0 or 1;

each n is 0 or an integer from 1 to 5; and p is 1, 2, or 3.

In a further aspect, the invention involves a method of treating a patient with a susceptible viral infection by administering to the patient an effective amount of a composition having the structure according to Formula XIVa:

Formula XIV $$P-X-(CH_2)_n-Q-(Y)_m-(CH_2)_n-\left[\underset{\underset{Z}{|}}{\overset{\overset{Z'}{|}}{C}}\right]_p-(CH_2)_n-R^*-B,$$

Formula XIVa $$P-X-Q-(Y)_m-(CH_2)_n-\underset{\underset{Z}{|}}{CH}-R^*-B,$$

wherein P is a polyalkylene glycol polymer, m is 0 or 1; and n is 0 or an integer from 1 to 5.

X and Y are independently O, S, CO, $CO_2$, COS, SO, $SO_2$, CONR', $SO_2NR'$, or NR'; and Q is a $C_3$ to $C_8$ saturated or unsaturated cyclic alkyl or cyclic heteroalkyl (including fused bicyclic and bridged bicyclic ring structures), a substituted or wherein P is a polyalkylene glycol polymer, X and Y are independently O, S, CO, $CO_2$, COS, SO, $SO_2$, CONR', $SO_2NR'$, or NR';

Q is a $C_3$ to $C_8$ saturated or unsaturated cyclic alkyl or cyclic heteroalkyl (including fused bicyclic and bridged bicyunsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

Each R' and Z is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

R* is a linking moiety formed from the reaction of R with a biologically-active compound or precursor thereof, and B is a biologically-active compound, or precursor thereof, after conjugation with R.

In one embodiment, B is a biologically-active peptide such as interferon. For example, this interferon may be interferon-beta-1a.

In further embodiments, the composition also includes a biologically-active agent selected from the group consisting of a small molecule antiviral, a nucleic acid antiviral and a peptidic antiviral. For example, the antiviral agent may be selected from the group consisting of ribavirin, levovirin, 3TC, FTC, MB686, zidovudine, acyclovir, gancyclovir, viramide, VX-497, VX-950, and ISIS-14803.

In various embodiments, the viral infection in need of treatment is chronic hepatitis C.

In an additional aspect, the invention involves a method of treating a patient with a susceptible viral infection by administering to the patient an effective amount of a composition having the structure according to Formula XV:

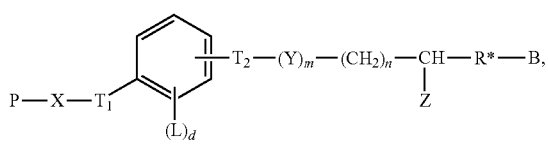

Formula XV wherein P is a polyalkylene glycol polymer, m is 0 or 1; d is 0 or an integer from 1 to 4; n is 0 or an integer from 1 to 5; and X and Y are independently O, S, CO, $CO_2$, COS, SO, $SO_2$, CONR', $SO_2NR'$, or NR'.

$T_1$ and $T_2$ are, independently, absent, or a straight- or branched-chain, saturated or unsaturated $C_1$ to $C_{20}$ alkyl or heteroalkyl group, a $C_3$ to $C_8$ saturated or unsaturated cyclic alkyl or cyclic heteroalkyl, a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

Each R' and Z is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

Each L is, independently, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

R* is a linking moiety formed from the reaction of R with a biologically-active compound or precursor thereof, and B is a biologically-active compound, or precursor thereof, after conjugation with R.

In various embodiments, B is a biologically-active peptide such as interferon. For example, in one embodiment, B is interferon-beta-1a.

In another embodiment, the composition further contains a biologically-active agent selected from the group consisting of a small molecule antiviral, a nucleic acid antiviral and a peptidic antiviral. In other embodiments, the antiviral agent may be selected from the group consisting of ribavirin, levovirin, 3TC, FTC, MB686, zidovudine, acyclovir, gancyclovir, viramide, VX-497, VX-950, and ISIS-14803. In addition, the viral infection can be chronic hepatitis C.

In a further aspect, the invention involves a method of treating a patient with a susceptible viral infection by administering to the patient an effective amount of a composition having the structure according to Formula XVI:

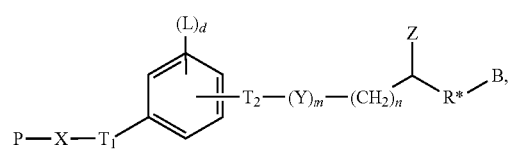

Formula XVI where P is a polyalkylene glycol polymer, m is 0 or 1; d is 0 or an integer from 1 to 4; n is 0 or an integer from 1 to 5; X and Y are independently O, S, CO, $CO_2$, COS, SO, $SO_2$, CONR', $SO_2NR'$, or NR'; $T_1$ and $T_2$ are, independently, absent, or a straight- or branched-chain, saturated or unsaturated $C_1$ to $C_{20}$ alkyl or heteroalkyl group; and each R' and Z is independently hydrogen, a straight- or branched-chain, saturated or unsaturated $C_1$ to $C_{20}$ alkyl or heteroalkyl group.

Each L is, independently, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

R* is a linking moiety formed from the reaction of R with a biologically-active compound or precursor thereof, and B is a biologically-active compound, or precursor thereof, after conjugation with R.

In various embodiments, B is a biologically-active peptide such as interferon. For example, B may be interferon-beta-1a.

In still further embodiments, the composition further contains a biologically-active agent selected from the group consisting of a small molecule antiviral, a nucleic acid antiviral and a peptidic antiviral. For example, the antiviral agent may be selected from the group consisting of ribavirin, levovirin, 3TC, FTC, MB686, zidovudine acyclovir, gancyclovir, viramide, VX-497, VX-950, and ISIS-14803.

In another embodiment, the viral infection is chronic hepatitis C.

In a further aspect, the invention involves a method of treating a patient with a susceptible viral infection by administering to the patient an effective amount of a composition having the structure according to Formula XX:

$C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

R* and R** are, independently, linking moieties formed from the reaction of R and R'' with a biologically-active compound or precursor thereof, and B and B' are each a biologically-active compound, or precursor thereof, after conjugation with R and R'', respectively.

In some embodiments, B and B' are the same type of biologically-active compound. In other embodiments, B and B' are different biologically-active compounds. In still other embodiments, B and B' are the same biologically active molecule. In additional embodiments, R* and R** are the same. In other embodiments, R* and R** are different.

In various embodiments, B is a biologically-active peptide such as interferon. For example, in one embodiment, B is interferon-beta-1a.

In other embodiments, the composition further contains a biologically-active agent selected from the group consisting Formula XX

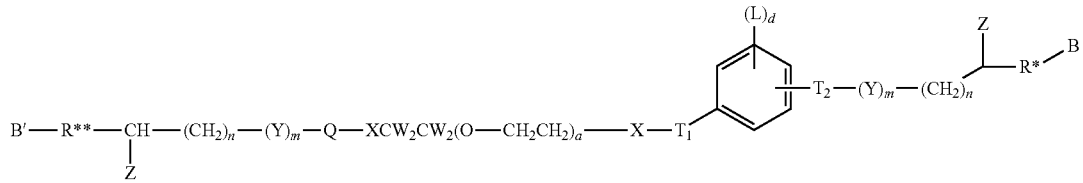

wherein m is 0 or 1; d is 0 or an integer from 1 to 4; a is an integer from 4 to 10,000; and n is 0 or an integer from 1 to 5.

Each X and Y is independently O, S, CO, $CO_2$, COS, SO, $SO_2$, CONR', $SO_2NR'$, or NR'; $T_1$ and $T_2$ are, independently, absent, or a straight- or branched-chain, saturated or unsaturated $C_1$ to $C_{20}$ alkyl or heteroalkyl group; each R' and Z is independently hydrogen, a straight- or branched-chain, saturated or unsaturated $C_1$ to $C_{20}$ alkyl or heteroalkyl group; and each W is, independently, hydrogen or a $C_1$ to $C_7$ alkyl.

Each L is, independently, a straight- or branched-chain, saturated or unsaturated $C_1$ to $C_{20}$ alkyl or heteroalkyl group, of a small molecule antiviral, a nucleic acid antiviral and a peptidic antiviral. For example, the antiviral agent may be selected from the group consisting of ribavirin, levovirin, 3TC, FTC, MB686, zidovudine, acyclovir, gancyclovir, viramide, VX-497, VX-950, and ISIS-14803.

In a further embodiment, the viral infection is chronic hepatitis C.

In a further aspect, the invention involves a method of treating a patient with a susceptible viral infection by administering to the patient an effective amount of a composition having the structure according to Formula XXI:

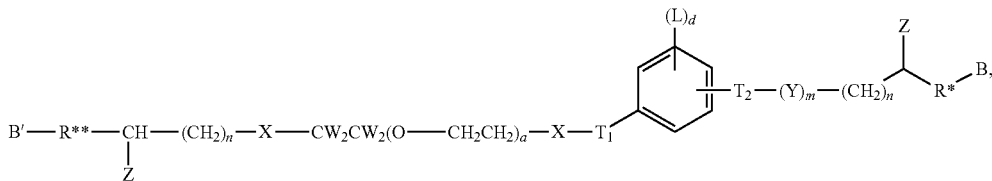

Formula XXI

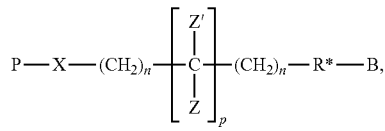

Formula XXII where m is 0 or 1; d is 0 or an integer from 1 to 4; a is an integer from 4 to 10,000; each n is 0 or an integer from 1 to 5; each X and Y is independently O, S, CO, $CO_2$, COS, SO, $SO_2$, CONR', $SO_2$NR', or NR'; $T_1$ and $T_2$ are, independently, absent, or a straight- or branched-chain, saturated or unsaturated $C_1$ to $C_{20}$ alkyl or heteroalkyl group; each R' and Z is independently hydrogen, a straight- or branched-chain, saturated or unsaturated $C_1$ to $C_{20}$ alkyl or heteroalkyl group; and each W is, independently, hydrogen or a $C_1$ to $C_7$ alkyl.

Each L is, independently, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

R* and R** are, independently, linking moieties formed from the reaction of R and R" with a biologically-active compound or precursor thereof, and B and B' are each a biologically-active compound, or precursor thereof, after conjugation with R and R", respectively.

In some embodiments, B and B' are the same type of biologically-active compound. In other embodiments, B and B' are different biologically-active compounds. In still other embodiments, B and B' are the same biologically active molecule. In additional embodiments, R* and R** are the same. In other embodiments, R* and R** are different.

In various embodiments, B is a biologically-active peptide such as an interferon. For example, B may be is interferon-beta-1a.

In another embodiment, the composition further contains a biologically-active agent selected from the group consisting of a small molecule antiviral, a nucleic acid antiviral and a peptidic antiviral. For example, the antiviral agent may be selected from the group consisting of ribavirin, levovirin, 3TC, FTC, MB686, zidovudine, acyclovir, gancyclovir, viramide, VX-497, VX-950, and ISIS-14803.

In a further embodiment, the viral infection is chronic hepatitis C.

In another aspect, the invention involves a method of treating a patient with a susceptible viral infection, comprising administering to the patient an effective amount of a composition having the structure according to Formula XXII:

wherein

P is a polyalkylene glycol polymer,

X is O, S, CO, $CO_2$, COS, SO, $SO_2$, CONR', $SO_2$NR', or NR';

R' is hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

each Z and Z' is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio provided that at least one Z or Z' is not hydrogen;

R* is a linking moiety;

B is a biologically-active molecule.

m is 0 or 1;

each n is 0 or an integer from 1 to 5; and p is 1, 2, or 3.

In still another aspect, the invention involves a method of treating a patient with a susceptible viral infection, comprising administering to the patient an effective amount of a composition having the structure according to Formula XXIIa:

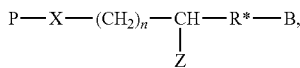

Formula XXIIa where: P is a polyalkylene glycol polymer; m is 0 or 1; n is 0 or an integer from 1 to 5; X is O, S, CO, CO$_2$, COS, SO, SO$_2$, CONR', SO$_2$NR', or NR'; and R' is hydrogen, a straight- or branched-chain, saturated or unsaturated C$_1$ to C$_{20}$ alkyl or heteroalkyl group, C$_3$ to C$_8$ saturated or unsaturated cyclic alkyl or cyclic heteroalkyl, a substituted or unsubstituted aryl or heteroaryl group or a substituted or unsubstituted alkaryl wherein the alkyl is a C$_1$ to C$_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

Z is a straight- or branched-chain, saturated or unsaturated C$_1$ to C$_{20}$ alkyl or heteroalkyl group, C$_3$ to C$_8$ saturated or unsaturated cyclic alkyl or cyclic heteroalkyl, a substituted or unsubstituted aryl or heteroaryl group or a substituted or unsubstituted alkaryl wherein the alkyl is a C$_1$ to C$_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

R* is a linking moiety formed from the reaction of R with a biologically-active compound or precursor thereof, and B is a biologically-active compound, or precursor thereof, after conjugation with R.

In various embodiments, B is a biologically-active peptide such as interferon. For example, B may be interferon-beta-1a.

In another embodiment, the composition further contains a biologically-active agent selected from the group consisting of a small molecule antiviral, a nucleic acid antiviral and a peptidic antiviral. For example, the antiviral agent may be selected from the group consisting of ribavirin, levovirin, 3TC, FTC, MB686, zidovudine, acyclovir, gancyclovir, viramide, VX-497, VX-950, and ISIS-14803.

In a further embodiment, the viral infection is chronic hepatitis C.

In yet another aspect, the invention involves a method of treating a patient with a susceptible viral infection by administering to the patient an effective amount of a composition having the structure according to Formula XXIV:

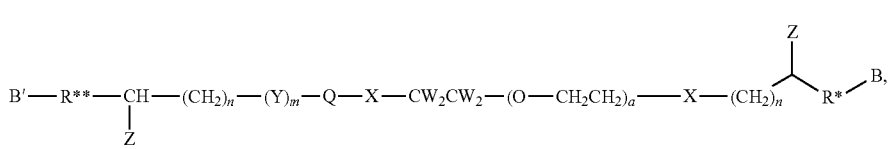

Formula XXIV where: m is 0 or 1; a is an integer from 4 to 10,000; each n is independently 0 or an integer from 1 to 5; each X and Y is independently O, S, CO, CO$_2$, COS, SO, SO$_2$, CONR', SO$_2$NR', or NR'; each R' and Z is independently hydrogen, a straight- or branched-chain, saturated or unsaturated C$_1$ to C$_{20}$ alkyl or heteroalkyl group; and each W is, independently, hydrogen or a C$_1$ to C$_7$ alkyl.

Q is a C$_3$ to C$_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a C$_1$ to C$_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio.

R* and R** are, independently, linking moieties formed from the reaction of R and R" with a biologically-active compound or precursor thereof, and B and B' are each a biologically-active compound, or precursor thereof, after conjugation with R and R", respectively.

In some embodiments, B and B' are the same type of biologically-active compound. In other embodiments, B and B' are different biologically-active compounds. In still other embodiments, B and B' are the same biologically active molecule. In additional embodiments, R.* and R** are the same. In other embodiments, R* and R** are different.

In various embodiments, B is a biologically-active peptide such as interferon. For example, B may be interferon-beta-1a.

In other embodiments, the composition further contains a biologically-active agent selected from the group consisting of a small molecule antiviral, a nucleic acid antiviral and a peptidic antiviral. For example, the antiviral agent may be selected from the group consisting of ribavirin, levovirin, 3TC, FTC, MB686, zidovudine, acyclovir, gancyclovir, viramide, VX-497, VX-950, and ISIS-14803.

In still other embodiments, the viral infection is chronic hepatitis C.

In an additional aspect, the invention involves a method of treating a patient with a susceptible viral infection by administering to the patient an effective amount of a composition having the structure according to Formula XXV:

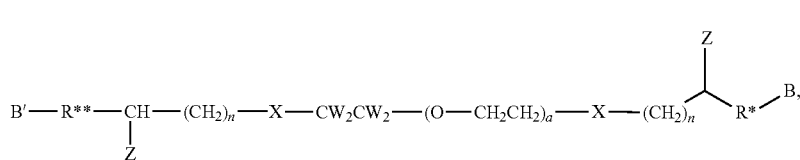

Formula XXV wherein each W is, independently, hydrogen or a $C_1$ to $C_7$ alkyl; a is an integer from 4 to 10,000; each n is independently 0 or an integer from 1 to 5; X is O, S, CO, $CO_2$, COS, SO, $SO_2$, CONR', $SO_2NR'$, or NR'; and each and Z is independently hydrogen, a straight- or branched-chain, saturated or unsaturated $C_1$ to $C_{20}$ alkyl or heteroalkyl group.

R* and R** are, independently, linking moieties formed from the reaction of R and R" with a biologically-active compound or precursor thereof, and B and B' are each a biologically-active compound, or precursor thereof, after conjugation with R and R", respectively.

In some embodiments, B and B' are the same type of biologically-active compound. In other embodiments, B and B' are different biologically-active compounds. In still other embodiments, B and B' are the same biologically active molecule. In additional embodiments, R* and R** are the same. In other embodiments, R* and R** are different.

In various embodiments, B is a biologically-active peptide such as interferon. For example, B may be interferon-beta-1a.

In another embodiment, the composition further contains a biologically-active agent selected from the group consisting of a small molecule antiviral, a nucleic acid antiviral and a peptidic antiviral. For example, the antiviral agent may be selected from the group consisting of ribavirin, levovirin, 3TC, FTC, MB686, zidovudine, acyclovir, gancyclovir, viramide, VX-497, VX-950, and ISIS-14803.

In still other embodiments, the viral infection is chronic hepatitis C.

The present invention is also concerned with a method of treating a patient suspected of having hepatitis C infection by administering to the patient a combination of any of the compositions of the invention and an antiviral agent. In various embodiments, the composition and the antiviral agent are administered simultaneously, sequentially, or alternatively.

In one embodiment, the antiviral agent is ribavirin.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

The present invention will be further understood from the following description with reference to the tables, in which:

FIG. 1 is a reducing SDS-PAGE gel showing the purity of unmodified IFN-β-1a and 20 kDa mPEG-O-2-methylpropionaldehyde-modified IFN-β-1a: Lane A: molecular weight markers (from top to bottom; 100 kDa, 68 kDa, 45 kDa, 27 kDa, and 18 kDa, respectively); Lane B: 4 μg of unmodified IFN-β-1a; Lane C: 4 μg of 20 kDa mPEG-O-2-methylpropionaldehyde-modified IFN-β-1a.

FIG. 2 depicts traces of the size exclusion chromatography of unmodified IFN-β-1a and 20 kDa mPEG-O-2-methylpropionaldehyde-modified IFN-β-1a: Panel A: molecular weight standards; Panel B: 20 kDa mPEG-O-2-methylpropionaldehyde-modified IFN-β-1a; Panel C, unmodified IFN-β-1a.

FIG. 3 is a trace of the size exclusion chromatography of 20 kDa mPEG-O-m-methylphenyl-O-2-methylpropionaldehyde-modified IFN-β-1a.

FIG. 5 depicts traces of the size exclusion chromatography of 20 kDa mPEG-O-p-phenylacetaldehyde-modified IFN-β-1a; Panel A: molecular weight standards; Panel B: 20 kDa mPEG-O-p-phenylacetaldehyde-modified IFN-β-1a.

FIG. 7A; unmodified IFN-β-1a (o), 20 kDa mPEG-O-2-methylpropionaldehyde-modified IFN-β-1a (□), 20 kDa mPEG-O-p-methylphenyl-O-2-methylpropionaldehyde-modified IFN-β-1a (Δ), and 20 kDa mPEG-O-m-methylphenyl-O-2-methylpropionaldehyde-modified (◊). FIG. 7B; unmodified IFN-β-1a (o), 20 kDa mPEG-O-p-phenylacetaldehyde-modified IFN-β-1a (□), 20 kDa mPEG-O-p-phenylpropionaldehyde-modified IFN-β-1a (Δ), and 20 kDa mPEG-O-m-phenylacetaldehyde-modified IFN-β-1a (◊).

FIG. 8A: Unmodified IFN-β-1a (upper panel) and IFN-13-1a modified with 20 kDa mPEG-O-2-methylpropionaldehyde (lower panel); FIG. 8B: IFN-13-1a modified with 20 kDa mPEG-O-p-methylphenyl-O-2-methylpropionaldehyde (upper panel) and 20 kDa mPEG-O-p-phenylacetaldehyde (lower panel).

FIG. 9A: Unmodified IFN-β-1a (upper panel) and IFN-β-1a modified with 20 kDa mPEG-O-p-phenylpropionaldehyde (lower panel); FIG. 9B: IFN-β-1a modified with 20 kDa mPEG-O-m-phenylacetaldehyde (upper panel) and 20 kDa mPEG-O-m-methylphenyl-O-2-methylpropionaldehyde (lower panel).

DETAILED DESCRIPTION OF THE INVENTION

Figure 1:
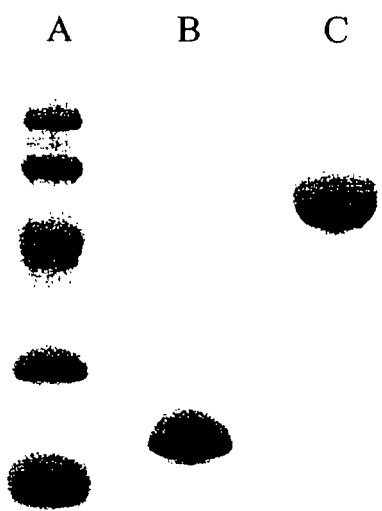

The invention is directed to compounds and methods useful in the treatment of various diseases and disorders. As explained in detail below, such diseases and disorders include, in particular, those which are susceptible to treatment with interferon therapy, including but not limited to viral infections such as hepatitis infections and autoimmune diseases such as multiple sclerosis.

The compounds of the invention include novel, activated polyalkylene glycol compounds according to Formula I:

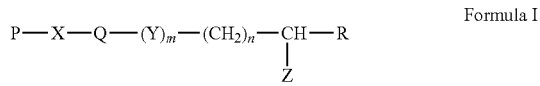

Formula I where P is a water soluble polymer such as a polyalkylene glycol polymer. A non-limiting list of such polymers include other polyalkylene oxide homopolymers such as polypropylene glycols, polyoxyethylenated polyols, copolymers thereof and block copolymers thereof. Other examples of suitable water-soluble and non-peptidic polymer backbones include poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, and mixtures thereof. In one embodiment, the polymer backbone is poly(ethylene glycol) or monomethoxy polyethylene glycol (mPEG) having an average molecular weight from about 200 Da to about 400,000 Da. It should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multi-armed PEG, forked PEG, branched PEG, pendent PEG, or PEG with degradable linkages therein.

In the class of compounds represented by Formula I, there are between zero and five methylene groups between Y and the Z-containing carbon (e.g., n is zero or an integer from one to five) and m is zero or one, e.g., Y is present or absent.

X and Y are, independently, O, S, CO, CO$_2$, COS, SO, SO$_2$, CONR', SO$_2$NR', or NR'. In some embodiments, X and Y are oxygen.

Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonamido, sulfonyl, heterocyclyl, aralkyl, aromatic moiety, heteroaromatic moiety, imino, sulfamoyl, sulfonate, silyl, ether, or alkylthio.

The Z substituent is hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, sulfamoyl, sulfonate, silyl, ether, or alkylthio.

When X or Y is NR', R' can be hydrogen, a straight- or branched-chain, saturated or unsaturated $C_1$ to $C_{20}$ alkyl or heteroalkyl group, a $C_3$ to $C_8$ saturated or unsaturated cyclic alkyl or cyclic heteroalkyl, a substituted or unsubstituted aryl or heteroaryl group or a substituted or unsubstituted alkaryl, wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, sulfamoyl, sulfonate, silyl, ether, or alkylthio.

R is a reactive functional group, i.e., an activating moiety capable of reacting to form a linkage or a bond between the compound of Formula I and a biologically-active compound or precursor thereof. Thus, R represents the "activating group" of the activated polyalkylene glycol compounds (PGCs) represented by Formula I. R can be, for example, a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal. In particular embodiments, R is an aldehyde hydrate.

Specific examples of R in the literature include N-succinimidyl carbonate (see e.g., U.S. Pat. Nos. 5,281,698, 5,468,478), amine (see e.g., Buckmann et al. Makromol. Chem. 182:1379 (1981), Zaplipsky et al. *Eur. Polym. J.* 19:1177 (1983)), hydrazide (See, e.g., Andresz et al. *Makromol. Chem.* 179:301 (1978)), succinimidyl propionate and succinimidyl butanoate (see, e.g. Olson et al. in *Poly(ethylene glycol) Chemistry & Biological Applications*, pp 170-181, Harris & Zaplipsky Eds., ACS, Washington, D.C., 1997; see also U.S. Pat. No. 5,672,662), succinimidyl succinate (See. e.g., Abuchowski et al. *Cancer Biochem. Biophys.* 7:175 (1984) and Joppich et al. *Macrolol. Chem.* 180:1381 (1979), succinimidyl ester (see, e.g., U.S. Pat. No. 4,670,417), benzotriazole carbonate (see, e.g., U.S. Pat. No. 5 5,650,234), glycidyl ether (see, e.g., Pitha et al. *Eur. J. Biochem.* 94:11 (1979), Elling et al., *Biotech. Appl. Biochem.* 13:354 (1991), oxycarbonylimidazole (see, e.g. Beauchamp, et al., *Anal. Biochem.* 131:25 (1983). Tondelli et al. *J. Controlled Release* 1:251 (1985)), p-nitrophenyl carbonate (see, e.g., Veronese, et al., *Appl. Biochem. Biotech.,* 11:141 (1985); and Sartore et al., *Appl. Biochem. Biotech.* 27:45 10 (1991)), aldehyde (see, e.g., Harris et al. *J. Polym. Sci. Chem. Ed.* 22:341 (1984), U.S. Pat. No. 5,824,784, U.S. Pat. No. 5,252,714), maleimide (see, e.g., Goodson et al. Bio/Technology 8:343 (1990), Romani et al. in *Chemistry of Peptides and Proteins* 2:29 (1984)), and Kogan, *Synthetic Comm.* 22:2417 (1992)), orthopyridyl-disulfide (see, e.g., Woghiren, et al. *Bioconj. Chem.* 4:314 (1993)), acrylol (see, e.g., Sawhney 15 et al., Macromolecules, 26:581 (1993)), vinylsulfone (see, e.g., U.S. Pat. No. 5,900,461). In addition, two molecules of the polymer of this invention can also be linked to the amino acid lysine to form a di-substituted lysine, which can then be further activated with N-hydroxysuccinimide to form an active N-succinimidyl moiety (see, e.g., U.S. Pat. No. 5,932,462).

The terms "functional group", "active moiety", "active group", "activating group", "activating moiety", "reactive site", "chemically-reactive group" and" chemically-reactive moiety" are used in the art and herein to refer to distinct, definable portions or units of a molecule. The terms are somewhat synonymous in the chemical arts and are used herein to indicate the portions of molecules having a characteristic chemical activity and which are typically reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions in order to react. For example, as would be understood in the art, the term "active ester" would include those esters that react readily with nucleophilic groups such as amines. Typically, an active ester will react with an amine in aqueous medium in a matter of minutes, whereas certain esters, such as methyl or ethyl esters, require a strong catalyst in order to react with a nucleophilic group.

In the compounds of the invention as defined above, the functional group R becomes a linking moiety, R*, after it has reacted with a biologically-active molecule to form a linkage or bond between the activated polyalkylene glycol compound (PGC) and the biologically-active compound. Thus, B is a biologically-active compound after conjugation to the PGC and R* is a moiety formed by the reaction of R on the activated PGC with one or more reactive functional groups on the biologically-active compound, B, such that a single covalent attachment results between the PGC and biologically-active compound. In a preferred embodiment, R* is a moiety formed by the reaction of R on the activated PGC with a single reactive functional group on the biologically-active compound, such that a covalent attachment results between the activated polyalkylene glycol compound (PGC) and the biologically-active compound.

The biologically-active compound or precursor thereof (B) is preferably not adversely affected by the presence of the PGC. Additionally, B either naturally has a functional group which is able to react with and form a linkage with the activated PGC, or is modified to contain such a reactive group.

As used herein, a precursor of B is an inactive or less active form of B that changes to the active or more active form, respectively, upon contact with physiological conditions, e.g., administration to a subject. Such changes can be conformational or structural changes, including, but not limited to, changing from a protected form to a non-protected form of B. As used herein, such change does not include release of the conjugated PGCs of this invention.

As would be understood in the art, the term "protected" refers to the presence of a protecting group or moiety that prevents reaction of the chemically-reactive functional group under certain reaction conditions. The protecting group will vary depending on the type of chemically-reactive group being protected. For example, if the chemically-reactive group is an amine or a hydrazide, the protecting group can be selected from the group of tert-butyloxycarbonyl (t-Boc) and 9-fluorenylmethoxycarbonyl (Fmoc). If the chemically-reactive group is a thiol, the protecting group can be orthopyridyldisulfide. If the chemically-reactive group is a carboxylic acid, such as butanoic or propionic acid, or a hydroxyl group, the protecting group can be benzyl or an alkyl group such as methyl or ethyl. Other protecting groups known in the art may also be used in the invention.

The terms "linking moiety", "linkage" or "linker" are used herein to refer to moieties or bonds that are formed as the result of a chemical reaction and typically are covalent linkages. Thus, the linkage represented by bond R*-B in the above formulae results from the reaction between an activated moiety, R, on the PGC with a biologically-active compound, i.e., B'. R* is the linking moiety formed from R upon reaction with B', and B is the biologically-active compound as conjugated to the PGC by reaction of a functional group on B' with R.

As used herein, the term "biologically-active compound" refers to those compounds that exhibit one or more biological responses or actions when administered to a subject and contain reactive groups that contain reactive moieties that are capable of reacting with and conjugating to at least one activated PGC of the invention. The term "biologically-active molecule", "biologically-active moiety" or "biologically-active agent" when used herein means any substance which can affect any physical or biochemical properties of any subject, including but not limited to viruses, bacteria, fungi, plants, animals, and humans. In particular, as used herein, biologically-active molecules include any substance intended for diagnosis, cure, mitigation, treatment, or prevention of disease in humans or other animals, or to otherwise enhance physical or mental well-being of humans or animals.

Examples of biologically-active molecules include, but are not limited to, peptides, peptide analogs, proteins, enzymes, small molecules, dyes, lipids, nucleosides, oligonucleotides, analogs of oligonucleotides, sugars, oligosaccharides, cells, viruses, liposomes, microparticles, surfaces and micelles.

Classes of biologically-active agents that are suitable for use with the invention include, but are not limited to, chemokines, lymphokines, antibodies, soluble receptors, anti-tumor agents, anti-anxiety agents, hormones, growth factors, antibiotics, fungicides, fungistatic agents, anti-viral agents, steroidal agents, antimicrobial agents, germicidal agents, antipyretic agents, antidiabetic agents, bronchodilators, antidiarrheal agents, coronary dilation agents, glycosides, spasmolytics, antihypertensive agents, antidepressants, antianxiety agents, other psychotherapeutic agents, corticosteroids, analgesics, contraceptives, nonsteroidal anti-inflammatory drugs, blood glucose lowering agents, cholesterol lowering agents, anticonvulsant agents, other antiepileptic agents, immunomodulators, anticholinergics, sympatholytics, sympathomimetics, vasodilatory agents, anticoagulants, antiarrhythmics, prostaglandins having various pharmacologic activities, diuretics, sleep aids, antihistaminic agents, antineoplastic agents, oncolytic agents, antiandrogens, antimalarial agents, antileprosy agents, and various other types of drugs. See Goodman and Gilman's The Basis of Therapeutics (Ninth Edition, Pergamon Press, Inc., USA, 1996) and The Merck Index (Thirteenth Edition, Merck & Co., Inc., USA, 2001), each of which is incorporated herein by reference.

Biologically-active compounds include any compound that exhibits a biological response in its present form, or any compound that exhibits a biological response as a result of a chemical conversion of its structure from its present form. For example, biologically-active compounds will include any compound that contains a protective group that, when cleaved, results in a compound that exhibits a biological response. Such cleavage can be the result, for example, of an in vivo reaction of the compound with endogenous enzymes or a pre-administration reaction of the compound, including its reaction with the activated PGCs of this invention. As a further example, biologically-active compounds will also include any compound which undergoes a stereotransformation, in vivo or ex vivo, to form a compound that exhibits a biological response or action.

Biologically-active compounds typically contain several reactive sites at which covalent attachment of the activated PGC is feasible. For example, amine groups can undergo acylations, sulfhydryl groups can undergo addition reactions and alkylations, carbonyl and carboxyl groups can undergo acylations, and aldehyde and hydroxyl groups can undergo amination and reductive amination. One or more of these reactions can be used in the preparation of the polyalkylene glycol-modified biologically-active compounds of the invention. In addition, biologically-active compounds can be modified to form reactive moieties on the compound that facilitate such reactions and the resultant conjugation to the activated PGC.

Those of ordinary skill will recognize numerous reaction mechanisms available to facilitate conjugation of the activated PGC to a biologically-active compound. For example, when the activating moiety, R, is a hydrazide group, it can be covalently coupled to sulfhydryl, sugar, and carbonyl moieties on the biologically-active compounds (after these moieties undergo oxidation to produce aldehydes). The reaction of hydrazide activating moieties (R) with aldehydes on biologically-active compounds (B') creates a hydrazone linkage (R*-B). When R is a maleimide group, it can be reacted with a sulfhydryl group to form a stable thioether linkage. If sulfhydryls are not present on the biologically-active compound, they may be created through disulfide reduction or through thiolation with 2-iminothiolane or SATA. When R is an imidoester it will react with primary amines on B' to form an imidoamide linkage. Imidoester conjugation is usually performed between pH 8.5-9.0. When connecting the activated PGCs to biologically-active proteins, imidoesters provide an advantage over other R groups since they do not affect the overall charge of the protein. They carry a positive charge at physiological pH, as do the primary amines they replace. Imidoester reactions are carried out between 0° C. and room temperature (e.g., at 4° C.), or at elevated temperatures under anhydrous conditions. When R is an NHS-ester, its principal target is primary amines. Accessible α-amine groups, for example those present on the N-termini of peptides and proteins, react with NHS-esters to form a covalent amide bond.

In some embodiments, R*-B is a hydrolytically-stable linkage. A hydrolytically stable linkage means that the linkage is substantially stable in water and does not react with water at useful pHs, e.g., the linkage is stable under physiological conditions for an extended period of time, perhaps even indefinitely. In other embodiments, R*-B is a hydrolytically-unstable or degradable linkage. A hydrolytically-unstable linkage means that the linkage is degradable in water or in aqueous solutions, including for example, blood. Enzymatically-unstable or degradable linkages also means that the linkage can be degraded by one or more enzymes.

As understood in the art, polyalkylene and related polymers may include degradable linkages in the polymer backbone or in the linker group between the polymer backbone and one or more of the terminal functional groups of the PGC molecule. For example, ester linkages formed by the reaction of, e.g., PGC carboxylic acids or activated PGC carboxylic acids with alcohol groups on a biologically-active compound generally hydrolyze under physiological conditions to release the agent. Other hydrolytically-degradable linkages include carbonate linkages; imine linkages resulted from reaction of an amine and an aldehyde (See, e.g., Ouchi et al., *Polymer Preprints*, 38(1):582-3 (1997)); phosphate ester linkages formed by reacting an alcohol with a phosphate group; acetal linkages that are the reaction product of an aldehyde and an alcohol; orthoester linkages that are the reaction product of a formate and an alcohol; peptide linkages formed by an amine group, e.g., at an end of a the PGC, and a carboxyl group of a peptide; and oligonucleotide linkages formed by a phosphoramidite group, e.g., at the end of a polymer, and a 5' hydroxyl group of an oligonucleotide.

The polyalkylene glycol, P, can be polyethylene glycol, having the structure of Formula II:

$$E\text{-}(O\text{---}CH_2CH_2)_a\text{---},\quad\quad\text{Formula II}$$

wherein a is an integer from 4 to 10,000 and E is hydrogen or a straight- or branched-chain $C_1$ to $C_{20}$ alkyl group, a detectable label, or a moiety suitable for forming a bond between the compound of Formula I and a biologically-active compound or precursor thereof.

Thus, when E is a moiety suitable for forming a bond between the compound of Formula I and a biologically-active compound or precursor thereof, E can be a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal. It is to be understood that E should be compatible with R so that reaction between E and R does not occur.

By "detectable label" is meant any label capable of detection. Non-limiting examples include radioactive isotopes, fluorescent moieties, phosphorescent moieties, chemiluminescent moieties, and quantum dots. Other detectable labels include biotin, cysteine, histidine, haemagglutinin, myc or flag tags.

In some embodiments, E has the structure according to Formula III or Formula IV:

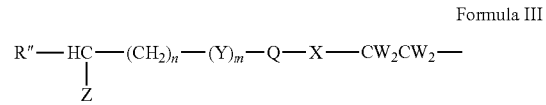

$$R''\text{---}HC\text{---}(CH_2)_n\text{---}(Y)_m\text{---}Q\text{---}X\text{---}CW_2CW_2\text{---}\quad\quad\text{Formula III}$$
$$|$$
$$Z$$

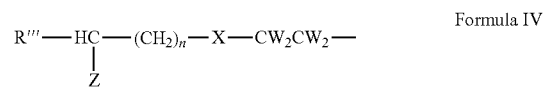

$$R'''\text{---}HC\text{---}(CH_2)_n\text{---}X\text{---}CW_2CW_2\text{---}\quad\quad\text{Formula IV}$$
$$|$$
$$Z$$

Each Q, X, Y, Z, m, and n are as defined above, and each W is, independently, hydrogen or a $C_1$ to $C_7$ alkyl.

In this class of compounds, R" is a moiety suitable for forming a bond between the compound of Formula III and a biologically-active compound or precursor thereof; and R''' is a moiety suitable for forming a bond between the compound of Formula IV and a biologically-active compound or precursor thereof.

R'' and R''' can be of carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal. It is to be understood that R'' and R''' should be compatible with R so that reaction with R does not occur.

As used herein, R'' and R''' upon conjugation to a biologically-active compound or precursor thereof, form linking moieties as defined above. Thus, R** is a linking moiety formed by the reaction of the R'' or R''' group on the activated PGC with a reactive functional group on the biologically-active compound, such that a covalent attachment results between the PGC and the biologically-active compound. R and R'' or R''' can be the same moiety or different moieties, and the biologically-active compound bound to each can be the same or different.

As used herein, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6, or 7 carbons in the ring structure.

Moreover, the term "alkyl" (or "lower alkyl") is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl, and sulfonate), and silyl groups, as well as ethers, alkylthios, carbonyls (including ketones, aldehydes, carboxylates, and esters), —$CF_3$, —CN and the like. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group). Exemplary aralkyl groups include, but are not limited to, benzyl and more generally $(CH_2)_n$Ph, where Ph is phenyl or substituted phenyl, and n is 1, 2, or 3.

The terms "alkenyl" and "alkynyl" refer to unsaturated aliphatic groups analogous in length and possible substitution to the alkyls described above, but that contain at least one double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls, and/or heterocyclyls.

The terms ortho, meta and para apply to 1,2-, 1,3-, and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine; naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with substituents as described above, such as, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

Heterocycles and carbocycles include fused bicyclic and bridged bicyclic ring structures.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

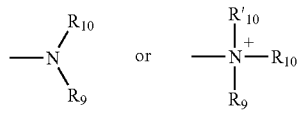

wherein R$_9$, R$_{10}$ and R'$_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8.

The term "alkylamine" as used herein means an amine group, as defined above, having a substituted or unsubstituted alkyl attached thereto, i.e., at least one of R$_9$ and R$_{10}$ is an alkyl group.

The term "acylamino" is art-recognized and refers to a moiety that can be represented by the general formula:

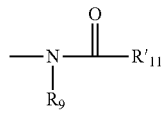

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art-recognized as an amino-substituted carbonyl and includes a moiety that can be represented by the general formula:

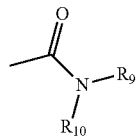

wherein R$_9$, R$_{10}$ are as defined above. Preferred embodiments of the amide will not include imides which may be unstable.

The term "amidine" is art-recognized as a group that can be represented by the general formula:

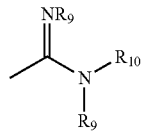

wherein R$_9$, R$_{10}$ are as defined above.

The term "guanidine" is art-recognized as a group that can be represented by the general formula:

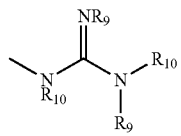

wherein R$_9$, R$_{10}$ are as defined above.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethylthio, and the like.

The term "carbonyl" is art-recognized and includes moieties that can be represented by the general formula:

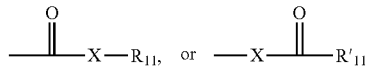

wherein X is a bond or represents an oxygen or a sulfur, and R$_{11}$ represents a hydrogen, an alkyl, an alkenyl, —(CH$_2$)$_m$—R$_8$ or a pharmaceutically-acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thioester." Where X is a sulfur and R$_{11}$ is hydrogen, the formula represents a "thiocarboxylic acid." Where X is a sulfur and R'$_{11}$ is hydrogen, the formula represents a "thioformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O-(CH$_2$)$_m$—R$_8$, where m and R$_8$ are described above.

The term "sulfonate" is art-recognized and includes a moiety that can be represented by the general formula:

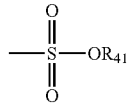

in which R$_{41}$ is an electron pair, hydrogen, alkyl, cycloalkyl, or aryl.

The term "sulfate" is art recognized and includes a moiety that can be represented by the general formula:

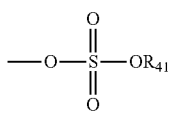

in which $R_{41}$ is as defined above.

The term "sulfonamido" is art recognized and includes a moiety that can be represented by the general formula:

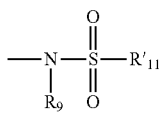

in which $R_9$ and $R'_{11}$ are as defined above.

The term "sulfamoyl" is art-recognized and includes a moiety that can be represented by the general formula:

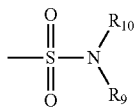

in which $R_9$ and $R_{10}$ are as defined above.

The term "sulfonyl", as used herein, refers to a moiety that can be represented by the general formula:

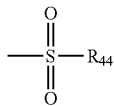

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

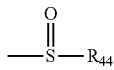

in which $R_{44}$ is selected from the group consisting of hydrogen, alkyl, alkenyl, alkynyl, cycloalkyl, heterocyclyl, aralkyl, or aryl.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

A comprehensive list of the abbreviations utilized by organic chemists of ordinary skill in the art appears in the first issue of each volume of the *Journal of Organic Chemistry*, this list is typically presented in a table entitled *Standard List of Abbreviations*. The abbreviations contained in said list, and all abbreviations utilized by organic chemists of ordinary skill in the art are hereby incorporated by reference.

In some embodiments, the compounds of the invention have the structure according to Formula V:

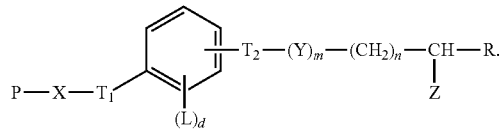

Formula V

X, Y, m, n, Z, and R' are as defined above, and R is an activating moiety as defined above, suitable for forming a bond between the compound of Formula V and a biologically-active compound or precursor. In particular embodiments, R is an aldehyde hydrate.

P is as defined above, and can be represented by Formula II $$E\text{-}(O\text{---}CH_2CH_2)_a\text{---},\quad\text{Formula II}$$

where E is as described above, and in some embodiments, can be represented by Formula III or IV.

$T_1$ and $T_2$ are, independently, absent, or a straight- or branched-chain, saturated or unsaturated $C_1$ to $C_{20}$ alkyl or heteroalkyl group, a $C_3$ to $C_8$ saturated or unsaturated cyclic alkyl or cyclic heteroalkyl, a substituted or unsubstituted aryl or heteroaryl group, or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

When d is zero, there are no additional substituents (L) on the aromatic ring. When d is an integer from 1 to 4, the substituents (L) can be a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

When R is an aldehyde, the compounds fall within those represented by Formula VI:

Formula VI $$P—X—T_1 \underset{(L)_d}{\overset{}{\text{—Ar—}}} T_2—(Y)_m—(CH_2)_n—\underset{Z}{\overset{}{CH}}—\overset{O}{\underset{}{C}}—H$$

where all other variables are as defined above.

For example, when X and Y are oxygen and R is an aldehyde, the compounds of the invention are represented by compound J.

Compound J $$P—O—T_1 \underset{(L)_d}{\overset{}{\text{—Ar—}}} T_2—O—(CH_2)_n—\underset{Z}{\overset{}{CH}}—\overset{O}{\underset{}{C}}—H,$$

where the $T_1$ and $T_2$ substituents can be in the ortho, meta, or para arrangement.

Where the $T_1$ and $T_2$ substituents are straight-chain alkyl groups, and d is zero, the compounds are represented by Formula IX:

Formula IX $$P—O—(CH_2)_u\text{—Ar—}(CH_2)_u—O—(CH_2)_n—\underset{Z}{\overset{}{CH}}—\overset{O}{\underset{}{C}}—H,$$

where each u is independently zero or an integer from one to five and all other variables are as defined above. In particular embodiments, Z is hydrogen or methyl.

Particular classes of compounds falling within Formula IX can be represented by Formulae VII and VIII:

Formula VII $$P—O\text{—Ar—}(CH_2)_n—\underset{Z}{\overset{}{CH}}—\overset{O}{\underset{}{C}}—H,$$

Formula VIII $$P—O\text{—Ar—}(CH_2)_n—\overset{O}{\underset{}{C}}—H,$$

Some representative activated polyalkylene glycol compounds include the following, where the polyalkylene glycol polymer is PEG or mPEG:

8

PEG—O—CH₂—(p-C₆H₄)—O—CH₂—CH(CH₃)—CHO

9

PEG—O—CH₂—(m-C₆H₄)—O—CH₂—CH(CH₃)—CHO

16

PEG—O—(p-C₆H₄)—CH₂—CHO

17

PEG—O—(p-C₆H₄)—CH₂—CH₂—CHO

18

PEG—O—(m-C₆H₄)—CH₂—CHO

In some embodiments, the compounds of the invention are represented by Formula X:

Formula X $$P—X—(CH_2)_n—\underset{Z}{\overset{}{CH}}—R,$$

where, as above, n is zero or an integer from one to five, and X is O, S, CO, CO₂, COS, SO, SO₂, CONR', SO₂NR', or NR'.

When X is NR', R' can be hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio. Z can be a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. When present, the substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

As defined above, R is an activating moiety suitable for forming a bond between the compound of Formula X and a biologically-active compound or precursor thereof. In some embodiments, R is an aldehyde hydrate.

P is a polyalkylene glycol polymer as defined above, and can be represented by Formula II:

  Formula II where E and a are as described above, and in some embodiments, can be represented by Formula III or IV. In some embodiments, E is methyl, and, therefore, P is mPEG.

When R is an aldehyde and X is oxygen, the compounds fall within the structure according to Formula XI:

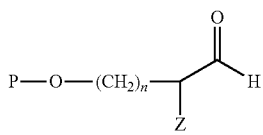  Formula XI where P, Z and n are as defined for Formula X.

When P is mPEG, the compounds are described by Formula XII:

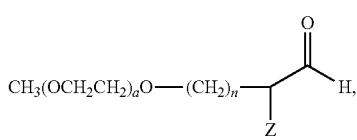  Formula XII and when n is one and Z is methyl, the compound is represented by Formula XIII:

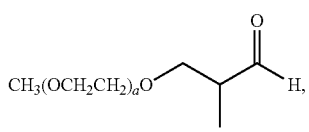  Formula XIII wherein a is an integer from 4 to 10,000.

Examples of synthetic pathways for making compounds according to the invention are set forth in the Examples below.

The invention also includes compositions of the activated polyalkylene glycol compounds (PGCs) of the invention and one or more biologically-active compounds. As described above, biologically-active compounds are those compounds that exhibit a biological response or action when administered to a subject. Unconjugated biologically-active compounds may be administered to a subject in addition to the compounds of the invention. Additionally, biologically-active compounds may contain reactive groups that are capable of reacting with and conjugating to at least one activated PGC of the invention.

The invention also includes conjugates of the novel PGCs with biologically-active compounds. In one embodiment, the conjugates are formed from a compound of Formula I and a biologically-active compound (B) and are described according to Formula XIV:

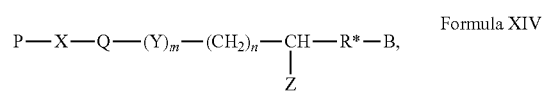  Formula XIV

As above, m is zero or one so that Y is present or absent, n is zero or an integer from one to five, and X and Y are independently O, S, CO, $CO_2$, COS, SO, $SO_2$, CONR', $SO_2$NR', or NR'.

Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl or heteroalkaryl group. When present, the substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

Each R' and Z is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein the substituents are selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, and alkylthio;

R* is a linking moiety formed from the reaction of R with a corresponding functional group on the biologically-active compound, B, as described above. For example, R* is formed from the reaction of a moiety such as a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal functionality with a biologically-active compound or precursor thereof.

P is a polyalkylene glycol polymer as defined above, and can be represented by Formula II:

  Formula II where E is hydrogen, a straight- or branched-chain $C_1$ to $C_{20}$ alkyl group (e.g., methyl), a detectable label, or a moiety suitable for forming a bond between the compound of Formula XIV and a biologically-active compound or precursor thereof. As above, a is an integer from 4 to 10,000.

Where E is a detectable label, the label can be, for example, a radioactive isotope, a fluorescent moiety, a phosphorescent moiety, a chemiluminescent moiety, or a quantum dot.

When E is a moiety suitable for forming a bond between the compound of Formula XIV and a biologically-active compound or precursor thereof, E can form a bond to another molecule of the biologically-active compound (B) so that the activated polyalkylene glycol compound is bound at either terminus to a molecule of the same type of biologically-active compound, to produce a dimer of the molecule.

In some embodiments, E forms a bond to a biologically-active compound other than B, creating a heterodimer of biologically-active compounds or precursors thereof.

In other embodiments, E forms an additional bond to the biologically-active compound, B, such that both E and R are bound through different functional groups of the same molecule of the biologically-active compound or precursor thereof.

When E is capable of forming a bond to a biologically-active molecule or precursor thereof, E can be the same as or different from R and is chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

When E is capable of forming a bond to a biologically-active molecule or precursor thereof, E can have the structure according to Formula III or Formula IV:

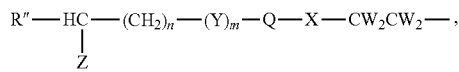
Formula III

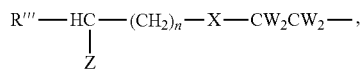
Formula IV where each Q, X, Y, Z, m, and n are, independently, as defined above, each W is, independently, hydrogen or a $C_1$ to $C_7$ alkyl, R" is a moiety suitable for forming a bond between the compound of Formula III and a biologically-active compound or precursor thereof, and R'" is a moiety suitable for forming a bond between the compound of Formula IV and a biologically-active compound or precursor thereof.

R" and R'" are, independently chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

When Q in Formula XIV is a substituted or unsubstituted alkaryl, the conjugate is formed from an activated polyalkylene glycol of Formula V and a biologically-active molecule (B), and is described according to Formula XV:

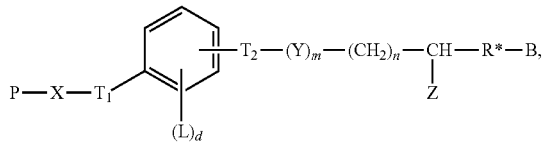
Formula XV where $T_1$ and $T_2$ are, independently, absent, or a straight- or branched-chain, saturated or unsaturated $C_1$ to $C_{20}$ alkyl or heteroalkyl group, a $C_3$ to $C_8$ saturated or unsaturated cyclic alkyl or cyclic heteroalkyl, a substituted or unsubstituted aryl or heteroaryl group, or a substituted or unsubstituted alkaryl wherein the alkyl is a $C_1$ to $C_{20}$ saturated or unsaturated alkyl or heteroalkaryl group. When present, the substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio. In some embodiments, $T_1$ and $T_2$, if present, are straight- or branched-chain saturated or unsaturated or $C_1$ to $C_{20}$ alkyl or heteroalkyl group.

d is zero (e.g., there are no L substituents on the aromatic ring) or an integer from 1 to 4. Each L is, when present, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

All other variables are as described above, including P, which is a polyalkylene glycol polymer, and can be represented by Formula II:

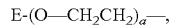 Formula II where E is hydrogen, a straight- or branched-chain $C_1$ to $C_{20}$ alkyl group (e.g., methyl), a detectable label, or a moiety suitable for forming a bond between the compound of Formula XV and a biologically-active compound or precursor thereof. As above, a is an integer from 4 to 10,000.

Where E is a detectable label, the label can be, for example, a radioactive isotope, a fluorescent moiety, a phosphorescent moiety, a chemiluminescent moiety, or a quantum dot.

When E is a moiety suitable for forming a bond between the compound of Formula XV, and a biologically-active compound, B, E can form a bond to another molecule of the biologically-active compound (B) so that the activated polyalkylene glycol compound is bound at either terminus to a molecule of the same type of biologically-active compound, to produce a dimer of the molecule.

In some embodiments, E forms a bond to a biologically-active compound other than B, creating a heterodimer of biologically-active compounds or precursors thereof.

In other embodiments, E forms an additional bond to the biologically-active compound, B, such that both E and R are bound through different functional groups of the same molecule of the biologically-active compound or precursor thereof.

When E is capable of forming a bond to a biologically-active molecule or precursor thereof, E can be the same as or different from R and is chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

When E can form a bond with a biologically-active compound or precursor thereof, in some embodiments, E can be Formula III or Formula IV:

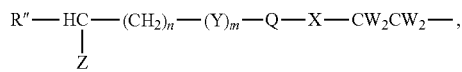

Formula III

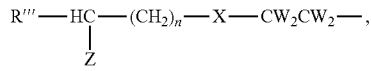

Formula IV where each Q, X, Y, Z, m, and n are, independently, as defined above, each W is, independently, hydrogen or a $C_1$ to $C_7$ alkyl, R'' is a moiety suitable for forming a bond between the compound of Formula III and a biologically-active compound or precursor thereof, and R''' is a moiety suitable for forming a bond between the compound of Formula IV and a biologically-active compound or precursor thereof.

R'' and R''' are, independently chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

When bound at both ends to a biologically-active compound or precursor thereof, these bifunctional molecules can be represented according to Formula XX or Formula XXI:

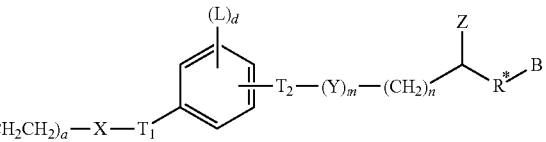

Formula XX

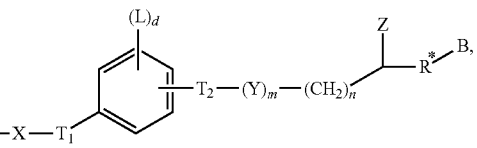

Formula XXI where each X and Y, $T_1$ and $T_2$, R' and Z, L, Q, m, n, a, and n are as described above, and each W is, independently, hydrogen or a $C_1$ to $C_7$ alkyl. R* and R** are, independently, linking moieties formed from the reaction of R and R'' with a biologically-active compound or precursor thereof, and B and B' are each a biologically-active compound, or precursor thereof, after conjugation with R and R'', respectively.

In some embodiments, B and B' are the same type of biologically-active compound. In other embodiments, B and B' are different biologically-active compounds. In still other embodiments, B. and B' are the same biologically active molecule. In additional embodiments, R* and R** are the same. In other embodiments, R* and R** are different. For example, in some embodiments, E can form a bond to another molecule of the biologically-active compound (B=B') so that the activated PGC is bound at either terminus to a molecule of the same type of biologically-active compound, to produce a dimer of the molecule. In some embodiments, E forms a bond to a biologically-active compound other than B (B is not B'), creating a heterodimer of biologically-active compounds or precursors thereof. In other embodiments, E forms an additional bond to the biologically-active compound, B, such that both E (through R'' or R''') and R are bound through different functional groups of the same molecule of the biologically-active compound or precursor thereof.

In some embodiments, R* or R** is methylene group and B or B' is a biologically-active molecule containing an amino group, where the methylene group forms a bond with the amino group on B. For example, the amine can be the amino terminus of a peptide, an amine of an amino acid side chain of a peptide, or an amine of a glycosylation substituent of a glycosylated peptide. In some embodiments, the peptide is an interferon, such as interferon-beta, e.g., interferon-beta-1a. In some embodiments, this type of bond is formed by a reductive alkylation reaction.

Where the $T_1$ and $T_2$ substituents of Formula XV are straight-chain alkyl groups, X and Y are oxygen, and d is zero, the conjugates are represented by Formula XIX:

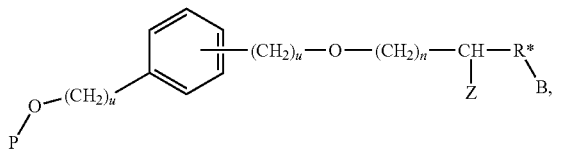

Formula XIX where each u is independently zero or an integer from one to five and all other variables are as defined above. In particular embodiments, Z is hydrogen or methyl.

Particular classes of compounds falling within Formula XV can be represented by Formulae XVII and XVIII formed from the reaction of Formulae VII and VIII, respectively, with a biologically-active compound, or precursor thereof:

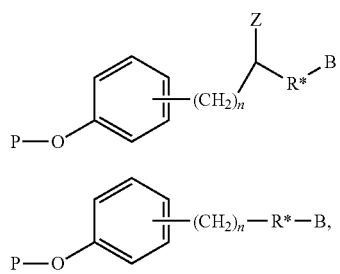

Formula XVII

Formula XVIII where n is zero or an integer from one to five, P is a polyalkylene glycol polymer, as described above, Z is hydrogen, a straight- or branched-chain, saturated or unsaturated $C_1$ to $C_{20}$ alkyl or heteroalkyl group, R* is a linking moiety as described above, B is a biologically-active molecule. These compounds can be bifunctional or monofunctional, depending on the identity of E, as described above.

In some embodiments, R* is a methylene group and B is a biologically-active molecule containing an amino group, where the methylene group forms a bond with the amino group on B. For example, the amine scan be the amino terminus of a peptide, an amine of an amino acid side chain of a peptide, or an amine of a glycosylation substituent of a glycosylated peptide. In some embodiments, the peptide is an interferon, such as interferon-beta, e.g., interferon-beta-1a. In some embodiments, this type of bond is formed by a reductive alkylation reaction.

The conjugates of the invention can also be formed from reaction of compounds according to Formula X with a biologically-active compound or precursor thereof, to form conjugates according to Formula XXII:

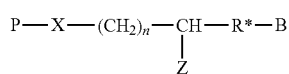

Formula XXII where B is a biologically-active molecule, as described above and n is zero or an integer from one to five.

X is O, S, CO, $CO_2$, COS, SO, $SO_2$, CONR', $SO_2NR'$, or NR', when X is NR', R' is hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. If present, the substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

Z is a straight- or branched-chain, saturated or unsaturated $C_1$ to $C_{20}$ alkyl or heteroalkyl group, $C_3$ to $C_9$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

R* is a linking moiety formed from the reaction of R with a corresponding functional group on the biologically-active compound, B, as described above. For example, R* is formed from the reaction of a moiety such as a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal functionality with a biologically-active compound or precursor thereof.

In some embodiments, Z is methyl and n is one.

P is a polyalkylene glycol polymer as defined above, and can be represented by Formula II:

$$E\text{-}(O\text{---}CH_2CH_2)_a\text{---},$$ Formula II where E is hydrogen, a straight- or branched-chain $C_1$ to $C_{20}$ alkyl group (e.g., methyl), a detectable label, or a moiety suitable for forming a bond between the compound of Formula XXII and a biologically-active compound or precursor thereof. As above, a is an integer from 4 to 10,000.

Where E is a detectable label, the label can be, for example, a radioactive isotope, a fluorescent moiety, a phosphorescent moiety, a chemiluminescent moiety, or a quantum dot.

When E is capable of forming a bond to a biologically-active molecule or precursor thereof, a bifunctional molecule results. E can form a bond to another molecule of the biologically-active compound (B) so that the activated polyalkylene glycol compound is bound at either terminus to a molecule of the same type of biologically-active compound, to produce a dimer of the molecule.

In some embodiments, E forms a bond to a biologically-active compound other than B, creating a heterodimer of biologically-active compounds or precursors thereof.

In other embodiments, E forms an additional bond to the biologically-active compound, B, such that both E and R are bound through different functional groups of the same molecule of the biologically-active compound or precursor thereof.

When E is capable of forming a bond to a biologically-active molecule or precursor thereof, E can be the same as or different from R and is chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

In some embodiments, E can have the structure according to Formula III or Formula IV:

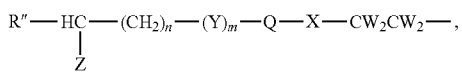

Formula III

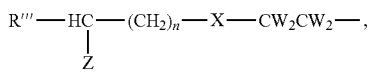

Formula IV where each Q, X, Y, Z, m, and n are, independently, as defined above, each W is, independently, hydrogen or a $C_1$ to $C_7$ alkyl, R" is a moiety suitable for forming a bond between the compound of Formula III and a biologically-active compound or precursor thereof, and R'" is a moiety suitable for forming a bond between the compound of Formula IV and a biologically-active compound or precursor thereof.

R" and R'" are, independently chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties, and can be the same or different from R.

When bound at both ends to a biologically-active compound or precursor thereof, these bifunctional molecules can be represented according to Formula XXIV or Formula XXV:

or heteroalkaryl group. If present, the substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

Each W is, independently, hydrogen or a $C_1$ to $C_7$ alkyl, in is zero or one, a is an integer from 4 to 10,000, and each n is independently 0 or an integer from 1 to 5.

R* and R** are independently linking moieties as described above, B and B' are independently biologically-active molecules and can be the same or different.

E (through R" or R'") can form a bond to another molecule of the biologically-active compound (B) so that the activated polyalkylene glycol compound is bound at either terminus to a molecule of the same type of biologically-active compound, to produce a dimer of the molecule.

In some embodiments, E (through R" or R'") forms a bond to a biologically-active compound other than B, creating a heterodimer of biologically-active compounds or precursors thereof.

In other embodiments, E (through R" or R'") forms an additional bond to the biologically-active compound, B, such that both E and R are bound through different functional groups of the same molecule of the biologically-active compound or precursor thereof.

R" and R'" can be the same as or different from R, and are chosen from carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, and glyoxal moieties.

In some embodiments, R* or R** is a methylene group and B or B' is a biologically-active molecule containing an amino Formula XXIV

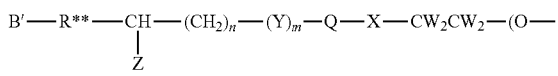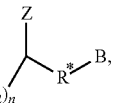

Formula XXV

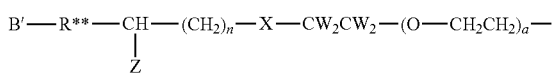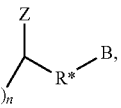

where each X and Y is independently O, S, CO, $CO_2$, COS, SO, $SO_2$, CONR', $SO_2NR'$, or NR', and each R' and Z is, independently, hydrogen, a straight- or branched-chain, saturated or unsaturated $C_1$ to $C_{20}$ alkyl or heteroalkyl group.

Q is a $C_3$ to $C_8$ saturated or unsaturated cyclic alkyl or cyclic heteroalkyl (including fused bicyclic and bridged bicyclic ring structures), a substituted or unsubstituted aryl or heteroaryl group, or a substituted or unsubstituted alkaryl wherein the alkyl is a $C_1$ to $C_{20}$ saturated or unsaturated alkyl group, where the methylene group forms a bond with the amino group on B. For example, the amine can be the amino terminus of a peptide, an amine of an amino acid side chain of a peptide, or an amine of a glycosylation substituent of a glycosylated peptide. In some embodiments, the peptide is an interferon, such as interferon-beta, e.g., interferon-beta-1a. In some embodiments, this type of bond is formed by a reductive alkylation reaction.

The conjugates of the invention can be prepared by coupling a biologically-active compound to a polyalkylene glycol compound as described in the Examples. In some embodiments, the coupling is achieved via a reductive alkylation reaction.

Biologically-active compounds of interest include any substance intended for diagnosis, cure mitigation, treatment, or prevention of disease in humans or other animals, or to otherwise enhance physical or mental well-being of humans or animals. Examples of biologically-active molecules include, but are not limited to, peptides, peptide analogs, proteins, enzymes, small molecules, dyes, lipids, nucleosides, oligonucleotides, analogs of oligonucleotides, sugars, oligosaccharides, cells, viruses, liposomes, microparticles, surfaces and micelles. This class of compounds also include precursors of these types of molecules. Classes of biologically-active agents that are suitable for use with the invention include, but are not limited to, cytokines, chemokines, lymphokines, soluble receptors, antibodies, antibiotics, fungicides, anti-viral agents, anti-inflammatory agents, anti-tumor agents, cardiovascular agents, anti-anxiety agents, hormones, growth factors, steroidal agents, and the like.

The biologically-active compound can be a peptide, such as an interferon, including interferon-beta (e.g., interferon-beta-1a) or interferon-alpha.

Because the polymeric modification with a PGC of the invention reduces antigenic responses, a foreign peptide need not be completely autologous in order to be used as a therapeutic. For example, a peptide, such as interferon, used to prepare polymer conjugates may be prepared from a mammalian extract, such as human, ruminant, or bovine interferon, or can be synthetically or recombinantly produced.

For example, in one aspect, the invention is directed to compounds and methods for treating conditions that are susceptible of treatment with interferon alpha or beta. Administration of a polyalkylene glycol conjugated interferon beta (hereinafter "PGC IFN-beta", "PGC IFN-β", e.g., PEG IFN-beta", "PEG IFN-β" "PEGylated IFN-beta", or "PEGylated IFN-β") provides improved therapeutic benefits, while substantially reducing or eliminating entirely the undesirable side effects normally associated with conventionally practiced interferon alpha or beta treatment regimes.

The PGC IFN-beta can be prepared by attaching a polyalkylene polymer to the terminal amino group of the IFN beta molecule. A single activated polyalkylene glycol molecule can be conjugated to the N-terminus of IFN beta via a reductive alkylation reaction.

The PGC IFN-beta conjugate can be formulated, for example, as a liquid or a lyophilized powder for injection. The objective of conjugation of IFN beta with a PGC is to improve the delivery of the protein by significantly prolonging its plasma half-life, and thereby provide protracted activity of IFN beta.

The term "interferon" or "IFN" as used herein means the family of highly homologous species-specific proteins that inhibit viral replication and cellular proliferation and modulate immune response. Human interferons are grouped into two classes; Type 1, including α- and β-interferon, and Type II, which is represented by γ-interferon only. Recombinant forms of each group have been developed and are commercially available. Subtypes in each group are based on antigenic/structural characteristics.

The terms "beta interferon", "beta-interferon", "beta IFN", "beta-IFN", "13 interferon", "β-interferon", "(β IFN", "β-IFN", "interferon beta", "interferon-beta", "interferon β", "interferon-β", "IFN beta", "IFN-beta", "IFN β", "IFN-β", and "human fibroblast interferon" are used interchangeably herein to describe members of the group of interferon beta's which have distinct amino acid sequences as have been identified by isolating and sequencing DNA encoding the peptides.

Additionally, the terms "beta interferon 1a", "beta interferon-1a" "beta-interferon 1a", "beta-interferon-1a", "beta IFN 1a", "beta IFN-1a", "beta-IFN 1a", "beta-IFN-1a", "13 interferon 1a", "β interferon-1a", "β-interferon 1a", "β-interferon-1a", "β IFN 1a", "β IFN-1a", "β-IFN 1a", "β-IFN-1a", "interferon beta 1a", "interferon beta-1a", "interferon-beta 1a", "interferon-beta-1a", "interferon β1a", "interferon β-1a", "interferon-β1a", "interferon-β-1a", "IFN beta 1a", "IFN beta-1a", "IFN-beta 1a", "IFN-beta-1a", "IFN β 1a", "IFN β-1a", "IFN-β 1a", "IFN-β-1a" are used interchangeably herein to describe recombinantly- or synthetically-produced interferon beta that has the naturally-occurring (wild type) amino acid sequences.

The advent of recombinant DNA technology applied to interferon production has permitted several human interferons to be successfully synthesized, thereby enabling the large-scale fermentation, production, isolation, and purification of various interferons to homogeneity. Recombinantly produced interferon retains some—or most of—its in vitro and in vivo antiviral and immunomodulatory activities. It is also understood that recombinant techniques could also include a glycosylation site for addition of a carbohydrate moiety on the recombinantly-derived polypeptide.

The construction of recombinant DNA plasmids containing sequences encoding at least part of human fibroblast interferon and the expression of a polypeptide having immunological or biological activity of human fibroblast interferon is also contemplated. The construction of hybrid beta-interferon genes containing combinations of different subtype sequences can be accomplished by techniques known to those of skill in the art.

Typical suitable recombinant beta-interferons which may be used in the practice of the invention include but are not limited to interferon beta-1a such as AVONEX® available from Biogen, Inc., Cambridge, Mass., and interferon-beta-1b such as BETASERON® available from Berlex, Richmond, Calif.

There are many mechanisms by which IFN-induced gene products provide protective effects against viral infection. Such inhibitory viral effects occur at different stages of the viral life cycle. See. U.S. Pat. No. 6,030,785. For example, IFN can inhibit uncoating of viral particles, penetration, and/or fusion caused by viruses.

Conditions that can be treated in accordance with the present invention are generally those that are susceptible to treatment with interferon. For example, susceptible conditions include those, which would respond positively or favorably (as these terms are known in the medical arts) to interferon beta-based therapy. For purposes of the invention, conditions that can be treated with interferon beta therapy described herein include those conditions in which treatment with an interferon beta shows some efficacy, but in which the negative side effects of IFN-β treatment outweigh the benefits. Treatment according to the methods of the invention results in substantially reduced or eliminated side effects as compared to conventional interferon beta treatment. In addition, conditions traditionally thought to be refractory to IFN-β treatment, or those for which it is impractical to treat with a manageable dosage of IFN-β, can be treated in accordance with the methods of the present invention.

The PGC IFN-β compounds of the invention can be used alone or in combination with one or more agents useful for treatment for a particular condition. At least one pilot study of recombinant interferon beta-1a for the treatment of chronic hepatitis C has been conducted. See generally Habersetzer et al., Liver 30:437-441 (2000), incorporated herein by reference. For example, the compounds can be administered in combination with known antiviral agents for treatment of a viral infection. See Kakumu et al., Gastroenterology 105: 507-12 (1993) and Pepinsky, et al., J. Pharmacology and Experimental Therapeutics, 297:1059-1066 (2001), incorporated herein by reference.

As used herein, the term "antivirals" may include, for example, small molecules, peptides, sugars, proteins, virus-derived molecules, protease inhibitors, nucleotide analogs and/or nucleoside analogs. A "small molecule" as the term is used herein refers to an organic molecule of less than about 2500 amu (atomic mass units), preferably less than about 1000 amu. Examples of suitable antiviral compounds include, but are not limited to, ribavirin, levovirin, MB6866, zidovudine 3TC, FTC, acyclovir, gancyclovir, viramide, VX-497, VX-950, and ISIS-14803.

Exemplary conditions which can be treated with interferon include, but are not limited to, cell proliferation disorders, in particular multiple sclerosis, cancer (e.g., hairy cell leukemia, Kaposi's sarcoma, chronic myelogenous leukemia, multiple myeloma, basal cell carcinoma and malignant melanoma, ovarian cancer, cutaneous T cell lymphoma), and viral infections. Without limitation, treatment with interferon may be used to treat conditions which would benefit from inhibiting the replication of interferon-sensitive viruses. For example, interferon can be used alone or in combination with AZT in the treatment of human immunodeficiency virus (HIV)/AIDS or in combination with ribavirin in the treatment of HCV. Viral infections which may be treated in accordance with the invention include, but are not limited to, hepatitis A, hepatitis B, hepatitis C, other non-Anon-B hepatitis, herpes virus, Epstein-Barr virus (EBV), cytomegalovirus (CMV), herpes simplex, human herpes virus type 6 (HHV-6), papilloma, poxvirus, picornavirus, adenovirus, rhinovirus, human T lymphotropic virus-type and 2 (HTLV-1/-2), human rotavirus, rabies, retroviruses including HIV, encephalitis, and respiratory viral infections. The methods of the invention can also be used to modify various immune responses.

A correlation between HCV genotype and response to interferon therapy has been observed. See U.S. Pat. No. 6,030,785; Enomoto et al., N. Engl. J. Med. 334:77-81 (1996); Enomoto et al., J. Clin. Invest. 96:224-30 (1995). The response rate in patients infected with HCV-1b is less than 40%. See U.S. Pat. No. 6,030,785. Similar low response rates have also been observed in patients infected with HCV-1a. See id.; Hoofnagel et al., Intervirology 37:87-100 (1994). However, the response rate in patients infected with HCV-2 is nearly 80%. See U.S. Pat. No. 6,030,785; Fried et al., Semin. Liver Dis. 15:82-91 (1995). In fact, an amino acid sequence of a discrete region of the NS5A protein of HCV genotype 1b was found to correlate with sensitivity to interferon. See U.S. Pat. No. 6,030,785, incorporated herein by reference. See also Enomoto et al. 1996; Enomoto et al. 1995. This region has been identified as the interferon sensitivity determining region (ISDR). See id.

The PGC IFN-beta conjugate is administered in a pharmacologically-effective amount to treat any of the conditions described above, and is based on the IFN beta activity of the polymeric conjugate. The term "pharmacologically-effective amount" means the amount of a drug or pharmaceutical agent that will elicit the biological or medical response of a tissue, system, animal or human that is being sought by a researcher or clinician. It is an amount that is sufficient to significantly affect a positive clinical response while maintaining diminished levels of side effects. The amount of PGC IFN-beta which may be administered to a subject in need thereof is in the range of 0.01-100 µg/kg, or more preferably 0.01-10 µg/kg, administered in single or divided doses.

Administration of the described dosages may be every other day, but preferably occurs once a week or once every other week. Doses are administered over at least a 24 week period by injection.

Administration of the dose can be oral, topical, intravenous, subcutaneous, intramuscular, or any other acceptable systemic method. Based on the judgment of the attending clinician, the amount of drug administered and the treatment regimen used will, of course, be dependent on the age, sex and medical history of the patient being treated, the neutrophil count (e.g., the severity of the neutropenia), the severity of the specific disease condition and the tolerance of the patient to the treatment as evidenced by local toxicity and by systemic side-effects.

In practice, the conjugates of the invention are administered in amounts which will be sufficient to inhibit or prevent undesired medical conditions or disease in a subject, such as a mammal, and are used in the form most suitable for such purposes. The compositions are preferably suitable for internal use and include an effective amount of a pharmacologically-active compound of the invention, alone or in combination with other active agents, with one or more pharmaceutically-acceptable carriers. The compounds are especially useful in that they have very low, if any, toxicity.

The conjugates herein described can form the active ingredient of a pharmaceutical composition, and are typically administered in a mixture with suitable pharmaceutical diluents, excipients or carriers (collectively referred to herein as "carrier" materials) suitably selected with respect to the intended form of administration, that is, oral tablets, capsules, elixirs, syrups and the like. The compositions typically will include an effective amount of active compound or the pharmaceutically-acceptable salt thereof, and in addition, and may also include any carrier materials as are customarily used in the pharmaceutical sciences. Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages.

Conventional pharmaceutical compositions comprising a pharmacologically-effective amount of a conjugate, e.g., PGC IFN-beta, together with pharmaceutically-acceptable carriers, adjuvants, diluents, preservatives and/or solubilizers may be used in the practice of the invention. Pharmaceutical compositions of interferon include diluents of various buffers (e.g., arginine, Tris-HCl, acetate, phosphate) having a range of pH and ionic strength, carriers (e.g., human serum albumin), solubilizers (e.g., tween, polysorbate), and preservatives (e.g., benzyl alcohol). See, for example, U.S. Pat. No. 4,496,537.

Administration of the active compounds described herein can be via any of the accepted modes of administration for therapeutic agents. These methods include systemic or local administration such as oral, nasal, parenteral, transdermal, subcutaneous, or topical administration modes.

For instance, for oral administration in the form of a tablet or capsule (e.g., a gelatin capsule), the active drug component can be combined with an oral, non-toxic pharmaceutically-acceptable inert carrier such as ethanol, glycerol, water, and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, sugars, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt, and/or polyethylene glycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The conjugates of the invention can also be administered in such oral dosage forms as timed-release and sustained-release tablets or capsules, pills, powders, granules, elixers, tinctures, suspensions, syrups, and emulsions.

Liquid, particularly injectable compositions can, for example, be prepared by dissolving, dispersing, etc. The active compound is dissolved in or mixed with a pharmaceutically-pure solvent such as, for example, water, saline, aqueous dextrose, glycerol, ethanol, and the like, to thereby form the injectable solution or suspension. Additionally, solid forms suitable for dissolving in liquid prior to injection can be formulated. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically-valuable substances.

The conjugates of the present invention can be administered in intravenous (e.g., bolus or infusion), intraperitoneal, subcutaneous or intramuscular form, all using forms well known to those of ordinary skill in the pharmaceutical arts. Injectables can be prepared in conventional forms, either as liquid solutions or suspensions.

Parental injectable administration is generally used for subcutaneous, intramuscular or intravenous injections and infusions. For example, when a subcutaneous injection is used to deliver 0.01-100 µg/kg, or more preferably 0.01-10 µg/kg of PEGylated IFN-beta over one week, two injections of 0.005-50 µg/kg, or more preferably 0.005-5 µg/kg, respectively, may be administered at 0 and 72 hours. Additionally, one approach for parenteral administration employs the implantation of a slow-release or sustained-released system, which assures that a constant level of dosage is maintained, according to U.S. Pat. No. 3,710,795, incorporated herein by reference.

Furthermore, preferred conjugates for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosols, sprays and gels, wherein the amount administered would be 10-100 times the dose typically given by parenteral administration.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The conjugates of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine, or phosphatidylcholines. In some embodiments, a film of lipid components is hydrated with an aqueous solution of drug to a form lipid layer encapsulating the drug, as described in U.S. Pat. No. 5,262,564.

Conjugates of the present invention may also be delivered by the use of immunoglobulin fusions as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. The conjugates can also be coupled to proteins, such as, for example, receptor proteins and albumin. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

The dosage regimen utilizing the conjugates is selected in accordance with a variety of factors including type, species, age, weight, sex and medical condition of the patient; the severity of the condition to be treated; the route of administration; the renal and hepatic function of the patient; and the particular compound or salt thereof employed. The activity of the compounds of the invention and sensitivity of the patient to side effects are also considered. An ordinarily skilled physician or veterinarian can readily determine and prescribe the effective amount of the drug required to prevent, counter or arrest the progress of the condition.

Oral dosages of the present invention, when used for the indicated effects, will range between about 0.01-100 µg/kg/day orally, or more preferably 0.01-10 µg/kg/day orally. The compositions are preferably provided in the form of scored tablets containing 0.5-5000 µg, or more preferably 0.5-500 µg of active ingredient.

For any route of administration, divided or single doses may be used. For example, compounds of the present invention may be administered daily or weekly, in a single dose, or the total dosage may be administered in divided doses of two, three or four.

Any of the above pharmaceutical compositions may contain 0.1-99%, 1-70%, or, preferably, 1-50% of the active compounds of the invention as active ingredients.

As described above, the course of the disease and its response to drug treatments may be followed by clinical examination and laboratory findings. The effectiveness of the therapy of the invention is determined by the extent to which the previously described signs and symptoms of a condition, e.g., chronic hepatitis, are alleviated and the extent to which the normal side effects of interferon (i.e., flu-like symptoms such as fever, headache, chills, myalgia, fatigue, etc. and central nervous system related symptoms such as depression, paresthesia, impaired concentration, etc.) are eliminated or substantially reduced.

In some embodiments, a polyalkylated compound of the invention (e.g., a PEGylated interferon) is administered in conjunction with one or more pharmaceutical agents useful for treatment for a particular condition. For example, a polyalkylated protein can be administered in combination with a known antiviral agent or agent for treatment of a viral infection. Such antiviral compounds include, for example, ribavirin, levovirin, MB6866, and zidovudine 3TC, FTC, acyclovir, gancyclovir, viramide, VX-497, VX-950, and ISIS-14803.

The conjugate and antiviral can be simultaneously administered (e.g., the agents are administered to a patient together); sequentially administered (e.g., the agents are administered to the patient one after the other); or alternatively administered (e.g., the agents are administered in a repeating series, such as agent A then agent B, then agent A, etc.).

In the practice of the invention, the preferred PGC IFN-beta (e.g., PEG IFN-beta) may be administered to patients infected with the hepatitis C virus. Use of PEG IFN-beta-1a is preferred.

Patients are selected for treatment from anti-HCV antibody-positive patients with biopsy-documented chronic active hepatitis.

In order to follow the course of HCV replication in subjects in response to drug treatment, HCV RNA may be measured in serum samples by, for example, a nested polymerase chain reaction assay that uses two sets of primers derived from the NS3 and NS4 non-structural gene regions of the HCV genome. See Farci et al., 1991, New Eng. J. Med. 325:98-104. Ulrich et al., 1990. J. Clin. Invest., 86:1609-1614.

Antiviral activity may be measured by changes in HCV-RNA titer. HCV RNA data may be analyzed by comparing titers at the end of treatment with a pre-treatment baseline measurement. Reduction in HCV RNA by week 4 provides evidence of antiviral activity of a compound. See Meter et al., 1993, Antimicrob. Agents Chemother. 37(3):595-97; Orito et al., 1995, J. Medical Virology, 46:109-115. Changes of at least two orders of magnitude (>2 log) is interpreted as evidence of antiviral activity.

A person suffering from chronic hepatitis C infection may exhibit one or more of the following signs or symptoms: (a) elevated serum alanine aminotransferase (ALT), (b) positive test for anti-HCV antibodies, (c) presence of HCV as demonstrated by a positive test for HCV-RNA, (d) clinical stigmata of chronic liver disease, (e) hepatocellular damage. Such criteria may not only be used to diagnose hepatitis C, but can be used to evaluate a patient's response to drug treatment.

Elevated alanine aminotransferase (ALT) and aspartate aminotransferase (AST) are known to occur in uncontrolled hepatitis C, and a complete response to treatment is generally defined as the normalization of these serum enzymes, particularly ALT. See Davis et al., 1989, New Eng. J. Med. 321:1501-1506. ALT is an enzyme released when liver cells are destroyed and is symptomatic of HCV infection. Interferon causes synthesis of the enzyme 2',5'-oligoadenylate synthetase (2'5'OAS), which in turn, results in the degradation of the viral mRNA. See Houglum, 1983, Clinical Pharmacology 2:20-28. Increases in serum levels of the 2'5'OAS coincide with decrease in ALT levels.

Histological examination of liver biopsy samples may be used as a second criteria for evaluation. See, e.g., Knodell et al., 1981, Hepatology 1:431-435, whose Histological Activity Index (portal inflammation, piecemeal or bridging necrosis, lobular injury, and fibrosis) provides a scoring method for disease activity.

Safety and tolerability or treatment may be determined by clinical evaluations and measure of white blood cell and neutrophil counts. This may be assessed through periodic monitoring of hematological parameters e.g., white blood cell, neutrophil, platelet, and red blood cell counts).

Various other extended- or sustained-release formulations can be prepared using conventional methods well known in the art.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. All patents and publications cited herein are incorporated by reference.

EXAMPLES

Example 1

Synthesis of Activated Polyalkylene Glycols

A) Alkylation of Alcohols

Activated polyalkylene glycols are synthesized by alkylating a polyalkylene glycol having a free terminal hydroxyl functionality. A generic reaction is outlined in Scheme I:

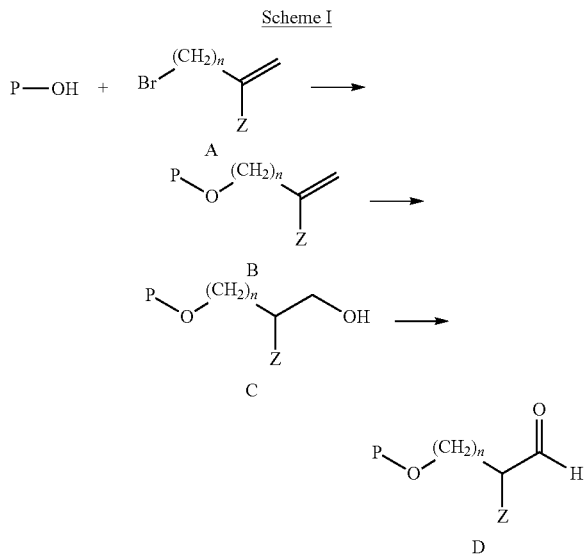

The polyalkylene glycol (P—OH) is reacted with the alkyl halide (A) to form the ether (B). Compound B is then hydroxylated to form the alcohol (C), which is oxidized to the aldehyde (D). In these compounds, n is an integer from zero to five and Z can be a straight- or branched-chain, saturated or unsaturated $C_1$ to $C_{20}$ alkyl or heteroalkyl group. Z can also be a $C_3$ to $C_7$ saturated or unsaturated cyclic alkyl or cyclic heteroalkyl, a substituted or unsubstituted aryl or heteroaryl group, or a substituted or unsubstituted alkaryl (the alkyl is a $C_1$ to $C_{20}$ saturated or unsaturated alkyl) or heteroalkaryl group. For substituted compounds, the substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio. Typically, P—OH is polyethylene glycol (PEG) or monomethoxy polyethylene glycol (mPEG) having a molecular weight of 5,000 to 40,000 Daltons (Da).

For example, the synthesis of mPEG-O-2-methylpropionaldehyde is outlined in Scheme II.

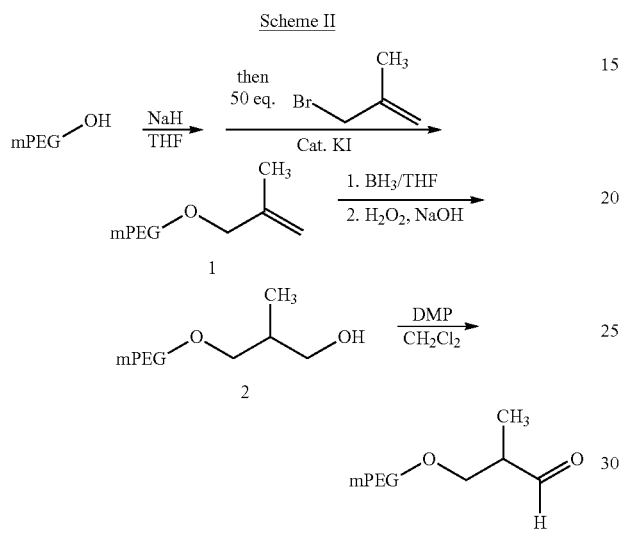

mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 3-bromo-2-methylpropene (3.34 g, 5 mmol) and a catalytic amount of KI were then added to the mixture. The resulting mixture was heated to reflux for 16 h. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to ether (150 mL) drop-wise. The resulting white precipitate was collected, yielding 1.9 g of compound 1. $^1$HNMR ($CDCl_3$, 400 MHz) showed δ 4.98 (s, 1H), 4.91 (s, 1H), 1.74 (s, 3H).

To compound 1 (1.9 g, 0.1 mmol) in THF (20 mL) and $CH_2Cl_2$ (2 mL) at 0° C., was added $BH_3$ in THF (1.0 M, 3.5 mL). The mixture was stirred in an ice bath for 1 h. To this mixture, NaOH was added slowly (2.0 M, 2.5 mL), followed by 30% $H_2O_2$ (0.8 mL). The reaction was warmed to room temperature and stirred for 16 h. The above work-up procedure was followed ($CH_2Cl_2$, precipitated from ether) to yield 1.8 g of 2 as a white solid. $^1$HNMR ($CDCl_3$, 400 MHz) showed δ 1.80 (m, 1H), 0.84 (d, 3H).

Compound 2 (250 mg) was dissolved in $CH_2Cl_2$ (2.5 mL) and Dess-Martin periodinate (DMP; 15 mg) was added with stirring for 30 min at room temperature. To the mixture was added saturated $NaHCO_3$ and $Na_2S_2O_3$ (2 mL) and the mixture was stirred at room temperature for 1 h. The above work-up procedure was followed to give 3 (mPEG-O-2-methylpropionaldehyde, 120 mg) as a white solid. $^1$HNMR ($CDCl_3$, 400 MHz) showed δ 9.75 (s, 1H), 2.69 (m, 1H), 1.16 (d, 3H).

A similar procedure is followed for aromatic alcohols, as shown in Scheme III:

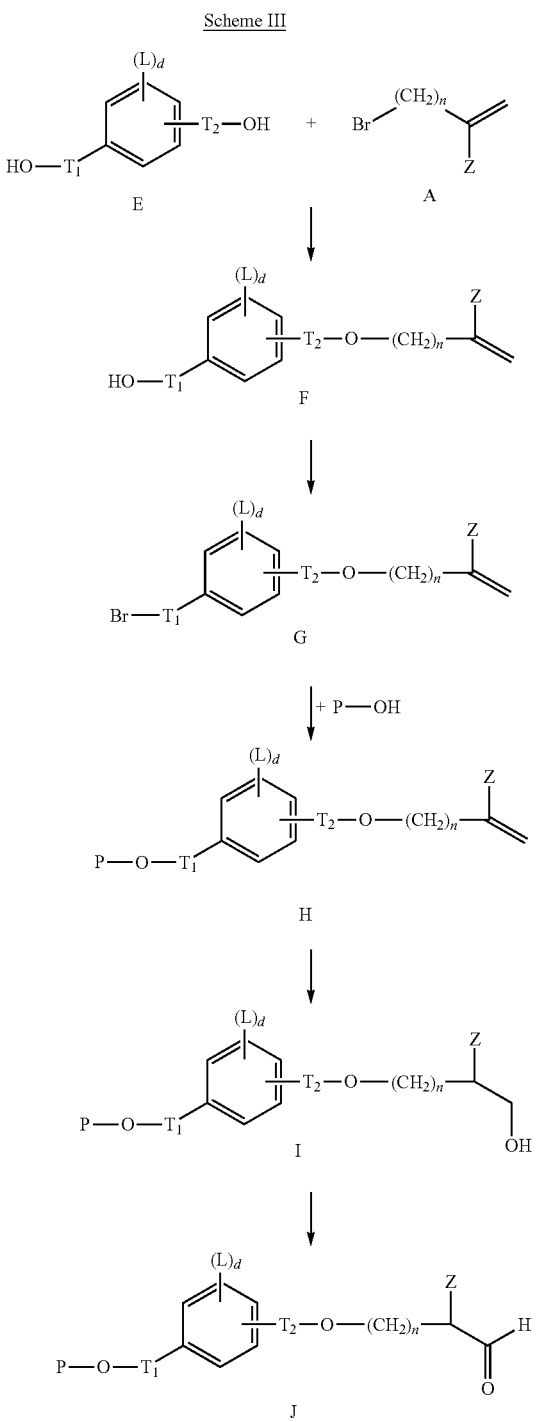

In general, the aromatic alcohol (E) is reacted with the alkyl halide (A) to form the mono ether (F). The remaining alcohol group of compound F is then converted to the halide (e.g., bromide) in Compound G, which is reacted with the polyalkylene glycol (P—OH) to give the ether (H). This compound is then converted to the aldehyde (J) through a hydroboration to the primary alcohol (I) followed by oxidation. In these compounds, n is an integer from zero to five, d is zero or an integer from one to four, and Z can be a straight- or branched-chain, saturated or unsaturated $C_1$ to $C_{20}$ alkyl or heteroalkyl group. Z can also be a $C_3$ to $C_7$ saturated or unsaturated cyclic alkyl or cyclic heteroalkyl, a substituted or unsubstituted aryl or heteroaryl group or a substituted or unsubstituted alkaryl (the alkyl is a $C_1$ to $C_{20}$ saturated or unsaturated alkyl) or heteroalkaryl group. For substituted compounds, the substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulthydryl, sulfate, sulfonate, sulfamoyl, sulfonamido, sulfonyl, heterocyclyl, aralkyl, aromatic moiety, heteroaromatic moiety, imino, silyl, ether, or alkylthio.

Additionally, $T_1$ and $T_2$ are, independently, absent, or a straight- or branched-chain, saturated or unsaturated $C_1$ to $C_{20}$ alkyl or heteroalkyl group, and can be ortho, meta, or para to each other. Each L (when present) is, independently, a straight- or branched-chain, saturated or unsaturated $C_1$ to $C_{20}$ alkyl or heteroalkyl group, $C_3$ to $C_7$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group. The substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

Usually, P—OH is polyethylene glycol (PEG) or monomethoxy polyethylene glycol (mPEG) having a molecular weight of 5,000 to 40,000 Da.

For example, the synthesis of mPEG-O-p-methylphenyl-O-2-methylpropionaldehyde (8) is shown in Scheme IV;

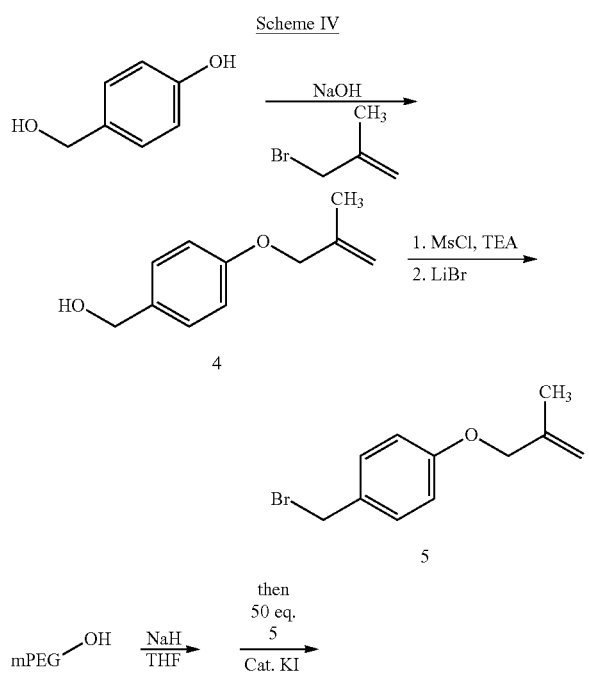

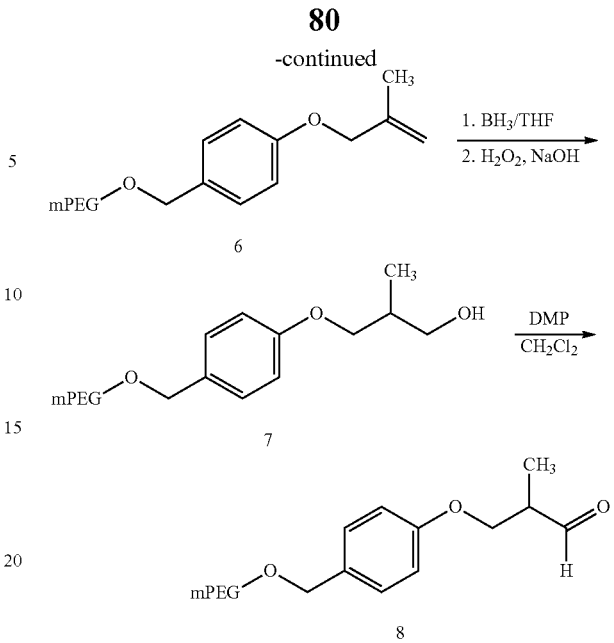

To a solution of 4-hydroxybenzylalcohol (2.4 g, 20 mmol) in THF (50 mL) and water (2.5 mL) was first added sodium hydroxide (1.5 g, 37.5 mmol) and then 3-bromo-2-methylpropene (4.1 g, 30 mmol). This reaction mixture was heated to reflux for 16 h. To the mixture was added 10% citric acid (2.5 mL) and the solvent was removed under vacuum. The residue was extracted with ethyl acetate (3×15 mL) and the combined organic layers were washed with saturated NaCl (10 mL), dried and concentrated to give compound 4. (3.3 g, 93%). $^1$HNMR (CDCl$_3$, 400 MHz) showed δ 7.29 (m, 2H), 6.92 (m, 2H), 5.14 (s, 1H), 5.01 (s, 1H), 4.56 (s, 2H), 4.46 (s, 2H), 1.85 (s, 3H).

Mesyl chloride (MsCl; 2.5 g, 15.7 mmol) and triethyl amine (TEA; 2.8 mL, 20 mmol) were added to a solution of compound 4 (2.0 g, 11.2 mmol) in CH$_2$Cl$_2$ (25 mL) at 0° C. and the reaction was placed in the refrigerator for 16 h. A usual work-up yielded a pale yellow oil (2.5 g, 87%). $^1$HNMR (CDCl$_3$, 400 MHz) showed δ 7.31 (m, 2H), 6.94 (m, 2H), 5.16 (s, 1H), 5.01 (s, 1H), 5.03 (s, 2H), 4.59 (s, 2H), 4.44 (s, 2H), 3.67 (s, 3H), 1.85 (s, 3H). This oil (2.4 g, 9.4 mmol) was dissolved in THF (20 mL) and LiBr (2.0 g, 23.0 mmol) was added. The reaction mixture was heated to reflux for 1 h and was then cooled to room temperature. Water (2.5 mL) was added to the mixture and the solvent was removed under vacuum. The residue was extracted with ethyl acetate (3×15 mL) and the combined organic layers were washed with saturated NaCl (10 mL), dried over anhydrous Na$_2$SO$_4$, and concentrated to give the desired bromide 5 (2.3 g, 96%) as a pale yellow oil. $^1$HNMR (CDCl$_3$, 400 MHz) showed δ 7.29 (m, 2H), 6.88 (m, 2H), 5.11 (s, 1H), 4.98 (s, 1H), 4.53 (s, 2H), 4.44 (s, 2H), 1.83 (s, 3H).

mPEG-OH 20 kDa (2.0 g, 0.1 mmol, Sunbio) was treated with NaH (12 mg, 0.5 mmol) in THF (35 mL) and compound 5 (0.55 g, 22.8 mmol) was added to the mixture with a catalytic amount of K1. The resulting mixture was heated to reflux for 16 h. Water (1.0 mL) was added to the mixture and the solvent was removed under vacuum. To the residue was added CH$_2$Cl$_2$ (25 mL) and the organic layer was separated, dried over anhydrous Na$_2$SO$_4$, and the volume was reduced to approximately 2 mL. Drop-wise addition to an ether solution (150 mL) resulted in a white precipitate which was collected to yield 6 (1.5 g) as a white powder. $^1$HNMR (CDCl$_3$, 400

MHz) showed δ 7.21 (d, 2H), 6.90 (d, 2H), 5.01 (s, 1H), 4.99 (s, 1H), 4.54 (s, 2H), 4.43 (s, 2H), 1.84 (s, 3H).

To a solution of compound 6 (1.0 g, 0.05 mmol) in THF (10 mL) and CH$_2$Cl$_2$ (2 mL) cooled to 0° C., was added BH$_3$/THF (1.0 M, 3.5 mL) and the reaction was stirred for 1 h. A 2.0 M NaOH solution (2.5 mL) was added slowly and followed by 30% H$_2$O$_2$ (0.8 mL). The reaction mixture was allowed to warm to room temperature and stirred for 16 h. The above work-up procedure was followed (CH$_2$Cl$_2$, precipitated from ether) to yield 7 (350 mg) as a white solid. $^1$HNMR (CDCl$_3$, 400 MHz) showed δ 7.21 (d, 2H), 6.84 (d, 2H), 4.54 (s, 2H), 2.90 (m, 2 H), 1.96 (d, 3H).

Compound 7 (150 mg, 0.0075 mmol) was dissolved in CH$_2$Cl$_2$ (1.5 mL) and DMP (15 mg) was added while the reaction mixture was stirred at room temperature for 1.5 h. $^1$HNMR (CDCl$_3$, 400 MHz) showed δ 9.76 (s, 1H), 7.21 (d, 2H), 6.78 (d, 2H), 4.44 (s, 2H), 4.14 (m, 2H), 2.85 (m, 1H), 1.21 (d, 3H). To the mixture was added saturated NaHCO$_3$ (0.5 mL) and Na$_2$S$_2$O$_3$ (0.5 mL) and stirring continued at room temperature for 1 h. The above work-up procedure was followed (CH$_2$Cl$_2$ solution, precipitated from ether) to give 8 (92 mg) as a white solid.

Similarly, mPEG-O-m-methylphenyl-O-2-methylpropionaldehyde (9) was synthesized as outlined in Scheme V.

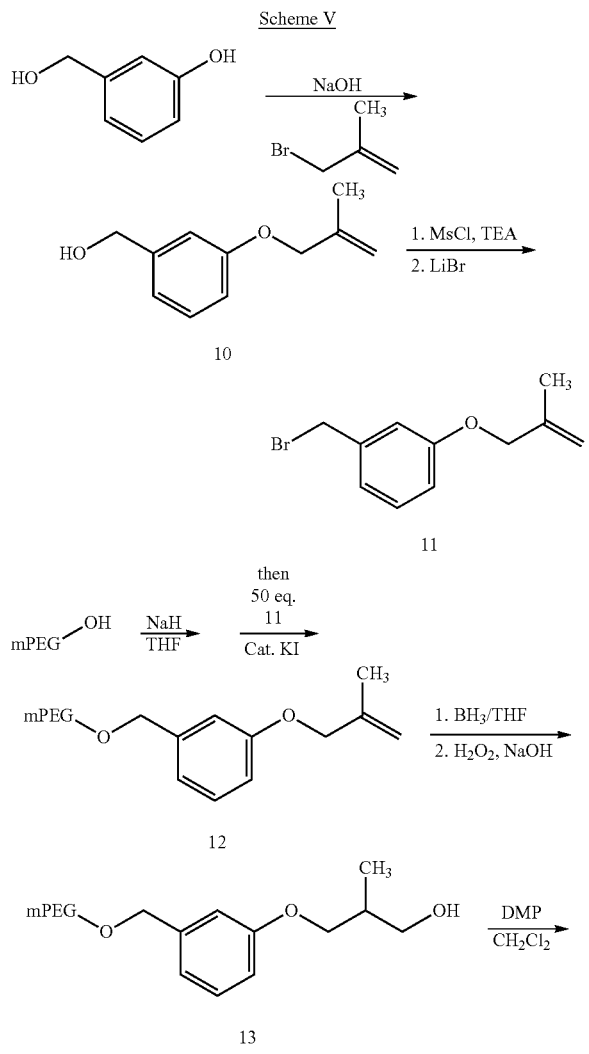

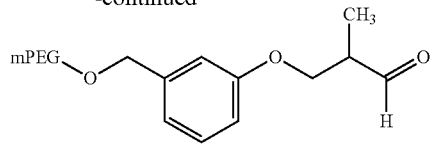

To a solution of 3-hydroxybenzylalcohol (2.4 g, 20 mmol) in THF (50 mL) and water (2.5 mL) was first added sodium hydroxide (1.5 g, 37.5 mmol) and then 3-bromo-2-methylpropene (4.1 g, 30 mmol). This reaction mixture was heated to reflux for 16 h. To the mixture was added 10% citric acid (2.5 mL) and the solvent was removed under vacuum. The residue was extracted with ethyl acetate (3×15 mL) and the combined organic layers were washed with saturated NaCl (10 mL), dried and concentrated to give compound 10 (3.2 g, 90%). $^1$HNMR (CDCl$_3$, 400 MHz) showed δ 7.26 (m, 1H), 6.94 (m, 2H), 6.86 (m, 1H), 5.11 (s, 1H), 5.01 (s, 1H), 4.61 (s, 1H), 4.44 (s, 2H), 1.82 (s, 3H).

MsCl (2.5 g, 15.7 mmol) and TEA (2.8 mL, 20 mmol) were added to a solution of compound 10 (2.0 g, 11.2 mmol) in CH$_2$Cl$_2$ (25 mL) at 0° C. and the reaction was placed in the refrigerator for 16 h. A usual work-up yielded a pale yellow oil (2.5 g, 87%). $^1$HNMR (CDCl$_3$, 400 MHz) showed δ 7.31 (m, 1H), 7.05 (m, 2H), 6.91 (m, 1H), 5.16 (s, 1H), 5.04 (s, 1H), 4.59 (s, 1H), 4.46 (s, 2H), 3.71 (s, 3H), 1.84 (s, 3H). This oil (2.4 g, 9.4 mmol) was dissolved in THF (20 mL) and LiBr (2.0 g, 23.0 mmol) was added. The reaction mixture was heated to reflux for 1 h and was then cooled to room temperature. To the mixture was added water (2.5 mL) and the solvent was removed under vacuum. The residue was extracted with ethyl acetate (3×15 mL) and the combined organic layers were washed with saturated NaCl (10 mL), dried over anhydrous Na$_2$SO$_4$, and concentrated to give the desired bromide 11 (2.2 g, 92%) as a pale yellow oil. $^1$HNMR (CDCl$_3$, 400 MHz) showed δ 7.29 (m, 1H), 6.98 (m, 2H), 6.85 (m, 1H), 5.14 (s, 2H), 4.98 (s, 2H), 4.50 (s, 2H), 4.44 (s, 2H), 1.82 (d, 3H).

mPEG-OH 20 kDa (2.0 g, 0.1 mmol, Sunbio) was treated with NaH (12 mg, 0.5 mmol) in THF (35 mL) and compound 11 (0.55 g, 22.8 mmol) was added to the mixture with a catalytic amount of KI. The resulting mixture was heated to reflux for 16 h. Water (1.0 mL) was added to the mixture and the solvent was removed under vacuum. To the residue was added CH$_2$Cl$_2$ (25 mL) and the organic layer was separated, dried over anhydrous Na$_2$SO$_4$, and the volume was reduced to approximately 2 mL. Drop-wise addition to an ether solution (150 mL) resulted in a white precipitate which was collected to yield 12 (1.8 g) as a white powder. $^1$HNMR (CDCl$_3$, 400 MHz) showed δ 7.19 (m, 1H), 6.88 (m, 2H), 6.75 (m, 1H), 4.44 (s, 2H), 4.10 (m, 2H), 1.82 (d, 3H).

To a solution of compound 12 (1.0 g, 0.05 mmol) in THF (7.5 mL) and CH$_2$Cl$_2$ (2.5 mL) cooled to 0° C., was added BH$_3$THF (1.0 M, 3.5 mL) and the reaction was stirred for 1 h. A 2.0 M NaOH solution (3 mL) was added slowly, followed by 30% H$_2$O$_2$ (0.85 mL). The reaction mixture was allowed to warm to room temperature and stirred for 16 h. The above work-up procedure was followed (CH$_2$Cl$_2$, precipitated from ether) to yield 13 (450 mg) as a white solid. $^1$HNMR (CDCl$_3$, 400 MHz) showed δ 7.15 (m, 1H), 6.84 (m, 2H), 6.69 (m, 1H), 4.50 (s, 2H), 2.90 (m, 2 H), 1.95 (d, 3H).

Compound 13 (200 mg, 0.01 mmol) was dissolved in CH$_2$Cl$_2$ (1.5 mL) and DMP (20 mg) was added while the reaction mixture was stirred at room temperature for 1 h. $^1$HNMR (CDCl$_3$, 400 MHz) showed δ 9.74 (s, 1H), 7.17 (m, 1H), 6.86 (m, 2H), 6.74 (m, 1H), 4.48 (s, 2H), 4.15 (m, 2H), 2.78 (m, 1H), 1.22 (d, 3H). To the mixture was added saturated NaHCO$_3$ (0.5 mL) and Na$_2$S$_2$O$_3$ (0.5 mL) and stirring continued at room temperature for 1 h. The above work-up procedure was followed (CH₂Cl₂ solution, precipitated from ether) to give 9 (142 mg) as a white solid.

B) Generation via Reaction with Aromatic Alcohols

Activated polyalkylene glycols are synthesized by a Mitsunobu reaction between a polyalkylene glycol having a free terminal hydroxyl functionality and an aromatic alcohol. The reaction scheme is outlined in Scheme VI.

Scheme VI

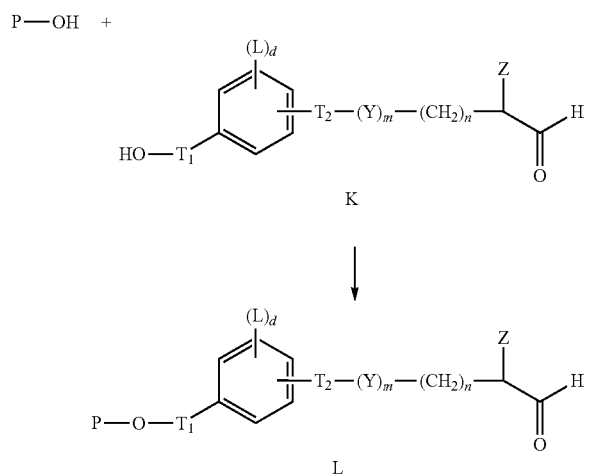

The polyalkylene glycol (P—OH) is reacted with an alcohol (K) to form the ether (L). In these compounds, m is zero or one, d is zero or an integer from one to four, and n is zero or an integer from one to five. Y is O, S, CO, CO₂, COS, SO, SO₂, CONR', SO₂NR', and NR'. T₁ and T₂ are, independently, absent, or a straight- or branched-chain, saturated or unsaturated C₁ to C₂₀ alkyl or heteroalkyl group.

R' and Z are, independently, hydrogen, a straight- or branched-chain, saturated or unsaturated C₁ to C₂₀ alkyl or heteroalkyl group.

Each L (if present) is, independently, a straight- or branched-chain, saturated or unsaturated C₁ to C₂₀ alkyl or heteroalkyl group, C₃ to C₇ saturated or unsaturated cyclic alkyl or cyclic heteroalkyl, a substituted or unsubstituted aryl or heteroaryl group or a substituted or unsubstituted alkaryl. The alkyl is a C₁ to C₂₀ saturated or unsaturated alkyl or heteroalkaryl group, and the substituents can be halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, aromatic moiety, heteroaromatic moiety, imino, silyl, ether, or alkylthio.

P is a polyalkylene glycol polymer. Usually, P—OH is polyethylene glycol (PEG) or monomethoxy polyethylene glycol (mPEG) having a molecular weight of 5,000 to 40,000 Da.

For example, a synthesis of mPEG-O-p-phenylacetaldehyde (16) is outlined in Scheme VII.

Scheme VII

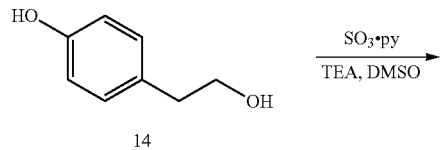

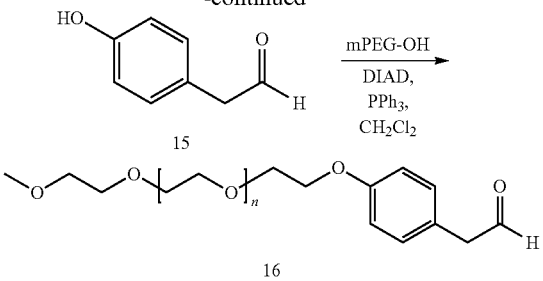

4-hydroxyphenylacetaldehyde (15) was synthesized as described in *Heterocycles*, 2000, 53, 777-784. 4-Hydroxyphenethyl alcohol (Compound 141.0 g, 7.3 mmol, Aldrich) was dissolved in dimethylsulfoxide (8 mL, Aldrich). With stirring, TEA (2.2 mL, 16 mmol, Aldrich) was added slowly. Pyridine-sulfur trioxide (SO₃.py) complex (2.5 g, 16 mmol, Aldrich) was completely dissolved in dimethylsulfoxide (9 mL, Aldrich) and this solution was added drop-wise to the alcohol, with vigorous stirring. After stirring for 1 h at room temperature, the reaction was diluted with CH₂Cl₂, then washed with ice-cold water. The organic layer was dried over Na₂SO₄, filtered, and concentrated to dryness. Purification using silica gel chromatography with hexane-ethyl acetate as eluent (5:1, then 2:1) yielded 488 mg (49%) of 4-hydroxyphenylacetaldehyde (15).

mPEG-OH 20 kDa (101 mg, 0.005 mmol) and 4-hydroxyphenylacetaldehyde (15) (39 mg, 0.29 mmol) were azeotroped four times with toluene, then taken up in anhydrous CH₂Cl₂ (2 mL, Aldrich). To this solution was added triphenylphosphine (PPh₃; 66 mg, 0.25 mmol, Aldrich) and then diisopropylazodicarboxylate (DIAD; 49 µL, 0.25 mmol, Aldrich) with stirring. After 3 days of stirring at room temperature, the reaction mixture was added drop-wise to vigorously-stirred diethyl ether. The resulting precipitate was isolated by filtration and washed three times with diethyl ether. The crude material was taken up in CH₂Cl₂ and washed with water. The organic layer was dried over Na₂SO₄, filtered, and concentrated to dryness. The material was taken up in minimum CH₂Cl₂, then precipitated by adding drop-wise to stirred diethyl ether. This material was collected by filtration, washed flute times with diethyl ether and dried to give 63 mg (62%) of mPEG-O-p-phenylacetaldehyde A synthesis of mPEG-O-p-phenylpropionaldehyde (17) was prepared in a similar manner.

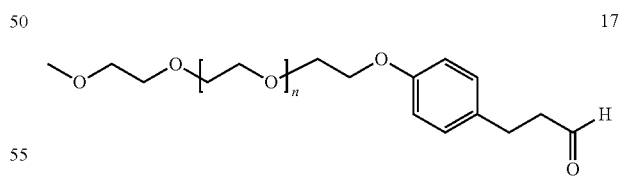

4-hydroxyphenylpropionaldehyde was prepared by a synthesis analogous to that for 4-hydroxyphenylacetaldehyde (*Heterocycles*, 2000, 53, 777-784). 3-(4-Hydroxyphenyl)-1-propanol (1.0 g, 6.6 mmol, Aldrich) was dissolved in dimethylsulfoxide (8 mL, Aldrich). TEA (2.0 mL, 14 mmol, Aldrich) was added slowly with stirring. Pyridine-sulfur trioxide (SO₃.py) complex (2.3 g, 15 mmol, Aldrich) was completely dissolved in dimethylsulfoxide (9 mL, Aldrich) and this solution was added drop-wise to the alcohol, with vigorous stirring. After stirring for 1 h at room temperature, the reaction was diluted with CH$_2$Cl$_2$, then washed with ice-cold water. The organic layer was dried over Na$_2$SO$_4$, filtered, and concentrated to dryness. Purification using silica gel chromatography with hexane-ethyl acetate as eluent (5:1, then 2:1) yielded 745 mg (75%) of 4-hydroxyphenylpropionaldehyde.

mPEG-OH 20 kDa (100 mg, 0.005 mmol) and 4-hydroxyphenylpropionaldehyde (40 mg, 0.27 mmol) were azeotroped four times with toluene, then taken up in anhydrous CH$_2$Cl$_2$ (2 mL, Aldrich). To this solution was added triphenylphosphine (66 mg, 0.25 mmol, Aldrich) and then diisopropylazodicarboxylate (49 µL, 0.25 mmol, Aldrich) with stirring. After 3 days stirring at room temperature, the reaction mixture was added drop-wise to vigorously-stirred diethyl ether. The resulting precipitate was isolated by filtration and washed three times with diethyl ether. The crude material was taken up in CH$_2$Cl$_2$ and washed with water. The organic layer was dried over Na$_2$SO$_4$, filtered, and concentrated to dryness. The material was taken up in minimum CH$_2$Cl$_2$, then precipitated by adding drop-wise to stirred diethyl ether. This material was collected by filtration, washed three times with diethyl ether and dried to give 60 mg (60%) of mPEG-O-p-phenylpropionaldehyde (17).

mPEG-O-m-phenylacetaldehyde (18) was also prepared in this way.

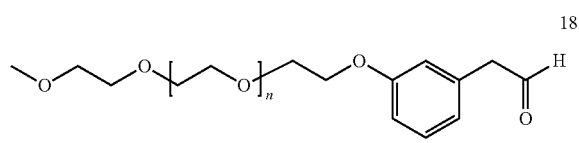

18

3-hydroxyphenylacetaldehyde was prepared by a synthesis analogous to that of 4-hydroxyphenylacetaldehyde (*Heterocycles,* 2000, 53, 777-784). 3-Hydroxyphenethyl alcohol (1.0 g, 7.5 mmol, Aldrich) was dissolved in dimethylsulfoxide (8 mL, Aldrich). TEA (2.0 mL, 14 mmol, Aldrich) was added slowly with stirring. Pyridine-sulfur trioxide (SO$_3$.py) complex (2.4 g, 15 mmol, Aldrich) was completely dissolved in dimethylsulfoxide (8 mL, Aldrich) and this solution was added drop-wise to the alcohol, with vigorous stirring. After stirring for 1 h at room temperature, the reaction was quenched with ice-cold water, then extracted with CH$_2$Cl$_2$. The organic layer was dried over Na$_2$SO$_4$, filtered, and concentrated to dryness.

Purification using silica gel chromatography with hexane-ethyl acetate as eluent (3:1, then 1:1) yielded 225 mg (22%) of 3-hydroxyphenylacetaldehyde.

mPEG-OH 20 kDa (307 mg, 0.015 mmol) and 3-hydroxyphenylacetaldehyde (117 mg, 0.86 mmol) were azeotroped four times with toluene, then taken up in anhydrous CH$_2$Cl$_2$ (5 mL, Aldrich). To this solution was added triphenylphosphine (200 mg, 0.76 mmol, Aldrich) and then diisopropylazodicarboxylate (147 µL, 0.75 mmol, Aldrich) with stirring. After 3 days of stirring at room temperature, the reaction mixture was added drop-wise to vigorously-stirred diethyl ether. The resulting precipitate was isolated by filtration and washed three times with diethyl ether and dried to yield 284 mg (93%) of mPEG-O-m-phenylacetaldehyde (18).

Chiral PEG-cinnamate-N-hydroxy succinimate (NHS) compounds are generated, for example, as shown in Schemes VIM and IX:

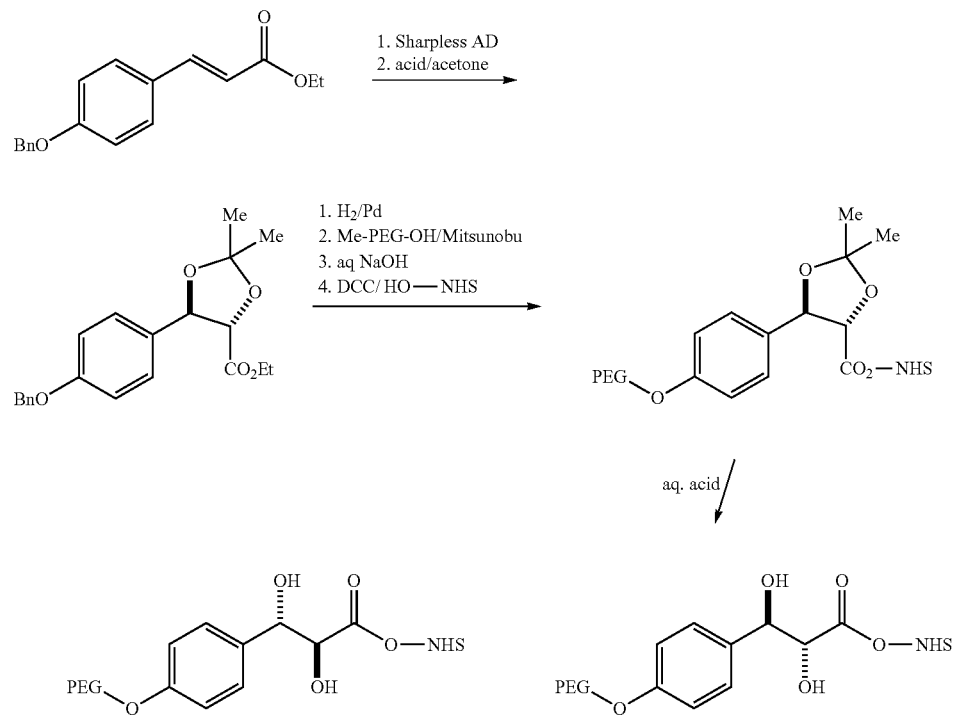

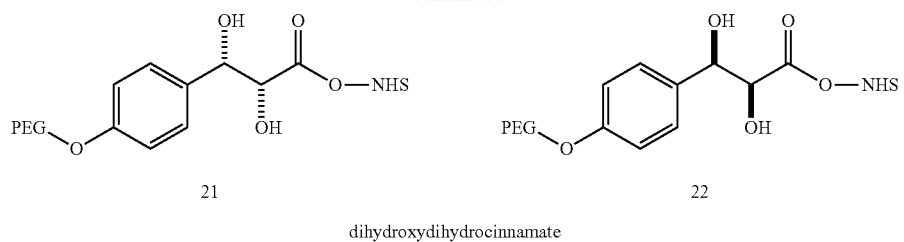
21  22
dihydroxydihydrocinnamate
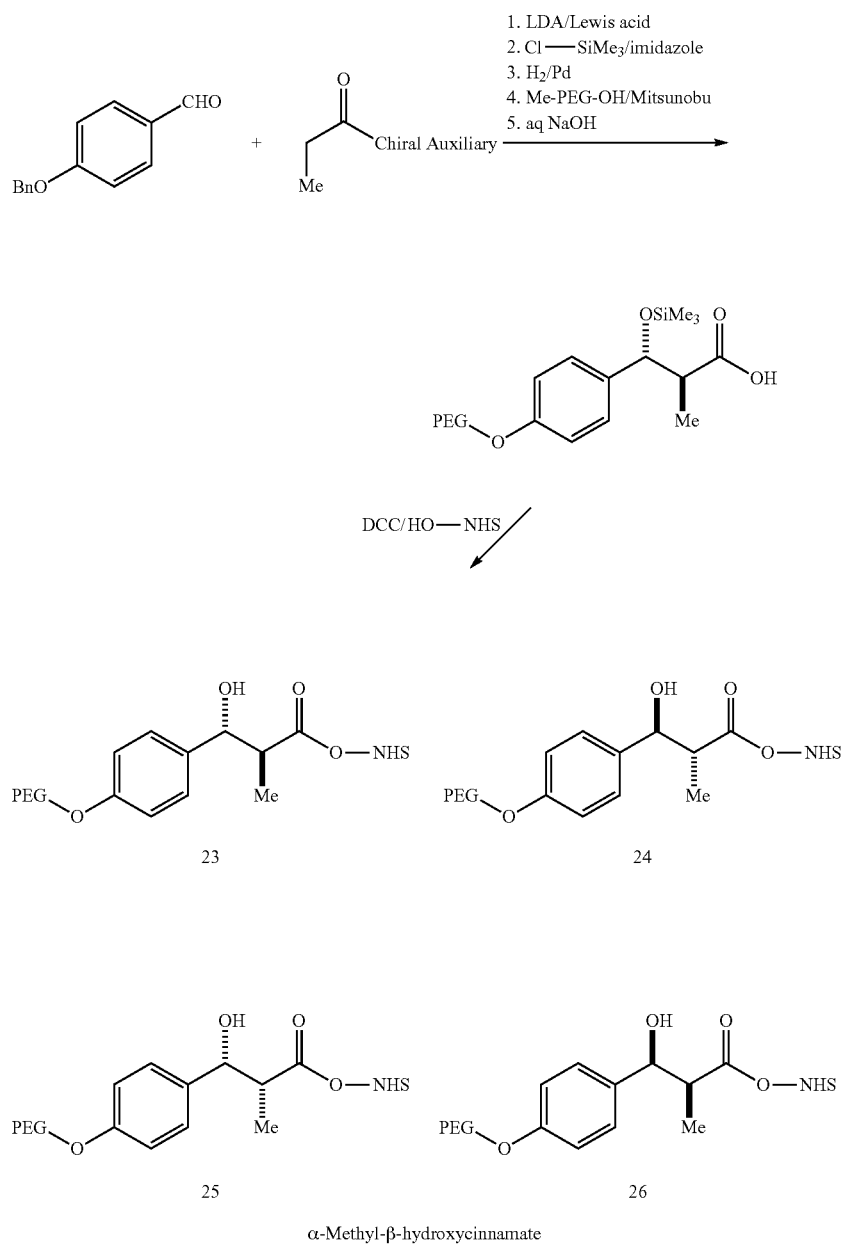
α-Methyl-β-hydroxycinnamate PEG-Dihydrourocanate-NHS compounds are also generated via a Mitsunobu reaction, as shown in Scheme X:
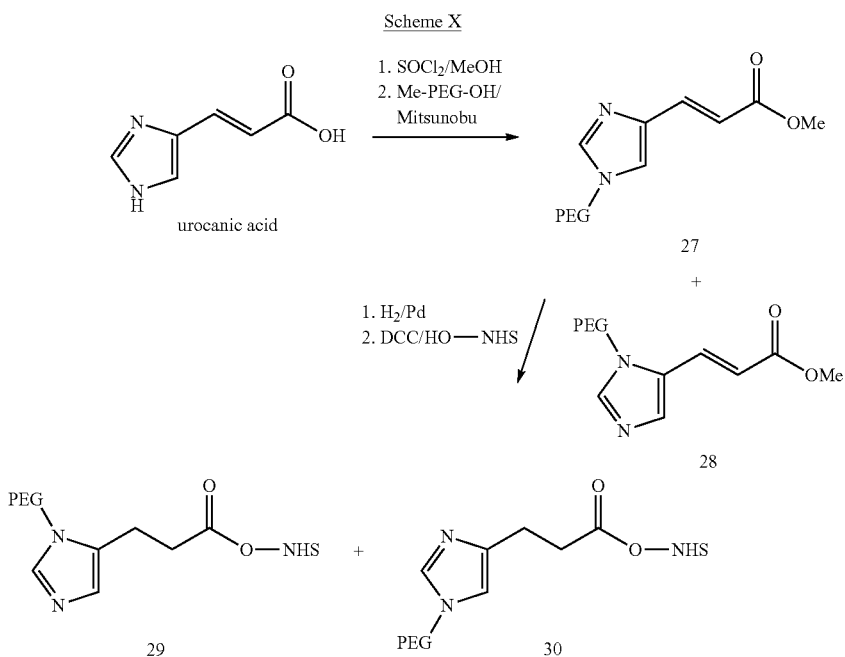
PEG-Dihydrocinnamate-NHS compounds are also generated from an aromatic alcohol as shown in Scheme XI:
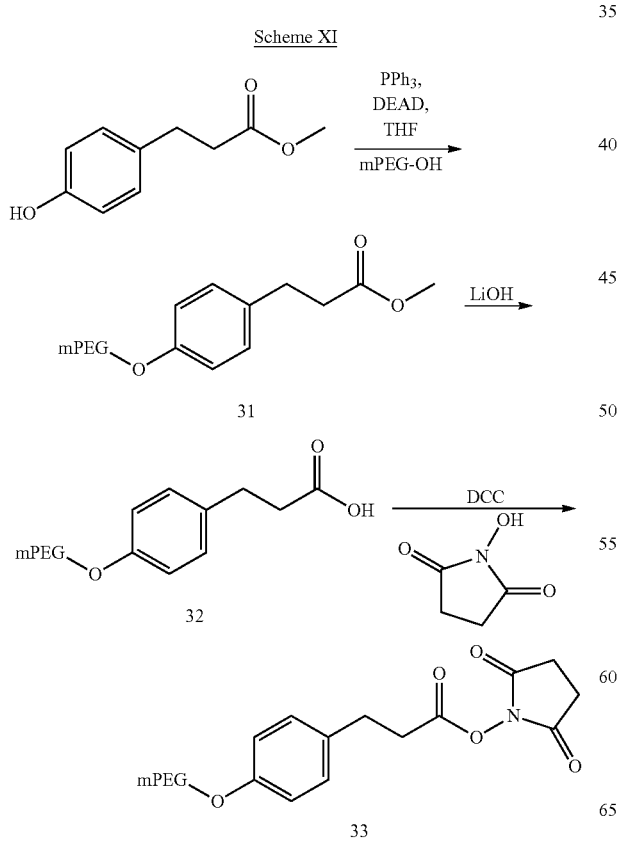
PEG-benzofurans and PEG-indoles are generated as shown in Schemes XII and XIII:
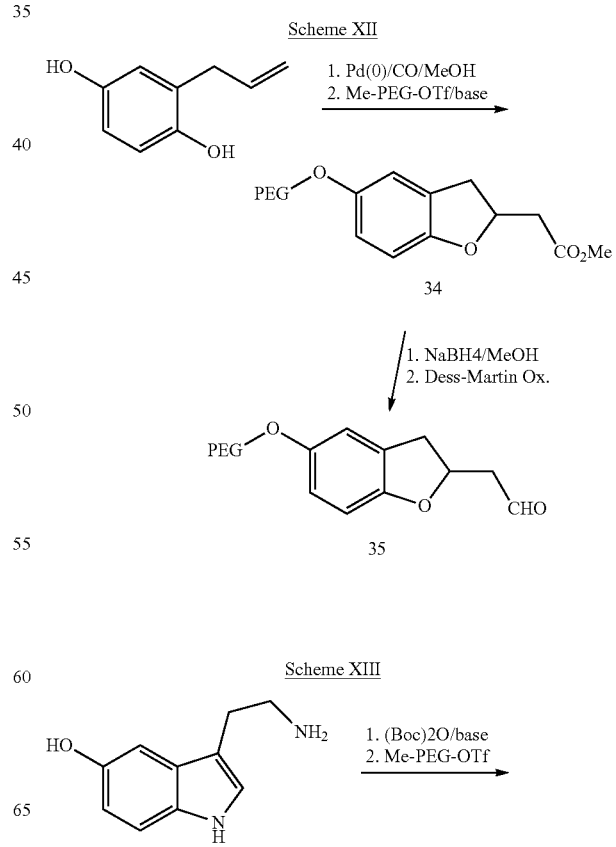

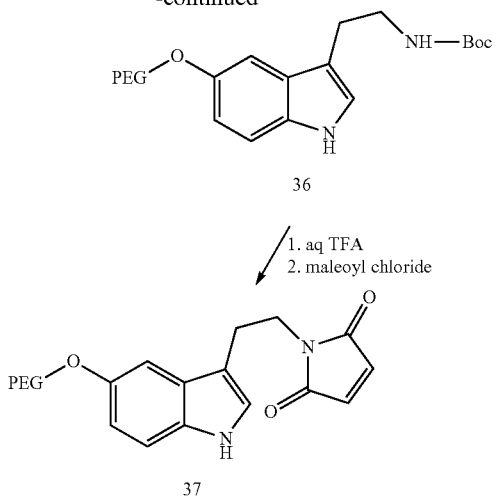

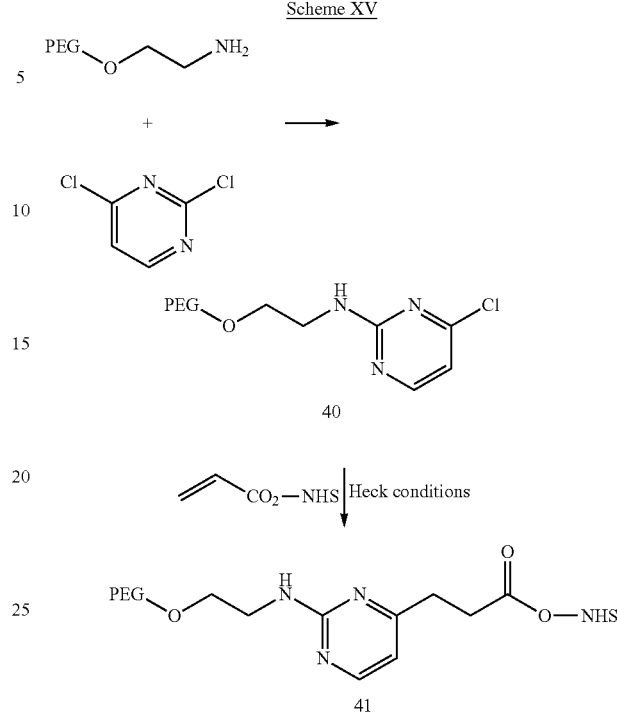

C) Generation via Reaction of PEG-Amines

PEG amines are reacted with alkyl halides to generate PEG-amides. An example of the generation of a PEG-amide-bicyclooctane-NHS conjugate is shown in Scheme XIV:

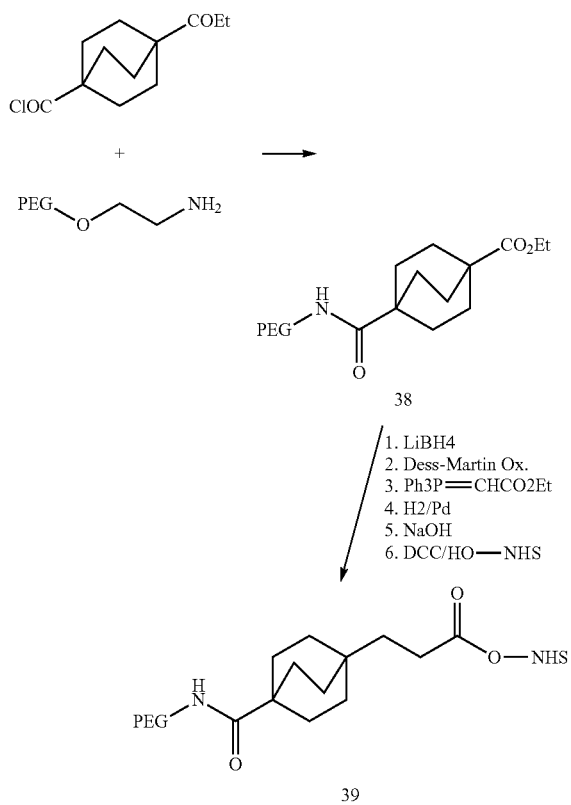

A PEG-primary amine is conjugated with an aryl-halide to form a PEG-secondary amine conjugate, which is then reacted under Heck conditions (a stereospecific Palladium-catalyzed coupling of an alkene with an organic halide or triflate lacking sp$^3$ hybridized β-hydrogens) with an NHS-alkene to form the desired PEG-conjugate. The synthesis of a pyrimidine-containing conjugate is shown in Scheme XV:

PEG-sulfonamide conjugates are also synthesized in this manner, as shown in Scheme XVI:

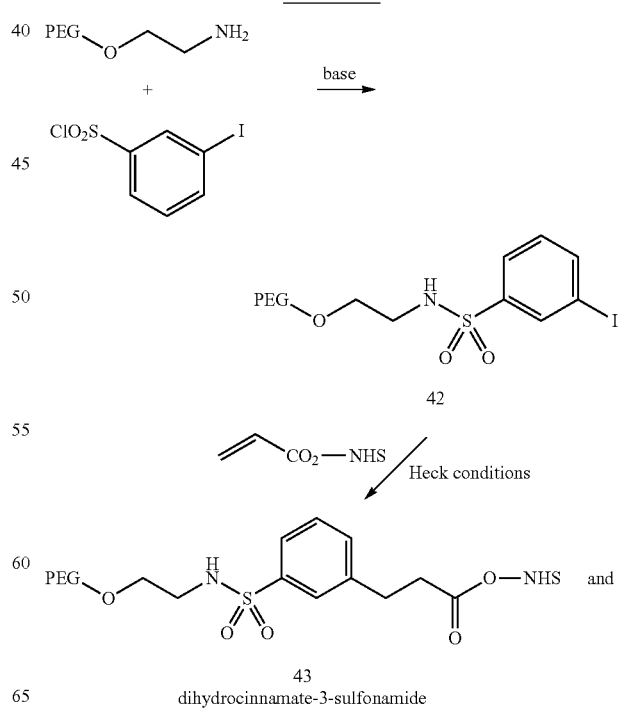

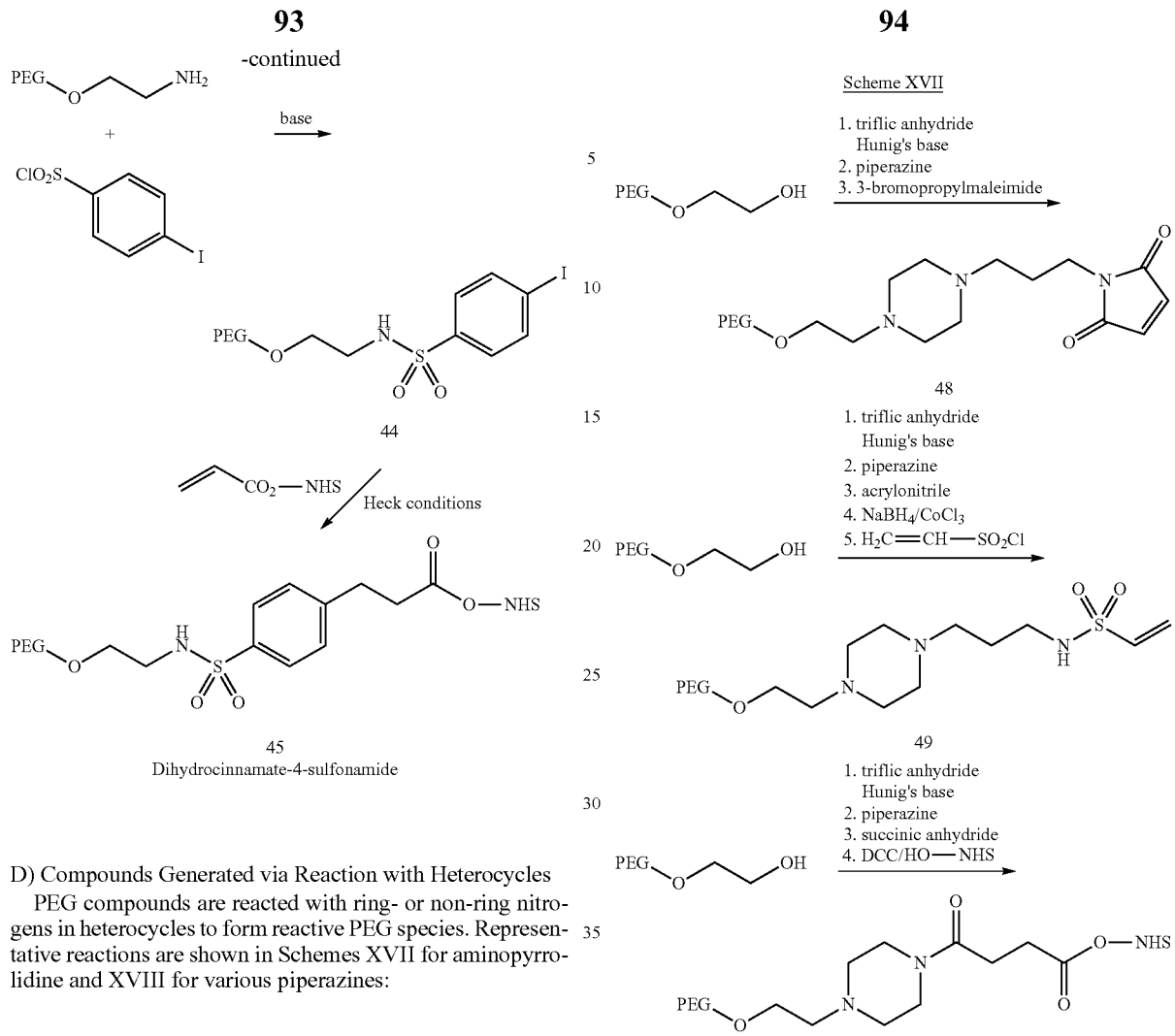

D) Compounds Generated via Reaction with Heterocycles

PEG compounds are reacted with ring- or non-ring nitrogens in heterocycles to form reactive PEG species. Representative reactions are shown in Schemes XVII for aminopyrrolidine and XVIII for various piperazines:

Example 2

Preparation of Peptide Conjugates

The peptide conjugates according to the present invention can be prepared by reacting a protein with an activated PGC molecule. For example, interferon (IFN) can be reacted with a PEG-aldehyde in the presence of a reducing agent (e.g., sodium cyanoborohydride) via reductive alkylation to produce the PEG-protein conjugate, attached via an amine linkage. See, e.g., European Patent 0154316 B1.

Human IFN-β-1a was PEGylated with the following activated polyalkylene glycols of the invention: 20 kDa mPEG-O-2-methylpropionaldehyde, 20 kDa mPEG-O-p-methylphenyl-0-2-methylpropionaldehyde, 20 kDa mPEG-O-m-methylphenyl-O-2-methylpropionaldehyde, 20 kDa mPEG-O-p-phenylacetaldehyde, 20 kDa mPEG-O-p-phenylpropionaldehyde, and 20 kDa mPEG-O-m-phenylacetaldehyde. The PEGylated proteins were purified to homogeneity from their respective reaction mixtures and subjected to a series of characterization tests to ascertain the identity, purity, and potency of the modified proteins.

A detailed description of the preparation and characterization of human IFN-β-1a modified with 20 kDa mPEG-O-2- methylpropionaldehyde, 20 kDa mPEG-O-m-methylphenyl-O-2-methylpropionaldehyde, and 20 kDa mPEG-O-p-phenylacetaldehyde follows.

A) Preparation and Characterization of 20 kDa mPEG-O-2-methylpropionaldehyde-modified IFN-β-1a Human IFN-β-1a was PEGylated at its N-terminus with 20 kDa mPEG-O-2-methylpropionaldehyde. The product of the reductive alkylation chemistry used to incorporate the PEG onto the IFN-β-1a backbone resulted in the formation of an amine linkage which is extremely stable against degradation. The PEGylated IFN-β-1a was subjected to extensive characterization, including analysis by SDS-PAGE, size exclusion chromatography (SEC), peptide mapping, and assessment of activity in an in vitro antiviral assay. The purity of the product, as measured by SDS-PAGE and SEC, was greater than 90%. In the PEGylated sample there was no evidence of aggregates. Residual levels of unmodified IFN-β-1a in the product were below the limit of quantitation, but appear to represent about 1% of the product. The specific activity of the PEGylated IFN-β-1a in the antiviral activity assay was reduced approximately 2-fold compared to the unmodified IFN-β-Ia ($EC_{50}$=32 pg/mL for 20 kDa mPEG-O-2-methylpropionaldehyde-modified IFN-β-1a versus $EC_{50}$=14 pg/mL for unmodified IFN-β-1a). The PEGylated IFN-β-1a bulk was formulated at 30 μg/mL in phosphate-buffered saline (PBS) pH 7.3, containing 14 mg/mL human serum albumin (HSA), similar to the formulation used for AVONEX® (Biogen, Cambridge, Mass.) which has been subjected to extensive characterization. The material was supplied as a frozen liquid which was stored at −70° C.

The properties of 20 kDa mPEG-O-2-methylpropionaldehyde-modified IFN-β-1a are summarized in Table 1:

TABLE 1

Properties of 20 kDa mPEG-O-2-methylpropionaldehyde-modified IFN-β-1a

| | |
|---|---|
| Pegylation efficiency | >90% |
| IFN-β-1a/PEG ratio | 1:1 |
| Purity | >90% |
| Site of attachment | N-terminus |
| Antiviral activity $EC_{50}$ | 32 pg/mL |

1. Preparation of 20 kDa mPEG-O-2-methylpropionaldehyde-modified IFN-β-1a. 10 mL of nonformulated AVONEX® (IFN-β-1a bulk intermediate, a clinical batch of bulk drug that passed all tests for use in humans, at 250 μg/mL in 100 mM sodium phosphate pH 7.2, 200 mM NaCl) was diluted with 12 mL of 165 mM MES pH 5.0 and 50 μL of 5 N HCl. The sample was loaded onto a 300 μL SP-Sepharose FF column (Pharmacia). The column was washed with 3×300 μl, of 5 mM sodium phosphate pH 5.5, 75 mM NaCl, and the protein was eluted with 5 mM sodium phosphate pH 5.5, 600 mM NaCl. Elution fractions were analyzed for their absorbance at 280 nm and the concentration of IFN-β-1a in the samples estimated using an extinction coefficient of 1.51 for a 1 mg/mL solution. The peak fractions were pooled to give an IFN-β-1a concentration of 3.66 mg/mL, which was subsequently diluted to 1.2 mg/mL with water.

To 0.8 mL of the IFN-β-1a from the diluted SP-Sepharose eluate pool, 0.5 M sodium phosphate pH 6.0 was added to 50 mM, sodium cyanoborohydride (Aldrich) was added to 5 mM, and 20 kDa mPEG-O-2-methylpropionaldehyde was added to 5 mg/mL. The sample was incubated at room temperature for 16 h in the dark. The PEGylated IFN-β-1a was purified from the reaction mixture on a 0.5 mL SP-Sepharose FF column as follows: 0.6 mL of the reaction mixture was diluted with 2.4 mL 20 mM MES pH 5.0, and loaded onto the SP-Sepharose column. The column was washed with sodium phosphate pH 5.5, 75 mM NaCl and then the PEGylated IFN-β-1a was eluted from the column with 25 mM MES pH 6.4, 400 mM NaCl. The PEGylated IFN-β-1'-1a was further purified on a Superose 6 HR 10/30 FPLC sizing column with 5 mM sodium phosphate pH 5.5, 150 mM NaCl as the mobile phase. The sizing column (25 mL) was run at 20 mL/h and 0.5 mL fractions were collected. The elution fractions were analyzed for protein content by absorbance at 280 nm, pooled, and the protein concentration of the pool determined. The PEGylated IFN-β-1a concentration is reported in IFN equivalents as the PEG moiety does not contribute to absorbance at 280 nm. Samples of the pool were removed for analysis, and the remainder was diluted to 30 μg/mL with HSA-containing formulation buffer, aliquoted at 0.25 mL/vial, and stored at −70° C.

2. UV spectrum of purified 20 kDa mPEG-O-2-methylpropionaldehyde-modified IFN-β-1a. The UV spectrum (240-340 nm) of 20 kDa mPEG-O-2-methylpropionaldehyde-modified IFN-β-1a was obtained using the pre-HSA-formulated bulk sample. The PEGylated sample exhibited an absorbance maximum at 278-279 nm and an absorbance minimum at 249-250 nm, consistent with that observed for the unmodified IFN-β-1a bulk intermediate. The protein concentration of the PEGylated product was estimated from the spectrum using an extinction coefficient of $\epsilon_{280}^{0.1\%}$=1.51. The protein concentration of the PEGylated bulk was 0.23 mg/mL. No turbidity was present in the sample as evident by a lack of absorbance at 320 nm.

3. Characterization of 20 kDa mPEG-O-2-methylpropionaldehyde-modified by SDS-PAGE. 4 μg of unmodified and 20 kDa mPEG-O-2-methylpropionaldehyde-modified IFN-β-1a were subjected to SDS-PAGE under reducing conditions on a 10-20% gradient gel. The gel was stained with Coomassie brilliant blue R-250, and is shown in FIG. 1 (Lane A, molecular weight markers (from top to bottom; 100 kDa, 68 kDa, 45 kDa, 27 kDa, and 18 kDa, respectively); Lane B, unmodified IFN-β-1a; Lane C, 20 kDa mPEG-O-2-methylpropionaldehyde-modified IFN-β-1a). SDS-PAGE analysis of 20 kDa mPEG-O-2-methylpropionaldehyde-modified IFN-β-1a revealed a single major band with an apparent mass of 55 kDa, consistent with modification by a single PEG. No higher mass forms resulting from the presence of additional PEG groups were detected. In the purified, PEGylated product, unmodified IFN-β-1a was detected; however, the amount is below the limit of quantitation. The level of unmodified IFN-β-1a in the preparation is estimated to account for only about 1% of the total protein.

Figure 2A:
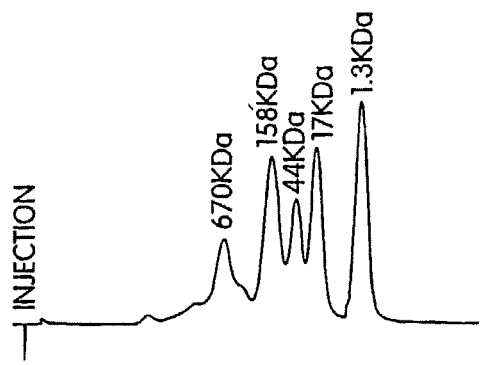
Figure 2B:
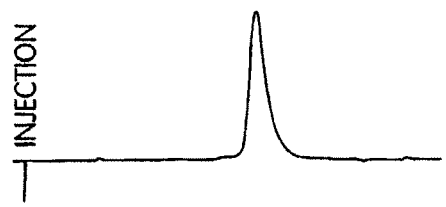
Figure 2C:

4. Characterization of 20 kDa mPEG-O-2-methylpropionaldehyde-modified IFN-β-1a by size exclusion chromatography. Unmodified and 20 kDa mPEG-O-2-methylpropionaldehyde-modified IFN-β-1a were subjected to SEC on an analytical Superose 6 HR10/30 FPLC sizing column using PBS pH 7.2 as the mobile phase. The column was run at 20 mL/h and the eluent monitored for absorbance at 280 nm, as, shown in FIG. 2: Panel A: molecular weight standards (670 kDa, thyroglobulin; 158 kDa, gamma globulin; 44 kDa, ovalbumin; 17 kDa, myoglobin; 1.3 kDa, vitamin B12), Panel B: 20 kDa mPEG-O-2-methylpropionaldehyde-modified IFN-β-1a; Panel C: unmodified IFN-β-1a. The 20 kDa mPEG-O-2-methylpropionaldehyde-modified IFN-β-1a eluted as a single sharp peak with an apparent molecular mass of approximately 200 kDa, consistent with the large hydrodynamic volume of the PEG. No evidence of aggregates was observed. Unmodified IFN-β-1a in the preparation was detected but was below the limit of quantitation. Based on the size of the peak, the unmodified IFN-β-1a accounts for 1% or less of the product, consistent with that observed using SDS-PAGE.

5. Analysis of 20 kDa mPEG-O-2-methylpropionaldehyde-modified IFN-B-1a by peptide mapping. The specificity of the PEGylation reaction was evaluated by peptide mapping. Unmodified and 20% Da mPEG-O-2-methylpropionaldehyde-modified IFN-β-1a were digested with endoproteinase Lys-C from *Achromobacter* (Wako Bioproducts) and the resulting cleavage products were fractionated by reverse-phase HPLC on a Vydac $C_4$ column using a 30 min gradient from 0 to 70% acetonitrile, in 0.1% TFA. The column eluent was monitored for absorbance at 214 nm.

All of the predicted peptides from the endoproteinase Lys-C digest of IFN-β-1a have been identified previously by N-terminal sequencing and mass spectrometry (Pepinsky et al., (2001) J Pharmacology and Experimental Therapeutics 297:1059), and, of these, only the peptide that contains the N-terminus of IFN-β-1a was altered by modification with 20 kDa mPEG-O-2-methylpropionaldehyde; as evident by its disappearance from the peptide map. The mapping data therefore indicate that the PEG moiety is specifically attached to this peptide. The data further indicate that the PEG modification is targeted at the N-terminus of the protein since only the N-terminal modification would result in the specific loss of this peptide.

B) Preparation and Characterization of 20 kDa mPEG-O-m-methylphenyl-O-2-methylpropionaldehyde-modified IFN-β-1a Human IFN-β-1a was PEGylated at the N-terminus with 20 kDa mPEG-O-m-methylphenyl-O-2-methylpropionaldehyde. The product of the reductive alkylation chemistry that was used to incorporate the PEG onto the IFN-β-1a backbone results in the formation of an amine linkage which is extremely stable against degradation. The PEGylated IFN-β-1a was subjected to extensive characterization, including analysis by SDS-PAGE, SEC, peptide mapping, and assessment of activity in an in vitro antiviral assay. The purity of the product as measured by SDS-PAGE and SEC was greater than 95%. In the PEGylated IFN-β-1a sample there was no evidence of aggregates. Residual levels of unmodified IFN-β-1a in the product were below the limit of quantitation, but appear to represent about 1% of the product. The specific activity of the PEGylated IFN-β-1a in the antiviral activity assay was reduced approximately 2-fold compared to the unmodified IFN-β-1a ($EC_{50}$=31 pg/mL for 20 kDa mPEG-O-m-methylphenyl-O-2-methylpropionaldehyde-modified IFN-β-1a versus $EC_{50}$=14 pg/mL for unmodified IFN-β-1a). The PEGylated IFN-β-1a bulk was formulated at 30 µg/mL in PBS pH 7.2 containing 15 mg/mL HSA, similar to the formulation used for AVONEX® which has been subjected to extensive characterization. The material was supplied as a frozen liquid which was stored at −70° C.

The properties of 20 kDa mPEG-O-m-methylphenyl-O-2-methylpropionaldehyde-modified IFN-β-1a are summarized in Table 2:

TABLE 2

Properties of 20 kDa mPEG-O-m-methylphenyl-O-2-methylpropionaldehyde-modified IFN-β-1a

| | |
|---|---|
| PEGylation efficiency | >80% |
| IFN-β-1a/PEG ratio | 1:1 |
| Purity | >95% |
| Site of attachment | N-terminus |
| Antiviral activity $EC_{50}$ | 31 pg/mL |

1. Preparation of 20 kDa mPEG-O-m-methylphenyl-O-2-methylpropionaldehyde-modified IFN-β-1a. 80 mL of non-formulated AVONEX® (IFN-(3-1a bulk intermediate, a clinical batch of bulk drug that passed all tests for use in humans, at 254 µg/mL in 100 mM sodium phosphate pH 7.2, 200 mM NaCl) was diluted with 96 mL of 165 mM MES pH 5.0, and 400 µl, of 5 N HCl. The sample was loaded onto a 12 mL SP-Sepharose FF column (Pharmacia). The column was washed with 6.5 mL of 5 mM sodium phosphate pH 5.5, 75 mM NaCl, and the protein was eluted with 5 mM sodium phosphate pH 5.5, 600 mM NaCl. Elution fractions were analyzed for their absorbance at 280 nm and the concentration of IFN-β-1a in the samples was estimated using an extinction coefficient of 1.51 for a 1 mg/mL solution. The peak fractions were pooled to give an IFN-β-1a concentration of 4.4 mg/mL. To 2.36 mL of the 4.4 mg/mL IFN-β-1a from the SP-Sepharose eluate pool, 0.5 M sodium phosphate pH 6.0 was added to 50 mM, sodium cyanoborohydride (Aldrich) was added to 5 mM, and 20 kDa mPEG-O-m-methylphenyl-O-2-methylpropionaldehyde, was added to 10 mg/mL. The sample was incubated at room temperature for 21 h in the dark. The PEGylated IFN-β-1a was purified from the reaction mixture on a 8.0 mL SP-Sepharose FF column as follows: 9.44 ml, of reaction mixture was diluted with 37.7 mL of 20 mM MES pH 5.0, and loaded onto the SP-Sepharose column. The column was washed with sodium phosphate pH 5.5, 75 mM NaCl and then the PEGylated IFN-β-1a was eluted from the column with 25 mM MES pH 6.4, 400 mM NaCl. The PEGylated IFN-β-1a was further purified on a Superose 6 HR 10/30 FPLC sizing column with 5 mM sodium phosphate pH 5.5, 150 mM NaCl as the mobile phase. The sizing column (25 mL) was run at 24 mL/h and 0.25 mL fractions were collected. The elution fractions were analyzed for protein content by SDS-PAGE, pooled, and the protein concentration of the pool determined. The PEGylated IFN-β-1a concentration is reported in IFN equivalents after adjusting for the contribution of the PEG to the absorbance at 280 nm using an extinction coefficient of 2 for a 1 mg/mL solution of the PEGylated IFN-β-1a. Samples of the pool were removed for analysis, and the remainder was diluted to 30 µg/mL with HSA-containing formulation buffer, aliquoted at 0.25 mL/vial, and stored at −70° C.

2. UV spectrum of purified 20 kDa mPEG-O-m-methylphenyl-O-2-methylpropionaldehyde-modified IFN-β-1a. The UV spectrum (240-340 nm) of 20 kDa mPEG-O-m-methylphenyl-O-2-methylpropionaldehyde-modified IFN-β-1a was obtained using the pre-HSA-formulated bulk sample. The PEGylated sample exhibited an absorbance maximum at 278-279 nm and an absorbance minimum at 249-250 nm, consistent with that observed for the unmodified bulk intermediate. The protein concentration of the PEGylated product was estimated from the spectrum using an extinction coefficient of $\epsilon_{280}^{0.1\%}$=2.0. The protein concentration of the PEGylated bulk was 0.42 mg/mL. No turbidity was present in the sample as evident by the lack of absorbance at 320 nm.

3. Characterization of 20 kDa mPEG-O-m-methylphenyl-O-2-methylpropionaldehyde-modified IFN-β-1a by SDS-PAGE. 2.1 µg of 20 kDa mPEG-O-m-methylphenyl-O-2-methylpropionaldehyde-modified IFN-β-1a was subjected to SDS-PAGE under reducing conditions on a 4-20% gradient gel. The gel was stained with Coomassie brilliant blue R-250. SDS-PAGE analysis of 20 kDa mPEG-O-m-methylphenyl-O-2-methylpropionaldehyde-modified IFN-β-1a revealed a single major band with an apparent mass of 55 kDa consistent with modification by a single PEG. In the purified PEGylated product unmodified IFN-β-1a was detected; however, the amount is below the limit of quantitation. It is estimated that the level of unmodified IFN-β-1a in the preparation accounts for only about 1% of the total protein.

Figure 3:
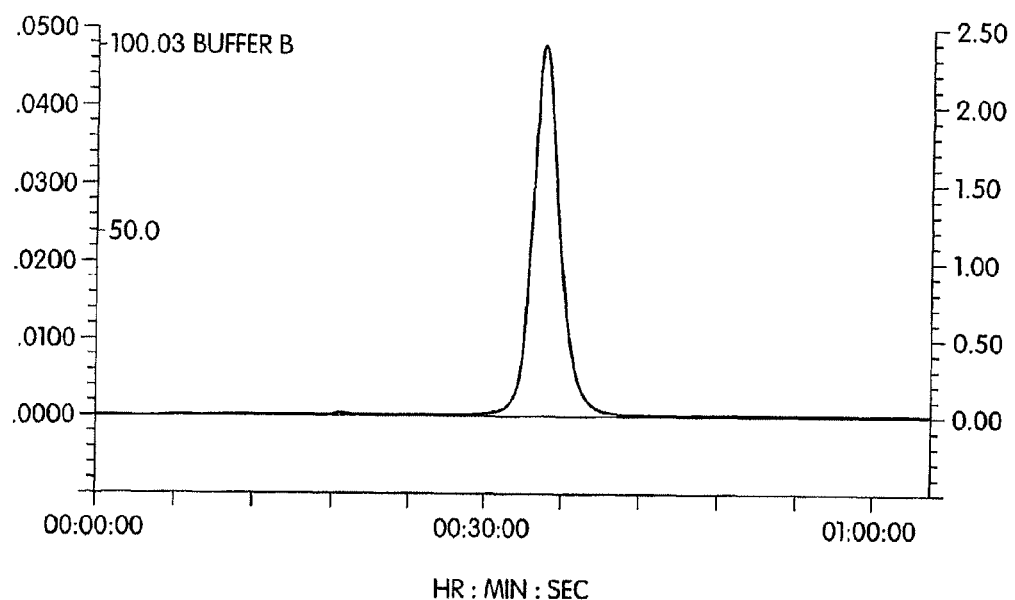

4. Characterization of 20 kDa mPEG-O-m-methylphenyl-O-2-methylpropionaldehyde-modified IFN-β-1a by size exclusion chromatography. 20 kDa mPEG-O-m-methylphenyl-O-2-methylpropionaldehyde-modified IFN-β-1a was subjected to SEC on an analytical Superose 6 HR10/30 FPLC sizing column using PBS pH 7.0 as the mobile phase. The column was run at 24 mL/h and the eluent was monitored for absorbance at 280 nm. The PEGylated IFN-β-1a eluted as a single sharp peak with no evidence of aggregates (FIG. 3).

5. Analysis of 20 kDa mPEG-O-m-methylphenyl-O-2-methylpropionaldehyde-modified IFN-β-1a by peptide mapping. The specificity of the PEGylation reaction was evaluated by peptide mapping. 13.3 μg of unmodified and 20 kDa mPEG-O-m-methylphenyl-β-2-methylpropionaldehyde-modified IFN-β-1a were digested with 20% (w/w) of endoproteinase Lys-C from *Achromobacter* (Wako Bioproducts) in PBS containing 5 mM DTT, 1 mM EDTA, at pH 7.6, at room temperature for 30 h (final volume=100 μL). 4 μL of 1 M DTT and 100 μL of 8 M urea were then added and the samples incubated for 1 h at room temperature. The peptides were separated by reverse-phase HPLC on a Vydac $C_{18}$ column (214TP51) using a 70 mM gradient from 0-63% acetonitrile, in 0.1% TFA, followed by a 10 min gradient from 63-80% acetonitrile, in 0.1% TFA. The column eluent was monitored for absorbance at 214 nm.

All of the predicted peptides from the endoproteinase Lys-C digest of IFN-β-1a have been identified previously by N-terminal sequencing and mass spectrometry (Pepinsky et al., (2001) J Pharmacology and Experimental Therapeutics 297:1059), and, of these, only the peptide that contains the N-terminus of IFN-β-1a was altered by modification with 20 kDa mPEG-O-m-methylphenyl-O-2-methylpropionaldehyde; as evident by its disappearance from the map. The mapping data therefore indicate that the PEG moiety is specifically attached to this peptide. The data further indicate that the PEG modification is targeted at the N-terminus of the protein since only the N-terminal modification would result in the specific loss of this peptide.

C) Preparation and Characterization of 20 kDa mPEG-O-p-phenylacetaldehyde-modified IFN-β-1a Human IFN-β-1a was PEGylated at the N-terminus with 20 kDa mPEG-O-p-phenylacetaldehyde. The product of the reductive alkylation chemistry that was used to incorporate the PEG onto the IFN-β-1a backbone results in the formation of an amine linkage which is extremely stable against degradation. The PEGylated IFN-β-1a was subjected to extensive characterization, including analysis by SDS-PAGE, SEC, peptide mapping, and assessment of activity in an in vitro antiviral assay. The purity of the product as measured by SDS-PAGE and SEC was greater than 95%. In the PEGylated IFN-β-1a sample there was no evidence of aggregates. Residual levels of unmodified IFN-β-1a in the product were below the limit of quantitation, but appear to represent about 1% of the product. In a stability test, no aggregation or degradation of 20 kDa mPEG-O-p-phenylacetaldehyde-modified IFN-β-1a was evident in Tris-buffer pH 7.4, following an incubation at 37° C. for up to 7 days. The specific activity of the PEGylated IFN-β-1a in the antiviral activity assay was reduced approximately 2-fold compared to the unmodified IFN-β-1a ($EC_{50=31}$ pg/mL for 20 kDa mPEG-O-p-phenylacetaldehyde-modified IFN-β-1a versus $EC_{50=14}$ pg/mL for unmodified IFN-β-1a) The PEGylated IFN-β-1a bulk was formulated at 30 μg/mL in PBS pH 7.3 containing 14 mg/mL HSA, similar to the formulation used for AVONEX® which has been subjected to extensive characterization. The material was supplied as a frozen liquid which was stored at −70° C.

The properties of 20 kDa mPEG-O-p-phenylacetaldehyde-modified IFN-β-1a are summarized in Table 3:

TABLE 3

Properties of 20 kDa mPEG-O-p-phenylacetaldehyde-modified IFN-β-1a

| | |
|---|---|
| Pegylation efficiency | >80% |
| IFN-β-1a/PEG ratio | 1:1 |
| Purity | >95% |
| Site of attachment | N-terminus |
| Antiviral activity $EC_{50}$ | 31 pg/mL |

1. Preparation of 20 kDa mPEG-O-p-phenylacetaldehyde-modified 20 mL of nonformulated AVONEX® (IFN-β-1a bulk intermediate, a clinical batch of bulk drug that passed all tests for use in humans, at 250 μg/mL in 100 mM sodium phosphate pH 7.2, 200 mM NaCl) was diluted with 24 mL of 165 mM MES pH 5.0, 100 μl of 5 N HCl, and 24 mL water. The sample was loaded onto a 600 μL SP-Sepharose FF column (Pharmacia). The column was washed with 2×900 μL of 5 mM sodium phosphate pH 5.5, 75 mM NaCl, and the protein was eluted with 5 mM sodium phosphate pH 5.5, 600 mM NaCl. Elution fractions were analyzed for their absorbance at 280 nm and the concentration of IFN-β-1a in the samples was estimated using an extinction coefficient of 1.51 for a 1 mg/mL solution. The peak fractions were pooled to give an IFN-β-1a concentration of 2.3 mg/mL. To 1.2 mL of the IFN-β-1a from the SP-Sepharose eluate pool, 0.5 M sodium phosphate pH 6.0 was added to 50 mM, sodium cyanoborohydride (Aldrich) was added to 5 mM, and 20 kDa mPEG-O-p-phenylacetaldehyde, was added to 10 mg/mL. The sample was incubated at room temperature for 18 h in the dark. The PEGylated IFN-β-1a was purified from the reaction mixture on a 0.75 mL SP-Sepharose FF column as follows: 1.5 mL of reaction mixture was diluted with 7.5 mL of 20 mM MES pH 5.0, 7.5 mL water, and 5 μL 5 N HCl, and loaded onto the SP-Sepharose column. The column was washed with sodium phosphate pH 5.5, 75 mM NaCl and then the PEGylated IFN-β-1a was eluted from the column with 20 mM MES pH 6.0, 600 mM NaCl. The PEGylated IFN-β-1a was further purified on a Superose 6 HR 10/30 FPLC sizing column with 5 mM sodium phosphate pH 5.5, 150 mM NaCl as the mobile phase. The sizing column (25 mL) was run at 20 mL/h and 0.5 mL fractions were collected. The elution fractions were analyzed for protein content by absorbance at 280 nm, pooled, and the protein concentration of the pool determined. The PEGylated IFN-β-1a concentration is reported in IFN equivalents after adjusting for the contribution of the PEG (20 kDa mPEG-O-p-phenylacetaldehyde has an extinction coefficient at 280 nm of 0.5 for a 1 mg/mL solution) to the absorbance at 280 nm using an extinction coefficient of 2 for a 1 mg/mL solution of the PEGylated IFN-β-1a. Samples of the pool were removed for analysis, and the remainder was diluted to 30 μg/mL with HSA-containing formulation buffer, aliquoted at 0.25 mL/vial, and stored at −70° C.

2. UV spectrum of purified 20 kDa mPEG-O-p-phenylacetaldehyde-modified IFN-β-1a. The UV spectrum (240-340 nm) of 20 kDa mPEG-O-p-phenylacetaldehyde-modified IFN-β-1a was obtained using the pre-HSA-formulated bulk sample. The PEGylated sample exhibited an absorbance maximum at 278-279 nm and an absorbance minimum at 249-250 nm, consistent with that observed for the unmodified IFN-β-1a bulk intermediate. The protein concentration of the PEGylated product was estimated from the spectrum using an extinction coefficient of $\epsilon_{280}^{0.1}=2.0$. The protein concentration of the PEGylated bulk was 0.10 mg/mL. No turbidity was present in the sample as evident by the lack of absorbance at 320 nm.

Figure 4:
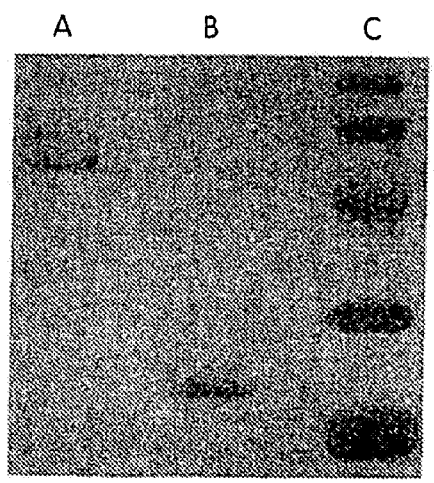
FIG. 4 is a reducing SDS-PAGE gel showing the purity of unmodified IFN-β-1a and 20 kDa mPEG-O-p-phenylacetaldehyde-modified IFN-β-1a: Lane A: 2.5 μg of 20 kDa mPEG-O-p-phenylacetaldehyde-modified IFN-β-1a; Lane B: 2.5 μg of unmodified IFN-β-1a; Lane C: molecular weight markers (from top to bottom; 100 kDa, 68 kDa, 45 kDa, 27 kDa, and 18 kDa, respectively).

3. Characterization of 20 kDa mPEG-O-p-phenylacetaldehyde-modified IFN-β-1a by SDS-PAGE. 2.5 μg of unmodified and 20 kDa mPEG-O-p-phenylacetaldehyde-modified IFN-β-1a were subjected to SDS-PAGE under reducing conditions on a 10-20% gradient gel. The gel was stained with Coomassie brilliant blue R-250, and is shown in FIG. 4 (Lane A: 20 kDa mPEG-O-p-phenylacetaldehyde-modified IFN-β-1a; Lane B: unmodified IFN-β-1a; Lane C: molecular weight markers (from top to bottom; 100 kDa, 68 kDa, 45 kDa, 27 kDa, and 18 kDa, respectively)). SDS-PAGE analysis of 20 kDa mPEG-O-p-phenylacetaldehyde-modified IFN-β-1a revealed a single major band with an apparent mass of 55 kDa consistent with modification by a single PEG. No higher mass forms resulting from the presence of additional PEG groups were detected. In the purified PEGylated product unmodified IFN-β-1a was detected; however, the amount is below the limit of quantitation. It is estimated that the level of unmodified IFN-β-1a in the preparation accounts for only about 1% of the total protein.

Figure 5:
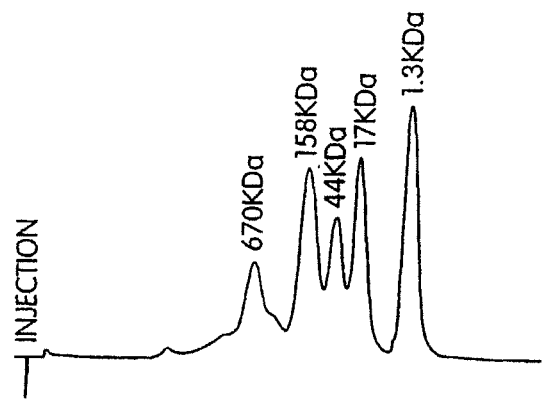
Figure 5:
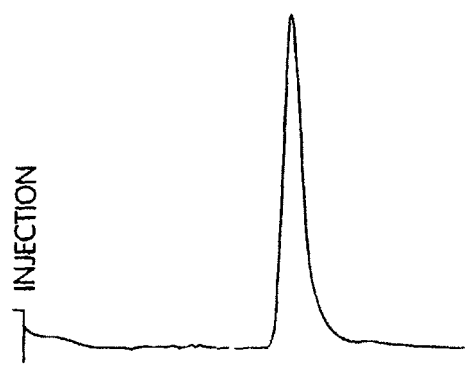

4. Characterization of 20 kDa mPEG-O-p-phenylacetaldehyde-modified IFN-β-1a by size exclusion chromatography. 20 kDa mPEG-O-p-phenylacetaldehyde-modified IFN-β-1a was subjected to SEC on an analytical Superose 6 HR10/30 FPLC sizing column using PBS pH 7.2 as the mobile phase. The column was run at 20 mL/h and the eluent was monitored for absorbance at 280 nm, as shown in FIG. 5: Panel A: molecular weight standards (670 kDa, thyroglobulin; 158 kDa, gamma globulin; 44 kDa, ovalbumin; 17 kDa, myoglobin; 1.3 kDa, vitamin B12); Panel B: 20 kDa mPEG-O-p-phenylacetaldehyde-modified IFN-β-1a. The PEGylated IFN-β-1a eluted as a single sharp peak with an apparent molecular mass of approximately 200 kDa consistent with the large hydrodynamic volume of the PEG. No evidence of aggregates was observed. Unmodified IFN-β-1a in the preparation was detected but was below the limit of quantitation. Based on the size of the peak, the unmodified IFN-β-1a accounts for 1% or less of the product, consistent with that observed using SDS-PAGE.

5. Analysis of 20 kDa mPEG-O-p-phenylacetaldehyde-modified IFN-β-1a by peptide mapping. The specificity of the PEGylation reaction was evaluated by peptide mapping. Unmodified and 20 kDa mPEG-O-p-phenylacetaldehyde-modified IFN-β-1a were digested with endoproteinase Lys-C from *Achromobacter* (Wako Bioproducts) and the resulting cleavage products were fractionated by reverse-phase HPLC on a Vydac $C_4$ column using a 30 min gradient from 0 to 70% acetonitrile, in 0.1% TFA. The column eluent was monitored for absorbance at 214 nm.

All of the predicted peptides from the endoproteinase Lys-C digest of IFN-β-1a have been identified previously by N-terminal sequencing and mass spectrometry (Pepinsky et al., (2001) J Pharmacology and Experimental Therapeutics 297:1059), and, of these, only the peptide that contains the N-terminus of IFN-β-1a was altered by modification with 20 kDa mPEG-O-p-phenylacetaldehyde; as evident by its disappearance from the map. The mapping data therefore indicate that the PEG moiety is specifically attached to this peptide. The data further indicate that the PEG modification is targeted at the N-terminus of the protein since only the N-terminal modification would result in the specific loss of this peptide.

Figure 6:
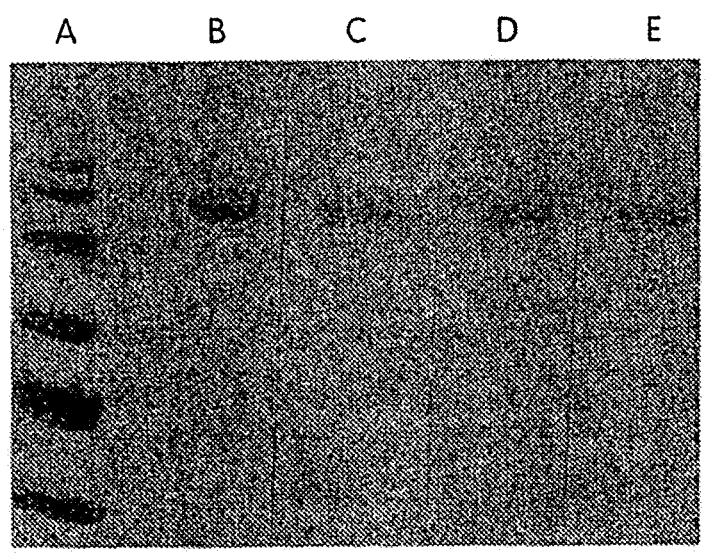
FIG. 6 is a reducing SDS-PAGE gel depicting the stability of 20 kDa mPEG-O-p-phenylacetaldehyde-modified IFN-β-1a: Lane A: molecular weight markers (from top to bottom; 100 kDa, 68 kDa, 45 kDa, 27 kDa, 18 kDa, and 15 kDa, respectively); Lanes B, C, D, and E: 2 μg of 20 kDa mPEG-O-p-phenylacetaldehyde-modified IFN-β-1a removed for assay at day 0, 2, 5, and 7, respectively.

6. Stability of 20 kDa mPEG-O-p-phenylacetaldehyde-modified IFN-β-1a. To test the stability of 20 kDa mPEG-O-p-phenylacetaldehyde-modified IFN-β-1a, samples were diluted to 0.1 μg/mL with 100 mM Tris-HCl buffer, pH 7.4, and were then incubated at 37° C. for up to 7 days. 20 μL of sample (2 μg) was removed at days 0, 2, 5, and 7, and analyzed by SDS-PAGE under reducing conditions, as shown in FIG. 6: Lane A: molecular weight markers (from top to bottom; 100 kDa, 68 kDa, 45 kDa, 27 kDa, 18 kDa, and 15 kDa, respectively); Lanes B, C, D, and E: mPEG-O-p-phenylacetaldehyde-modified IFN-β-1a removed at day 0, 2, 5, and 7, respectively. No evidence of aggregation or degradation of PEGylated was observed even after 7 days at 37° C.

Example 3

Specific Activity of PEGylated Human IFN-β-1a in an In vitro Antiviral Assay

Figure 7A:
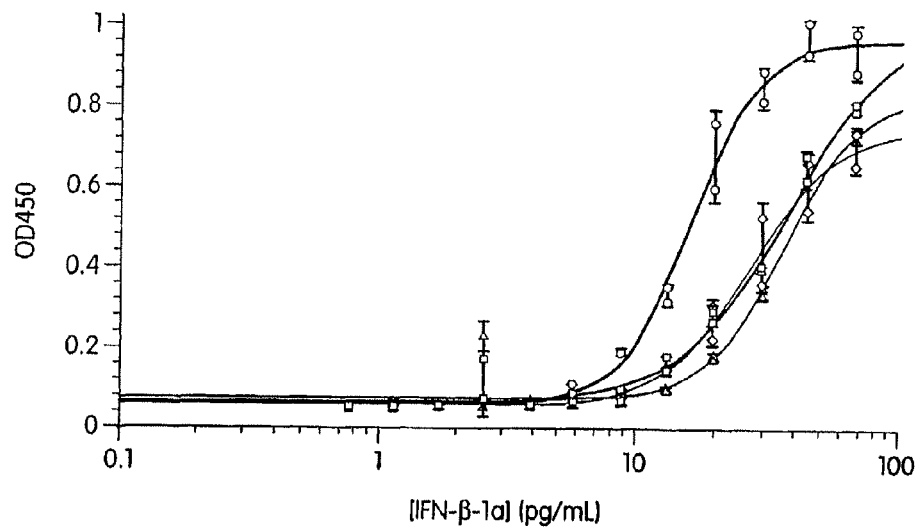
FIGS. 7A-B show the antiviral activity of various PEGylated human IFN-β-1a samples as a function of protein concentration.
Figure 7B:
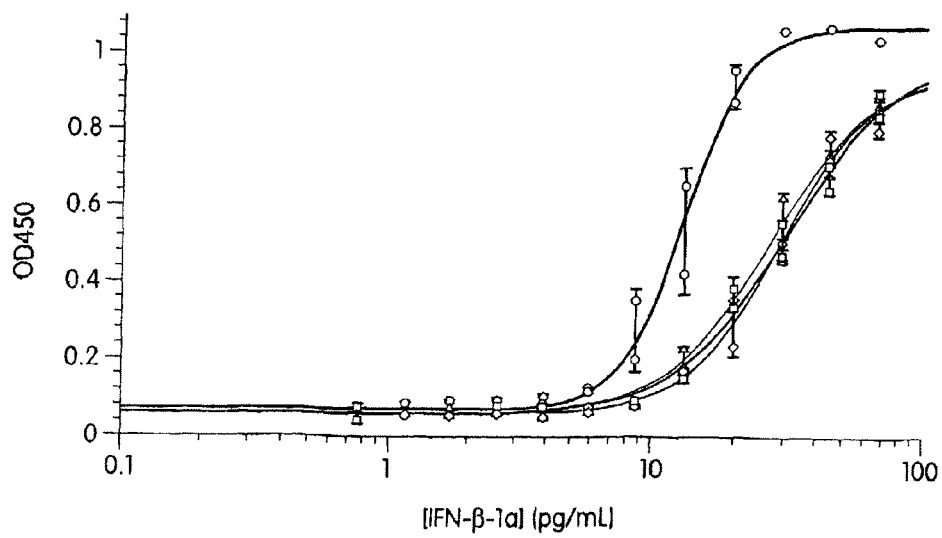

The specific antiviral activity of PEGylated IFN-β-1a samples was tested on human lung carcinoma cells (A549 cells) that had been exposed to encephalomyocarditis (EMC) virus, and using the metabolic dye 2,3-bis[2-Methoxy-4-nitro-5-sulfo-phenyl]-2H-tetrazolium-5-carboxyanilide (MTT; M-5655, Sigma, Si Louis, Mo.) as a measure of metabolically-active cells remaining after exposure to the virus. Briefly, A549 cells were pretreated for 24 h with either unmodified or PEGylated IFN-β-1a (starting at 66.7 pg/mL and diluting serially 1.5-fold to 0.8 pg/mL) prior to challenge with virus. The cells were then challenged for 2 days with EMC virus at a dilution that resulted in complete cell killing in the absence of IFN. Plates were then developed with MTT. A stock solution of MTT was prepared at 5 mg/mL in PBS and sterile-filtered, and 50 μL of this solution was diluted into cell cultures (100 μL per well). Following incubation at room temperature for 30-60 min, the MTT/media solution was discarded, cells were washed with 100 μL PBS, and finally the metabolized dye was solubilized with 100 μL 1.2 N HCl in isopropanol. Viable cells (as determined by the presence of the dye) were quantified by absorbance at 450 nm. Data were analyzed by plotting absorbance against the concentration of IFN-β-1a, and the activity of IFN-β-1a was defined as the concentration at which 50% of the cells were killed i.e., the 50% cytopathic effect ($EC_{50}$) or 50% maximum $OD_{450}$. The assay was performed eight times for unmodified IFN-β-1a and three to four times with the various PEGylated IFN-β-1a samples. For each assay, duplicate data points for each protein concentration were obtained. Representative plots of cell viability versus the concentration of unmodified or PEGylated IFN-β-1a are shown in FIGS. 7A and 7B. In FIG. 7A, the symbols are as follows: unmodified IFN-β-1a (○), 20 kDa mPEG-O-2-methylpropionaldehyde-modified IFN-β-1a (□), 20 kDa mPEG-O-p-methylphenyl-O-2-methylpropionaldehyde-modified IFN-β-1a (Δ), and 20 kDa mPEG-O-m-methylphenyl-O-2-methylpropionaldehyde-modified (◇). In FIG. 7B, the symbols are as follows: unmodified IFN-β-1a (○), 20 kDa mPFG-O-p-phenylacetaldehyde-modified (□), 20 kDa mPEG-O-p-phenylpropionaldehyde-modified IFN-β-1a (Δ), and 20 kDa mPEG-O-m-phenylacetaldehyde-modified IFN-β-1a (◇).

The $EC_{50}$ values (the concentration at half-maximal viral protection) for IFN-β-1a modified with 20 kDa mPEG-O-2-methylpropionaldehyde, 20 kDa mPEG-O-p-methylphenyl-O-2-methylpropionaldehyde, 20 kDa mPEG-O-m-methylphenyl-O-2-methylpropionaldehyde, 20 kDa mPEG-O-p-phenylacetaldehyde, 20 kDa mPEG-O-p-phenylpropionaldehyde, and 20 kDa mPEG-O-m-phenylacetaldehyde are shown in Table 4. All PEGylated IFN-β-1a were modified and purified to homogeneity essentially as described for 20 kDa mPEG-O-2-methylpropionaldehyde-modified IFN-β-1a, 20 kDa mPEG-O-m-methylphenyl-O-2-methylpropionaldehyde-modified IFN-β-1a, and 20 kDa mPEG-O-p-phenylacetaldehyde-modified IFN-β-1a as described above.

TABLE 4

Specific antiviral activity of unmodified and PEGylated IFNs-β-1a

| Protein | Mean EC$_{50}$ (pg/mL) |
|---|---|
| Unmodified IFN-β-1a | 14 (range 12-16) |
| 20 kDa mPEG-O-2-methylpropionaldehyde-modified IFN-β-1a | 32 (range 26-37) |
| 20 kDa mPEG-O-p-methylphenyl-O-2-methylpropionaldehyde-modified IFN-β-1a | 41 (range 36-47) |
| 20 kDa mPEG-O-m-methylphenyl-O-2-methylpropionaldehyde-modified IFN-β-1a | 31 (range 27-35) |
| 20 kDa mPEG-O-p-phenylacetaldehyde-modified IFN-β-1a | 31 (range 25-39) |
| 20 kDa mPEG-O-p-phenylpropionaldehyde-modified IFN-β-1a | 31 (range 27-34) |
| 20 kDa mPEG-O-m-phenylacetaldehyde-modified IFN-β-1a | 27 (range 25-29) |

Example 4

Pharmacokinetics of Intravenously-administered Unmodified and PEGylated IFNs-β-1a in Rats Cannulated female Lewis rats were injected intravenously with either 80 μg/kg of unmodified IFN-β-1a or 24 μg/kg of the following PEGylated IFNs-β-1a; 20 kDa mPEG-O-2-methylpropionaldehyde-modified IFN-β-1a, 20 kDa mPEG-O-p-methylphenyl-O-2-methylpropionaldehyde-modified IFN-β-1a, 20 kDa mPEG-O-p-phenylacetaldehyde-modified IFN-β-1a, 20 kDa mPEG-O-p-phenylpropionaldehyde-modified IFN-β-1a, 20 kDa mPEG-β-m-phenylacetaldehyde-modified IFN-β-1a, and 20 kDa mPEG-O-m-methylphenyl-O-2-methylpropionaldehyde-modified IFN-β-1a. Both the unmodified and PEGylated proteins were formulated in the presence of 14-15 mg/mL HSA as a carrier. For the unmodified protein, blood (0.2 mL) was obtained via the cannula at different time points; immediately prior to administration, and at 0.083, 0.25, 0.5, 1.25, 3, and 5 hours post-administration. For the PEGylated proteins, blood (0.2 mL) was obtained via the cannula immediately prior to administration, and at 0.083, 0.25, 0.5, 1.25, 3, 24, 48, and 72 h post-administration. Whole blood was collected into serum separator tubes (Beckton Dickinson No. 365956) and incubated at room temperature for 60 min to allow for clotting. The clotted blood was centrifuged for 10 min at 4° C., and the serum removed and stored at −70° C. until the time of assay.

The serum samples were then thawed and tested in antiviral assays. The serum samples were diluted 1:50 into serum-containing medium (Dulbecco's Modified Eagles Medium containing 10% (v/v) fetal bovine serum, 100 U each of penicillin and streptomycin, and 2 mM L-glutamine) and tested in antiviral assays. Samples were titrated into designated wells of a 96 well tissue culture plate containing human lung carcinoma cells (A549, #CCL-185, ATCC, Rockville, Md.). Dilutions of a standard (66.7, 44.4, 29.6, 19.8, 13.2, 8.8, 5.9, 3.9, 2.6, 1.7, 1.2, and 0.8 pg/mL of the same form of IFN-β-1a administered to the rat) and of three serum samples were assayed on each plate. The A549 cells were pretreated with diluted serum samples for 24 h prior to challenge with encephalomyelocarditis (EMC) virus. Following a 2 day incubation with virus, viable cells were stained with a solution of MTT (at 5 mg/mL in phosphate buffer) for 1 h, washed with phosphate buffer, and solubilized with 1.2 N HCl in isopropanol. The wells were then read at 450 nm. Standard curves of the unmodified or PEGylated IFN-β-1a were generated for each plate and used to determine the amount of unmodified or PEGylated IFN-β-1a in each test sample. Pharmacokinetic parameters were then calculated using non-compartmental analysis with WinNonLin version 3.0 or 3.3 software.

Figure 8A:
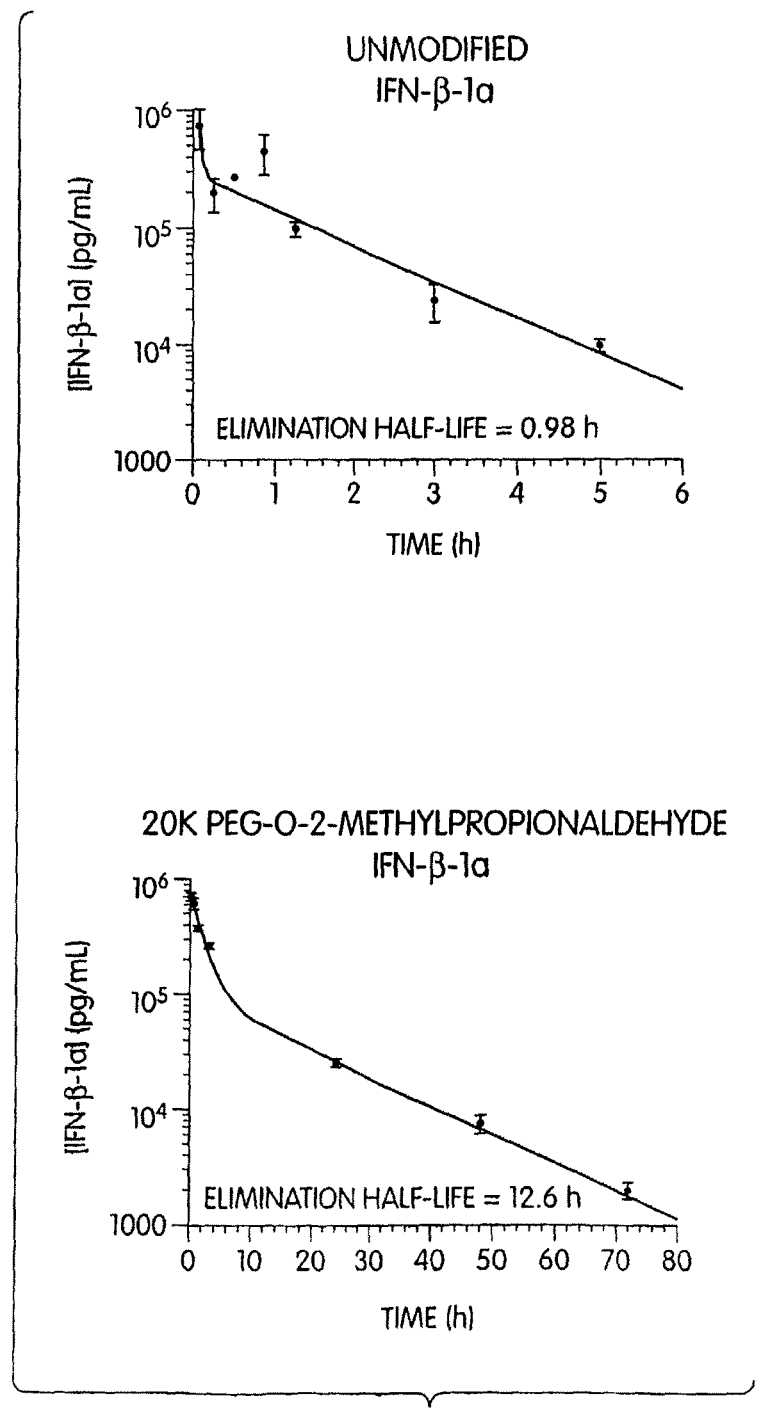
FIGS. 8A-B are graphs depicting the pharmacokinetics of unmodified and various PEGylated human IFN-β-1a samples.
Figure 8B:
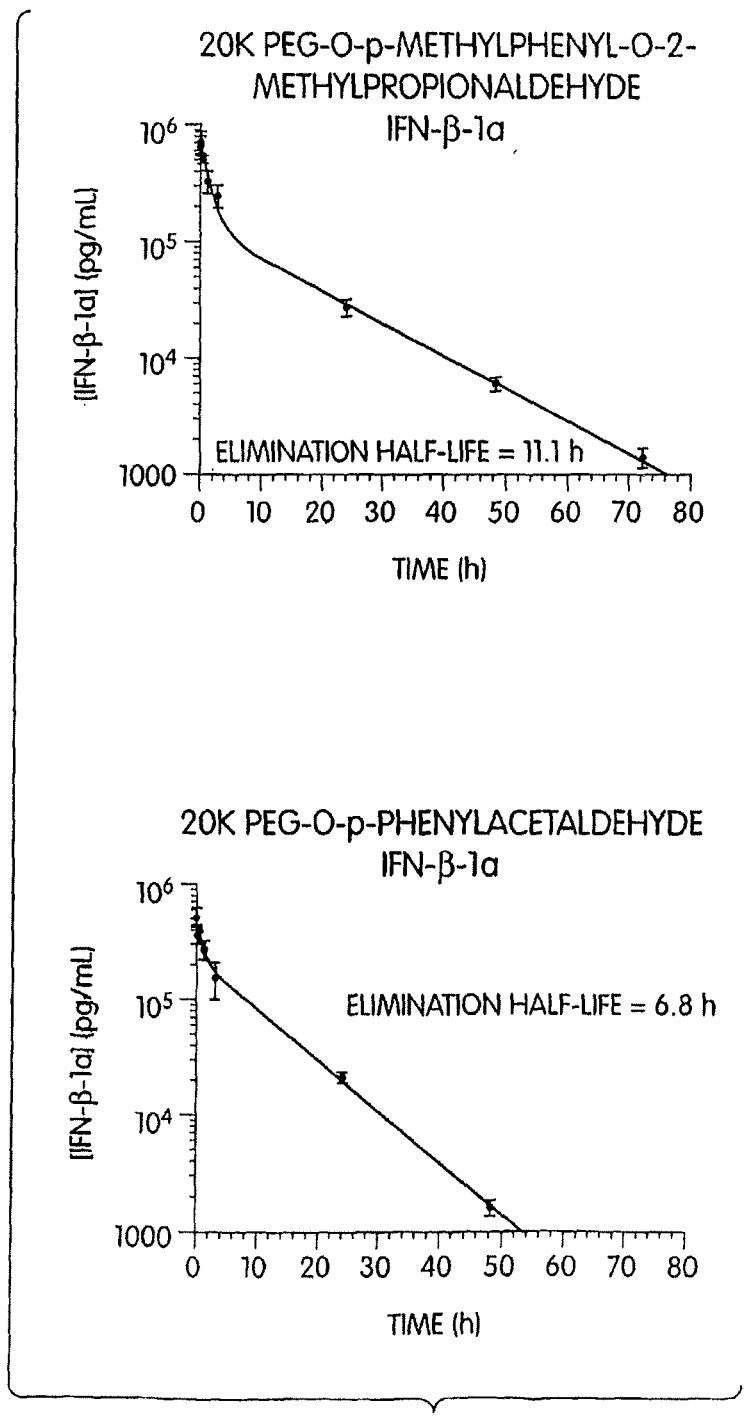

FIG. 8A shows the concentration versus time plots for unmodified IFN-β-1a (upper panel) and IFN-β-1a modified with 20 kDa mPEG-O-2-methylpropionaldehyde (lower panel), and FIG. 8B shows the concentration versus time plots for IFN-β-1a modified with 20 kDa mPEG-O-p-methylphenyl-O-2-methylpropionaldehyde (upper panel) and 20 kDa mPEG-O-p-phenylacetaldehyde (lower panel). Data points are averages from measurements from 3 rats.

Table 5 shows the pharmacokinetic parameters $C_{max}$ (maximal observed concentration), $t_{1/2}$ (elimination half-life) AUC (area under the curve), Vss (distribution volume at steady state), clearance rate, and MRT (mean residence time) for unmodified IFN-β-1a and these forms of PEGylated IFN-β-1a. The data shown in FIGS. 8A and 8B and in Table 5 were obtained in the same study.

Figure 9A:
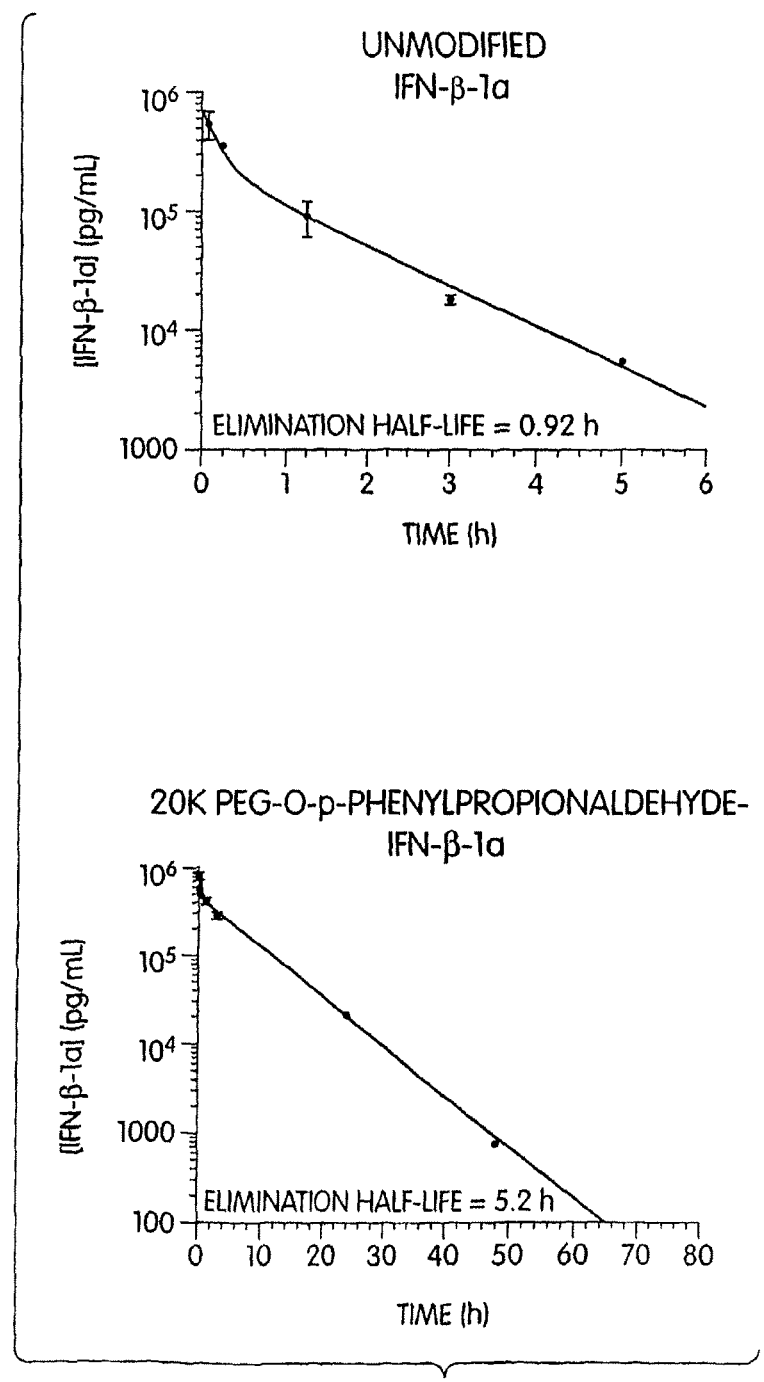
FIGS. 9A-B are graphs depicting the pharmacokinetics of unmodified and various PEGylated human IFN-β-1a samples.
Figure 9B:
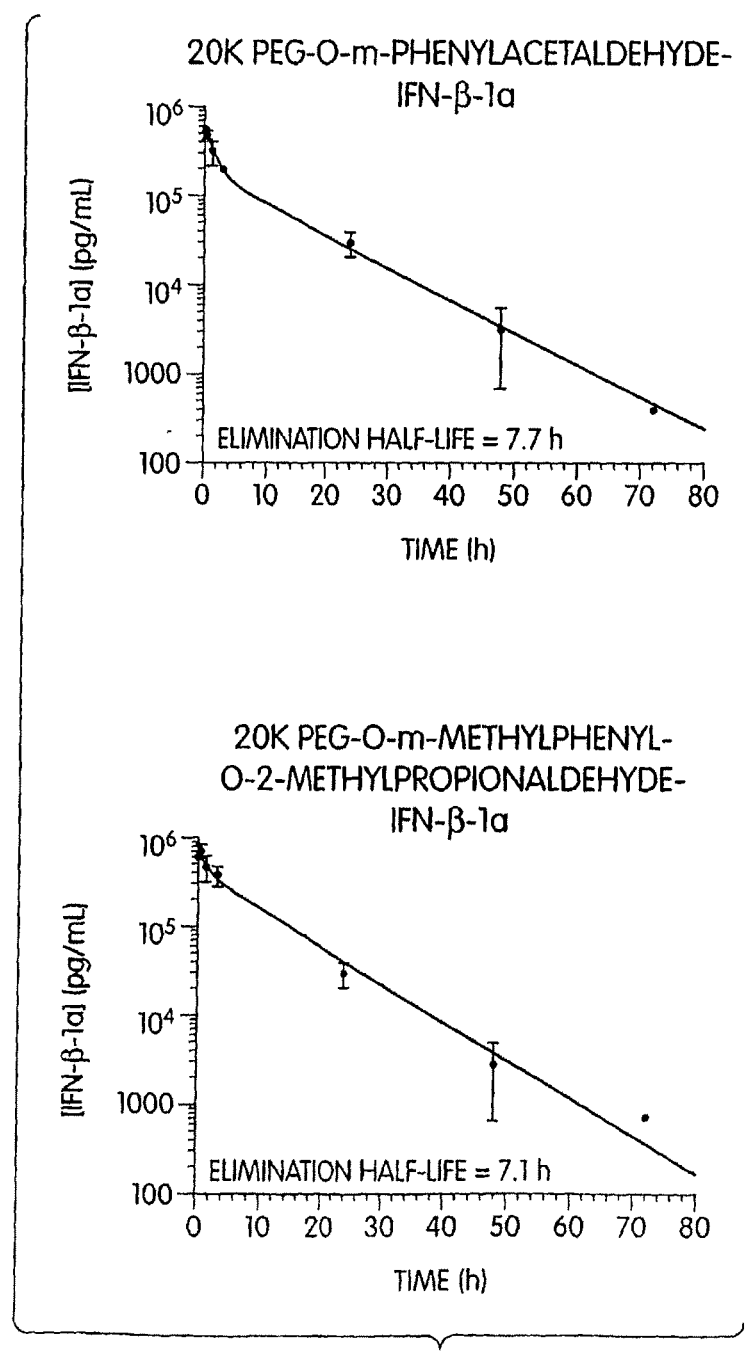

FIG. 9A shows the concentration versus time plots for unmodified IFN-β-1a (upper panel) and IFN-β-1a modified with 20 kDa mPEG-O-p-phenylpropionaldehyde (lower panel). Data points are averages from measurements from 2 rats. FIG. 9B shows the concentration versus time plots for IFN-β-1a modified with 20 kDa mPEG-O-m-phenylacetaldehyde (upper panel) and 20 kDa mPEG-O-m-methylphenyl-O-2-methylpropionaldehyde (lower panel). Data points are averages from measurements from 3 rats.

Table 6 shows the pharmacokinetic parameters for unmodified IFN-β-1a and these forms of PEGylated IFN-β-1a. The data shown in FIGS. 9A and 9B and in Table 6 were obtained in the same study; independent from the data shown in FIGS. 8A and 8B, and in Table 5.

As is clear from the data shown in FIGS. 8A, 8B, 9A, and 9B, and in Tables 5 and 6, PEGylation of IFN-β-1a with the PEG molecules of the invention improves the pharmacokinetic properties of IFN-β-1a. In all cases, the PEGylated proteins were cleared less rapidly than unmodified IFN-β-1a, resulting in clearance rates of 3.9-8.3 mL/h/kg as compared to 160-170 mL/h/kg for the unmodified protein. As a consequence of the reduced clearance rates, the mean residence time (MRT) increased from approximately 1 h for the unmodified protein to 4.8-7.6 h for the PEGylated proteins. Similarly, the elimination half-life ($t_{1/2}$) increased from approximately 1 h for the unmodified protein to 5.2-13 h for the PEGylated proteins. The area under the curve (AUC) values were also significantly increased upon PEGylation of IFN-β-1a. For unmodified IFN-β-1a, the AUC was approximately 0.5 μg·h/mL while for the PEGylated proteins the AUC values ranged from approximately 3 to 6 μg·h/mL, despite the fact that the PEGylated proteins were dosed at a level 3.3-fold lower than the unmodified protein. For the maximal observed concentration ($C_{max}$), the values were generally higher for unmodified IFN-β-1a than for the PEGylated proteins, reflecting the lower dose of the modified proteins administered. For the volume of distribution at steady state (Vss), the values for all the PEGylated proteins were lower than for unmodified IFN-β-1a, indicating a restriction in their ability to exit the central blood compartment.

TABLE 5

Pharmacokinetic parameters for unmodified IFN-β-1a, 20 kDa mPEG-O-2-methylpropionaldehyde-modified IFN-β-1a, 20 kDa mPEG-O-p-methylphenyl-O-2-methylpropionaldehyde-modified IFN-β-1a, and 20 kDa mPEG-O-p-phenylacetaldehyde-modified IFN-β-1a following intravenous administration in rats[a]

| Parameter | Units | Unmodified IFN-β-1a | 20 kDa mPEG-O-2-methylpropionaldehyde-modified IFN-β-1a | 20 kDa mPEG-O-p-methylphenyl-O-2-methylpropionaldehyde-modified IFN-β-1a | 20 kDa mPEG-O-p-phenylacetaldehyde-modified IFN-β-1a |
|---|---|---|---|---|---|
| $C_{max}$ | pg/mL | 1,400,000 | 720,000 | 710,000 | 590,000 |
| $t_{1/2}$ | h | 0.98 | 13 | 11 | 6.8 |
| AUC | pg · h/mL | 510,000 | 4,800,000 | 4,500,000 | 2,900,000 |
| Vss | mL/kg | 160 | 39 | 40 | 53 |
| Clearance | mL/h/kg | 160 | 5.0 | 5.3 | 8.3 |
| MRT | h | 0.98 | 7.6 | 7.4 | 6.4 |

[a]The pharmacokinetic data for the unmodified and PEGylated IFNs-β-1a shown were obtained in the same study

TABLE 6

Pharmacokinetic parameters for unmodified IFN-β-1a, 20 kDa mPEG-O-p-phenylpropionaldehyde-modified IFN-β-1a, 20 kDa mPEG-O-m-phenylacetaldehyde-modified IFN-β-1a, and 20 kDa mPEG-O-m-methylphenyl-O-2-methylpropionaldehyde-modified IFN-β-1a following intravenous administration in rats[a]

| Parameter | Units | Unmodified IFN-β-1a | 20 kDa mPEG-O-p-phenylpropionaldehyde-modified IFN-β-1a | 20 kDa mPEG-O-m-phenylacetaldehyde-modified IFN-β-1a | 20 kDa mPEG-O-m-methylphenyl-O-2-methylpropionaldehyde-modified IFN-β-1a |
|---|---|---|---|---|---|
| $C_{max}$ | pg/mL | 670,000 | 930,000 | 550,000 | 700,000 |
| $t_{1/2}$ | h | 0.92 | 5.2 | 7.7 | 7.1 |
| AUC | pg · h/mL | 470,000 | 4,700,000 | 3,800,000 | 6,200,000 |
| Vss | mL/kg | 140 | 25 | 46 | 21 |
| Clearance | mL/h/kg | 170 | 5.1 | 6.4 | 3.9 |
| MRT | h | 0.81 | 4.8 | 7.2 | 5.5 |

[a]The pharmacokinetic data for the unmodified and PEGylated IFNs-β-1a shown were obtained in the same study.

Example 5

Comparative Pharmacokinetics and Pharmacodynamics of Unmodified and PEGylated Human IFN-β-1a in Non-human Primates Single and repeat dose comparative studies are conducted with unmodified and PEGylated IFN-β-1a to determine their relative stability and activity in non-human primates. In these studies, the pharmacokinetics and pharmacodynamics of the PEGylated conjugates is compared to that of unmodified IFN-β-1a and reasonable inferences can be extended to humans.

Animals and Methods

Study 1 (repeat dose)

This is a parallel group, repeat dose study to evaluate the comparative pharmacokinetics and pharmacodynamics of unmodified and PEGylated IFN-1'-1a. Healthy primates (e.g., rhesus monkeys) are used for this study. Prior to dosing, all animals are evaluated for signs of ill health by a laboratory animal veterinarian on two occasions within 14 days prior to test article administration; one evaluation must be within 24 h prior to the first test article administration. Only healthy animals receive the test article. Evaluations include a general physical examination and pre-dose blood draws for baseline clinical pathology and baseline antibody level to IFN-β-1a. All animals are weighed and body temperatures are recorded within 24 h prior to test article administrations. Twelve subjects are enrolled and assigned to groups of three to receive $1 \times 10^6$ U/kg of unmodified or PEGylated IFN-β-1a, but otherwise identical IFN-β-1a. Administration is by either the subcutaneous (SC) or intravenous (IV) routes. Six male animals receive test article by the IV route (3 per treatment) and another 6 male animals receive test article by the SC route (3 per treatment). All animals must be naive to IFN-β treatment. Each animal is dosed on two occasions, the doses are separated by four weeks. The dose volume is 1.0 mL/kg. Blood is drawn for pharmacokinetic testing at 0, 0.083, 0.25, 0.5, 1, 1.5, 2, 4, 6, 8, 12, 24, 48, 72, and at 96 hours following each injection. Blood samples for measurement of the IFN-induced biological response marker, serum neopterin, are drawn at 0, 24, 48, 72, 96, 168, 336, and at 504 h following administration of study drug. Evaluations during the study period include clinical observations performed 30 min and 1 h post-dose for signs of toxicity. Daily cage-side observations are performed and general appearance, signs of toxicity, discomfort, and changes in behavior are recorded. Body weights and body temperatures are recorded at regular intervals through 21 days post-dose.

Study 2 (Single Dose)

This is a parallel group, single dose study to evaluate the comparative pharmacokinetics and pharmacodynamics of unmodified and PEGylated IFN-β-1a. Healthy primates (e.g., rhesus monkeys) are used for this study. Prior to dosing, all animals are evaluated for signs of ill health by a laboratory animal veterinarian on two occasions within 14 days prior to test article administration; one evaluation must be within 24 h prior to the first test article administration. Only healthy animals receive the test article. Evaluations include a general physical examination and pre-dose blood draws for baseline clinical pathology and baseline antibody level to IFN-β-1a. All animals are weighed and body temperatures are recorded within 24 h prior to test article administrations. Twenty subjects are enrolled and assigned to one of five groups of four animals (2 male and 2 female per group) to receive either $1 \times 10^6$ U/kg of unmodified or PEGylated IFN-β-1a intramuscularly (IM), or $2 \times 10^5$ U/kg, $1 \times 10^6$ U/kg, or $5 \times 10^6$ U/kg of PEGylated IFN-β-1a intravenously (IV). All animals must be naive to IFN-β treatment. The dose volume is generally 1.0 mL/kg. Blood is drawn for pharmacokinetic testing at 0, 0.5, 1, 2, 4, 6, 8, 12, 24, 36, 48, and at 96 hours, and at 7, 14, 21, and at 28 days following administration of study drug. Blood samples for measurement of the IFN-induced biological response marker, 2'-5'-oligoadenylate synthase (2'-5'-OAS), are drawn at 0, 12, 24, 48, 72, and at 96 hours, and at 7, 14, 21, and at 28 days following administration of study drug. Evaluations during the study period include clinical observations performed 30 min and 1 h post-dose for signs of toxicity. Daily cage-side observations are performed and general appearance, signs of toxicity, discomfort, and changes in behavior are recorded. Body weights and body temperatures are recorded at regular intervals through 28 days post-dose.

Assay Methods

Levels of IFN-β-1a in serum are quantitated using a cytopathic effect (CPE) bioassay.

The CPE assay measures levels of IFN-mediated antiviral activity. The level of antiviral activity in a sample reflects the number of molecules of active IFN contained in that sample at the time the blood is drawn. This approach has been the standard method to assess the pharmacokinetics of IFN-β. The CPE assay detects the ability of IFN-β to protect human lung carcinoma cells (A549, #CCL-185, ATCC, Rockville, Md.) from cytotoxicity due to encephalomyocarditis (EMC) virus. The cells are preincubated for 15-20 h with serum samples to allow the induction and synthesis of IFN-inducible proteins that are responsible for the antiviral response. EMC virus is then added and incubated for a further 30 h before assessment of cytotoxicity is made using a crystal violet stain. An internal IFN-β standard as well as a PEGylated IFN-β-1a internal standard is tested concurrently with samples on each assay plate. This standard is calibrated against a natural human fibroblast IFN reference standard (WHO Second International Standard for Interferon, Human Fibroblast, Gb-23-902-53). Each assay plate also includes cell growth control wells containing neither IFN-β of any kind nor EMC, and virus control wells that contain cells and EMC but no IFN-β. Control plates containing the standard and samples are also prepared to determine the effect, if any, of the samples on cell growth. These plates are stained without the addition of virus. Samples and standards are tested in duplicate on each of two replicate assay plates, yielding four data points per sample. The geometric mean concentration of the four replicates is reported. The limit of detection in this assay is 10 U/mL. Serum concentrations of neopterin are determined at the clinical pharmacology unit using commercially-available assays. Serum concentrations of 2'-5'-OAS are determined at a contract laboratory using a validated commercially-available assay.

Pharmacokinetic and Statistical Methods

Rstrip™ software (MicroMath, Inc., Salt Lake City, Utah) is used to fit data to pharmacokinetic models. Geometric mean concentrations are plotted by time for each group. Since assay results are expressed in dilutions, geometric means are considered more appropriate than arithmetic means. Serum IFN levels are adjusted for baseline values and non-detectable serum concentrations are set to 5 U/mL, which represents one-half the lower limit of detection. For IV infusion data, a two compartment IV infusion model is fit to the detectable serum concentrations for each subject, and the SC data are fit to a two compartment injection model.

The following pharmacokinetic parameters are calculated:
(i) observed peak concentration, $C_{max}$ (U/mL);
(ii) area under the curve from 0 to 48 h, AUC (U×h/mL) using the trapezoidal rule;
(iii) elimination half-life (h); and, from IV infusion data (if IV is employed):
(iv) distribution half-life (h);
(v) clearance (mL/h/kg)
(vi) apparent volume of distribution, Vd (mL/kg).

WinNonlin (Version 1.0, Scientific Consulting Inc., Apex, N.C.) software is used to calculate the elimination half-lives after IV and SC injection. For neopterin and 2'-5'-OAS, arithmetic means by time are presented for each group. $E_{max}$, the maximum change from baseline, is calculated. AUC, and $E_{max}$ are submitted to a one-way analysis of variance to compare dosing groups. $C_{max}$ and AUC are logarithmically-transformed prior to analysis; geometric means are reported.

Example 6

Anti-Angiogenic Effects of PEGylated Human IFN-β-1a; the Ability of PEGylated IFN-β-1a to Inhibit Endothelial Cell Proliferation In Vitro Human venous endothelial cells (Cell Systems, Cat. # 2V0-P75) and human dermal microvascular endothelial cells (Cell Systems, Cat. # 2M1-C25) are maintained in culture with CS-C Medium Kit (Cell Systems, Cat. # 4Z0-500). 24 h prior to the experiment, cells are trypsinized, and resuspended in assay medium, 90% M199 and 10% fetal bovine serum (FBS), and are adjusted to desired cell density. Cells are then plated onto gelatin-coated 24 or 96 well plates, either at 12,500 cells/well or 2,000 cells/well, respectively. After overnight incubation, the assay medium is replaced with fresh medium containing 20 ng/mL of human recombinant basic Fibroblast Growth Factor (bFGF) (Becton Dickinson, Cat. # 40060) and various concentrations of unmodified or PEGylated IFN-β-1a of the invention or positive control (endostatin can be used as a positive control, as could an antibody to bFGF) are added. The final volume is adjusted to 0.5 mL in the 24 well plate or 0.2 mL in the 96 well plate. After 72 h, cells are trypsinized for Coulter counting, frozen for CyQuant fluorescence reading, or labeled with [$^3$H]-thymidine. This in vitro assay tests the PEGylated human IFN-β-1a molecules of the invention for effects on endothelial cell proliferation which may be indicative of anti-angiogenic effects in vivo. See O'Reilly, et al., Cell 88: 277-285 (1997).

Example 7

In vivo Models to Test Anti-angiogenic and Neovascularization Effects of PEGylated Human IFN-β-1a and PEGylated Rodent IFNs-β

Unmodified IFN-β-1a and 20 kDa mPEG-O-2-methylpropionaldehyde-modified IFN-β-1a were tested for their ability to inhibit the formation of radially-oriented vessels entering the periphery of SK-MEL-1 human malignant melanoma tumors in athymic nude homozygous (nu/nu) mice. SK-MEL-1 cells were grown in culture to 80% confluency, and then $2 \times 10^6$ cells inoculated intradermally (0.1 mL volume on day 0) into the flank in the mid-axillary line in three week old athymic nude homozygous (nu/nu) NCR mice (Taconic, Germantown, N.Y.). 24 hours later (day 1), groups of three mice each received the following subcutaneous doses of vehicle control, unmodified IFN-β-1a, or 20 kDa mPEG-O-2-methylpropionaldehyde-modified IFN-β-1a:

Group A: 0.1 mL of 45.6 mg/mL human serum albumin (vehicle control) once on day 1 only Group B: 0.1 mL of 45.6 mg/mL human serum albumin containing 1 MU (5 μg) of unmodified IFN-β-1a daily on days 1-9 inclusive Group C: 0.1 mL of 45.6 mg/mL human serum albumin containing 1 MU units (10 μg) of 20 kDa mPEG-O-2-methylpropionaldehyde-modified IFN-β-1a once on day 1 only Group D: 0.1 mL of 45.6 mg/mL human serum albumin (vehicle control) daily on days 1-9 inclusive Mice were sacrificed on day 10 (Avertin, 0.5 mL intraperitoneally) and the tumor inoculation site assessed for neovascularization, measured by an observer blind as to treatment group. Vessels were counted under fixed magnification under a dissecting microscope. Every radially-oriented vessel entering the periphery of the tumor was scored as a single vessel. Each group consisted of three mice.

Figure 10:
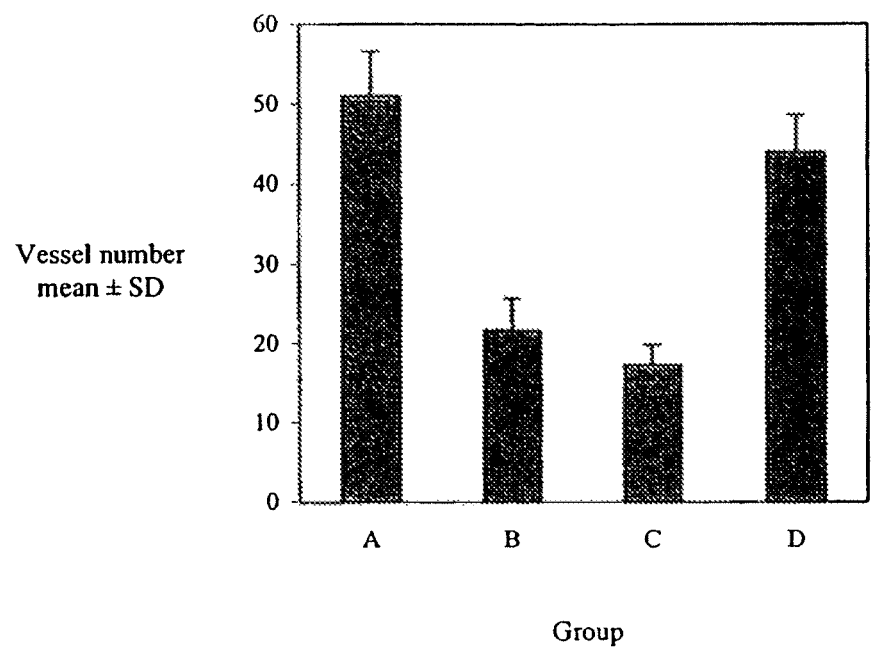
FIG. 10 is a bar graph comparing a single administration of 20 kDa mPEG-O-2-methylpropionaldehyde-modified IFN-β-1a, with daily administration of unmodified IFN-β-1a at reducing the number of radially-oriented neovessels in nu/nu mice carrying SK-MEL-1 human malignant melanoma cells: treatment with vehicle control once on day 1 only (bar A); treatment with 1 MU (5 µg) of unmodified IFN-β-1a daily on days 1-9 inclusive (bar B); treatment with 1 MU (10 µg) of 20 kDa mPEG-O-2-methylpropionaldehyde-modified IFN-13-1a once on day 1 only (bar C); and treatment with vehicle control daily on days 1-9 inclusive (bar D).

As shown in FIG. 10, a single administration of 1 MU of 20 kDa mPEG-O-2-methylpropionaldehyde-modified IFN-β-1a (group C) was as effective at reducing the number of neovessels as daily administration of 1 MU of unmodified IFN-β-1a (group B). However, the effect of the 20 kDa mPEG-O-2-methylpropionaldehyde-modified IFN-β-1a is more pronounced when considering that daily administration of the vehicle alone had some inhibitory effect (compare group A, vehicle given once, with group D, vehicle given daily).

A variety of other models have also been developed which can be used to test the anti-angiogenic and anti-neovascularization effects of the PEGylated molecules of the invention. Some of these models have been described in U.S. Pat. No. 5,733,876 (Mar. 31, 1998: "Method of inhibiting angiogenesis") and U.S. Pat. No. 5,135,919 (Aug. 4, 1992: "Method and a pharmaceutical composition for the inhibition of angiogenesis"). Other assays include the shell-less chorioallantoic membrane (CAM) assay of Taylor and Folkman; Nature 297: 307 (1982) and Crum et al., Science 230:1375 (1985); the mouse dorsal air sac method anti-angiogenesis model of Folkman et al.; J. Exp. Med. 133: 275 (1971), and the rat corneal micropocket assay of Gimbrone, Jr. et al., J. Natl. Cancer Inst. 52:413 (1974) in which corneal vascularization is induced in adult male rats of the Sprague-Dawley strain (Charles River, Japan) by implanting 500 ng of bFGF (bovine, R & D Systems, Inc.), impregnated in ethylene-vinyl acetate copolymer pellets, in each cornea. In addition, a model exists in which angiogenesis is induced in NIH-Swiss or athymic nude (nu/nu) mice after implantation of MCF-7 breast carcinoma or NIH-OVCAR-3 ovarian carcinoma cells as described by Lindner and Borden; Int. J. Cancer 71:456 (1997). Additional tumor cell lines including (but not limited to) SK-MEL-1 human malignant melanoma cells may also be used to induce angiogenesis as described above. Various doses, with various dosing frequencies, and for various duration can be tested for both the unmodified and PEGylated IFN-β-1a proteins of the invention.

Other methods for testing PEGylated murine and rat IFN-β for anti-angiogenic effects in an animal model include (but are not limited to) protocols for screening new potential anti-cancer agents as described in the original Cancer Chemotherapy Reports, Part 3, Vol. 3, No. 2, September 1972 and the supplement In Vivo Cancer Models, 1976-1982, NIH Publication No. 84-2635, February 1984. Because of the species specificity of Type I interferons, to assess the anti-angiogenic activity of PEGylated IFN-β in rodent models, PEGylated rodent IFN-β preparations (e.g., murine and rat) are generated. Such screening methods are exemplified by a protocol to test for the anti-angiogenic effects of PEGylated murine IFN-β on subcutaneously-implanted Lewis Lung Carcinoma:

Origin of Tumor Line

This tumor line arose spontaneously in 1951 as a carcinoma of the lung in a C57BL/6 mouse.

Summary of Test Procedure

A tumor fragment is implanted subcutaneously in the axillary region of a B6D2F1 mouse. The test agent (i.e., a PEGylated interferon of the invention) is administered at various doses, subcutaneously (SC) or intraperitoneally (IP) on multiple days following tumor implantation. The parameter measured is median survival time. Results are expressed as a percentage of control survival time.

Animals

Propagation: C57BL16 mice.

Testing: B6D2F1 mice.

Weight: Mice are within a 3 g weight range, with a minimum weight of 18 g for males and 17 g for females.

Sex: One sex is used for all test and control animals in one experiment.

Source: One source, if feasible, for all animals in one experiment.

Experiment Size

Ten animals per test group.

Tumor Transfer

Propagation:

Fragment: Prepare a 2-4 mm fragment of a SC donor tumor.

Time: Day 13-15.

Site: Implant the fragment SC in the axillary region with a puncture in the inguinal region.

Testing:

Fragment: Prepare a 2-4 mm fragment of SC donor tumor.

Time: Day 13-15.

Site: Implant the fragment SC in the axillary region with a puncture in the inguinal region.

Testing Schedule

Day 0: Implant tumor. Run bacterial cultures. Test positive control compound in every odd-numbered experiment. Prepare materials. Record deaths daily.

Day 1: Check cultures. Discard experiment if contaminated. Randomize animals. Treat as instructed (on day 1 and on following days).

Day 2: Recheck cultures. Discard experiment if contaminated.

Day 5: Weigh Day 2 and day of initial test agent toxicity evaluation.

Day 14: Control early-death day.

Day 48: Control no-take day.

Day 60: End and evaluate experiment. Examine lungs for tumor.

Quality Control

Schedule the positive control compound (NSC 26271; Cytoxan at a dose of 100 mg/kg/injection) in every odd-numbered experiment, the regimen for which is intraperitoneal on Day 1 only. The lower Test/Control limit for the positive control is 140%. The acceptable untreated control median survival time is 19-35.6 days.

Evaluation

The parameter measured is median survival time. Compute the mean animal body weights for Day 1 and Day 5, compute Test/Control ratio for all test groups. The mean animal body weights for staging day and final evaluation day are computed. The Test/Control ratio is computed for all test groups with >65% survivors on Day 5. A Test/Control ratio value <86% indicates toxicity. An excessive body weight change difference (test minus control) may also be used in evaluating toxicity.

Criteria for Activity

An initial Test/Control ratio greater than or equal to 140% is considered necessary to demonstrate moderate activity. A reproducible Test/Control ratio value of greater than or equal to 150% is considered significant activity.

Example 8

In vivo Models to Test the Antiproliferative and Anti-Tumor Effects of PEGylated Human IFN-β-1a and PEGylated Rodent IFNs-β

Various in vivo models are available to test the anti-proliferative and anti-tumor effects of unmodified and PEGylated human IFNs-β-1a of the invention. In a model described by Bailon et al., Bioconjugate Chemistry 12:195 (2001), athymic nude mice (Harlan) are implanted subcutaneously with $2\times10^6$ human renal A498, human renal ACHN, or human renal G402 cells under the rear flank and 3-6 weeks allowed for tumors to develop. Unmodified or PEGylated human IFN-β-1a is then administered at various doses, with various dosing frequencies, and for various duration, and tumor volume measured and compared between treatments. In another model described by Lindner and Borden, J. Interferon Cytokine Res 17: 681 (1997), athymic nude (nu/nu) oophorectomized female BALB/c mice are implanted with $2\times10^6$ MCF-7 (plus estradiol), MDA-MB-231, MDA-MB-468, or BT-20 human breast carcinoma cells, NIH-OVCAR-3 human ovarian carcinoma cells, HT-29 human colon carcinoma cells, or SK-MEL-1 or FEMX human malignant melinoma cells, into the dermis overlying the mammary glands nearest the axillae, and the size of the tumors assessed as a function of time. Unmodified or PEGylated human IFN-β-1a is then administered at various doses, with various dosing frequencies, and for various duration, and tumor volume measured and compared between treatments. Other models for testing the anti-proliferative and anti-tumor effects of PEGylated human IFN-β-1a include (but are not limited to) local and metastatic lung cancer models described by Qin et al., Molecular Therapy 4: 356 (2001), and nude mouse xenograft models of human colorectal cancer liver metastases described by Tada et al, J Clinical Investigation 108: 83 (2001).

Other methods for testing PEGylated murine and rat IFN-β for anti-proliferative and anti-tumor effects in animal models include (but are not limited to) a mouse model of malignant mesothelioma described by Odaka et al., Cancer Res 61: 6201 (2001), local and metastatic lung cancer models described by Qin et al., Molecular Therapy 4: 356 (2001), and syngeneic mouse models of colorectal cancer liver metastases described by Tada et al., J Clinical Investigation 108: 83 (2001).

Example 9

In vivo Models to Test Anti-Viral Effects of PEGylated Murine IFN-β and PEGylated Human IFN-β-1a An in vivo mouse model is available to test the effect of unmodified and PEGylated murine IFN-β on the levels of human Hepatitis B Virus (HBV) in HBV-transgenic SCID mice. Larkin et al., Nature Medicine 5:907 (1999). In this model, transgenic SCID mice carrying a head-to-tail dimer of the human HBV genome have detectable levels of HBV replicative forms and pre-genomic RNA in the liver, and HBV virus in the serum. Hepatocytes from the transgenic mice are also positive for the HBsAg, HBcAg, and HbxAg proteins, indicative of viral replication. An example of a protocol for comparing unmodified and PEGylated murine IFN-β in this model is given below:

30 mice (5 groups of 5 plus 5 spare) with comparable viral titer are titered at two independent time points (at least 1 week apart) to establish a baseline titer and to ensure that their titers remain constant prior to dosing with murine IFN-β. Groups of 5 mice are dosed 3 times per week (Monday, Wednesday, and Friday) subcutaneously with the following samples, as shown in Table 7.

TABLE 7

| Group | Dosing sample |
|---|---|
| 1 | Vehicle control (1 mg/mL murine serum albumin, MSA) |
| 2 | 30 U unmodified murine IFN-β in 1 mg/mL MSA |
| 3 | 300 U unmodified murine IFN-β in 1 mg/mL MSA |
| 4 | 3000 U unmodified murine IFN-β in 1 mg/mL MSA |
| 5 | 30 U PEGylated murine IFN-β in 1 mg/mL MSA |
| 6 | 300 U PEGylated murine IFN-β in 1 mg/mL MSA |
| 7 | 3000 U PEGylated murine IFN-β in 1 mg/mL MSA |

Viral titers are determined weekly during dosing and weekly to bi-weekly for 6 months following dosing. Plots of viral titer against time are constructed for a comparison of vehicle and IFN-β-treated animals with respect to the clearance and re-establishment of viral titer. A second study is then performed with the appropriate doses of unmodified and PEGylated murine IFN-β with 10-20 mice per group for a total of 30-60 mice (10-20 for control, 10-20 for unmodified murine IFN-β, and 10-20 for PEGylated murine IFN-β). Viral titers are assessed as above, and at sacrifice, serum is analyzed for viral titer as well as for HbsAg by SDS-PAGE and Western blotting. Livers are also removed, frozen or fixed as necessary, and stained for the presence of HbsAg, HbcAg, and HbxAg. Other appropriate histological, histochemical, or biochemical tests familiar to those in the art may also be performed on serum and tissue samples.

An in vivo mouse model is also available to test the effect of unmodified and PEGylated human IFN-β-1a on the levels of human Hepatitis C Virus (HCV) in mice carrying chimaeric human livers. Mercer et al., Nature Medicine 7:927 (2001). In this model, normal human hepatocytes are grafted into SCID mice carrying a plasminogen activator transgene (Alb-uPA) and the mice inoculated with serum from humans infected with the different gentoypes of HCV. The engrafted human liver cells become infected by the virus and the virus replicates. Levels of HCV RNA in the serum can be quantified by PCR, as well as the levels of positive and negative (replicative form) RNA in the liver cells. An appropriate study protocol similar to (but not limited to) that described above for unmodified and PEGylated murine IFN-β in transgenic HBV SCID mice is performed to assess the efficacy of unmodified and PEGylated human IFN-β-1a in this model i.e. to determine the effect of treatment on HCV titer, liver histology, serum ALT levels, and the presence of HCV replicative forms in the engrafted human liver tissue. Other appropriate histological, histochemical, or biochemical tests familiar to those in the art may also be performed on serum and tissue samples.

We claim:

1. A method of treating a patient having an interferon-susceptible viral infection, comprising administering to the patient an effective amount of a composition having the structure according to the formula

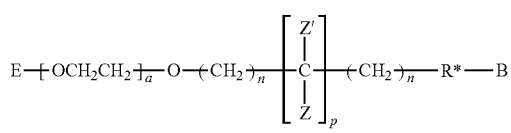

wherein E is hydrogen, a straight- or branched-chain $C_1$ to $C_{20}$ alkyl group, or a detectable label;

a is an integer from 4 to 10,000;

each Z and Z' is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein in the substituted groups the substitution is selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, an aromatic moiety, a heteroaromatic moiety, imino, silyl, ether, and alkylthio, provided that at least one Z or Z' is not hydrogen;

R* is a linking moiety formed from the reaction of a moiety selected from the group consisting of aldehyde, aldehyde hydrate, and acetal, with B, wherein B is a biologically-active molecule or precursor thereof that comprises interferon-beta-1a (IFN-β-1a);

each n is 0 or an integer from 1 to 5; and p is 1, 2, or 3.

2. The method of claim 1, wherein the viral infection is chronic hepatitis C.

3. A method of treating multiple sclerosis in a patient suffering therefrom, comprising administering to said patient an effective amount of a composition having the structure according to the formula wherein E is hydrogen, a straight- or branched-chain $C_1$ to $C_{20}$ alkyl group, or a detectable label;

a is an integer from 4 to 10,000;

each Z and Z' is independently hydrogen, a straight- or branched-chain, saturated or unsaturated $C_1$ to $C_{20}$ alkyl or heteroalkyl group, $C_3$ to $C_8$ saturated or unsaturated cyclic alkyl or cyclic heteroalkyl, a substituted or unsubstituted aryl or heteroaryl group or a substituted or unsubstituted alkaryl wherein the alkyl is a $C_1$ to $C_{20}$ saturated or unsaturated alkyl or heteroalkaryl group, wherein in the substituted groups the substitution is selected from the group consisting of halogen, hydroxyl, carbonyl, carboxylate, ester, formyl, acyl, thiocarbonyl, thioester, thioacetate, thioformate, alkoxyl, phosphoryl, phosphonate, phosphinate, amino, amido, amidine, imine, cyano, nitro, azido, sulfhydryl, sulfate, sulfonate, sulfamoyl, sulfonamido, sulfonyl, heterocyclyl, aralkyl, an aromatic moiety, a heteroaromatic moiety, imino, silyl, ether, and alkylthio, provided that at least one Z or Z' is not hydrogen;

R* is a linking moiety formed from the reaction of a moiety selected from the group consisting of aldehyde, aldehyde hydrate, and acetal, with B, wherein B is a biologically-active molecule or precursor thereof that comprises interferon-beta-1a (IFN-β-1a);

each n is 0 or an integer from 1 to 5; and p is 1, 2, or 3.

* * * * *